US008257707B2

(12) United States Patent
Smith et al.

(10) Patent No.: US 8,257,707 B2
(45) Date of Patent: Sep. 4, 2012

(54) IL-18 RECEPTOR ANTIGEN BINDING PROTEINS

(75) Inventors: Dirk E. Smith, Bainbridge Island, WA (US); John E. Sims, Seattle, WA (US); Jeffrey T. McGrew, Woodinville, WA (US); Marek Z. Kubin, Bainbridge Island, WA (US); Duncan Cochrane, Granta Park (GA); Louise Conroy, Granta Park (GA)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 12/670,112

(22) PCT Filed: Jul. 24, 2008
(Under 37 CFR 1.47)

(86) PCT No.: PCT/US2008/071047
§ 371 (c)(1),
(2), (4) Date: Aug. 16, 2010

(87) PCT Pub. No.: WO2009/015284
PCT Pub. Date: Jan. 29, 2009

(65) Prior Publication Data
US 2011/0014201 A1    Jan. 20, 2011

Related U.S. Application Data

(60) Provisional application No. 60/951,691, filed on Jul. 24, 2007, provisional application No. 60/951,692, filed on Jul. 24, 2007, provisional application No. 61/073,142, filed on Jun. 17, 2008.

(51) Int. Cl.
A61K 39/395    (2006.01)
(52) U.S. Cl. .............. 424/133.1; 424/141.1; 424/143.1; 530/388.1; 530/350; 536/23.1; 435/69.1; 435/235.1; 435/325; 435/6.1
(58) Field of Classification Search .......................... None
See application file for complete search history.

(56) References Cited

U.S. PATENT DOCUMENTS

| | | | |
|---|---|---|---|
| 5,776,731 A | 7/1998 | Parnet | |
| 6,090,918 A | 7/2000 | Parnet | |
| 6,451,760 B1 | 9/2002 | Parnet | |
| 6,492,496 B1 * | 12/2002 | Parnet et al. ............. | 530/388.22 |
| 6,589,764 B1 | 7/2003 | Sims | |
| 6,600,022 B1 | 7/2003 | Torigoe et al. | |
| 6,664,077 B1 | 12/2003 | Sims | |
| 6,692,740 B2 | 2/2004 | Sims | |
| 6,693,171 B2 | 2/2004 | Sims | |
| 7,001,599 B2 | 2/2006 | Parnet | |
| 7,169,581 B2 | 1/2007 | Sims | |
| 7,235,238 B2 | 6/2007 | Parnet | |
| 7,270,817 B2 | 9/2007 | Sims | |
| 7,625,710 B2 | 12/2009 | Parnet | |
| 7,704,945 B2 | 4/2010 | Sims | |
| 7,838,248 B2 | 11/2010 | Sims | |
| 7,993,845 B2 | 8/2011 | Sims | |
| 8,034,343 B2 | 10/2011 | Parnet | |
| 2002/0098185 A1 | 7/2002 | Sims et al. | |
| 2003/0059937 A1 | 3/2003 | Ruben et al. | |
| 2004/0018198 A1 | 1/2004 | Gudas et al. | |
| 2004/0023336 A1 | 2/2004 | Heavner et al. | |
| 2005/0147610 A1 | 7/2005 | Ghayur et al. | |
| 2007/0025992 A1 | 2/2007 | Takayama et al. | |

FOREIGN PATENT DOCUMENTS

| | | |
|---|---|---|
| EP | 1808446 A1 | 7/2007 |
| WO | 97/31010 A1 | 8/1997 |
| WO | 99/37772 A1 | 7/1999 |
| WO | 99/37773 A1 | 7/1999 |
| WO | 01/007480 A2 | 2/2001 |
| WO | 01/27279 A1 | 4/2001 |
| WO | 02/092008 A2 | 11/2002 |
| WO | 03/057821 A2 | 7/2003 |

OTHER PUBLICATIONS

Nishida et al., "Cloning and expression of a single-chain Fv fragment specific for the human interleukin 18 receptor," Hybridoma 17(6):577-581, 1998.
Vermot-Desroches et al., "Monoclonal antibodies specific for the IL-18 receptor," Cell Immunol, 236:101-104, 2005.
Caldas et al., Humanization of the anti-CD18 antibody 6.7: an unexpected effect of a framework residue in binding to antigen, Mol Immunol 39(15):941-952, 2003.
Casset et al., "A peptide mimetic of an anti-CD4 monoclonal antibody by rational design," Biochem Biophys Res Commun 307(1):198-205, 2003.
Chien et al., "Significant structural and functional change of an antigen-binding site by a distant amino acid substitution: proposal of a structural mechanism," Proc Natl Acad Sci USA 86(14):5532-5536, 1989.
De Pascalis et al., "Grafting of 'abbreviated' complementarity-determining regions containing specificity-determining residues essential for ligand contact to engineer a less immunogenic humanized monoclonal antibody," J Immunol 169(6):3076-3084, 2002.
Guisti et al., "Somatic diversification of S107 from an antiphosphocholine to an anti-DNA autoantibody is due to a single base change in its heavy chain variable region," Proc Natl Acad Sci USA 84(9):2926-2930, 1987.
Gussow and Seemann, "Humanization of monoclonal antibodies," Methods Enzymol 203:99-121, 1991.
Holm et al., "Functional mapping and single chain construction of the anti-cytokeratin 8 monoclonal antibody TS1," Mol Immunol 44(6):1075-1084, 2007.
MacCallum et al., "Antibody-antigen interactions: contact analysis and binding site topography," J Mol Biol 262(5):732-745, 1996.

(Continued)

*Primary Examiner* — Dong Jiang
(74) *Attorney, Agent, or Firm* — Thomas J. Wrona

(57) ABSTRACT

Provided herein are IL-18 receptor antigen binding proteins and polynucleotides encoding the same. Expression vectors and host cells comprising the same for production of the antigen binding proteins are also provided. In addition, provided are compositions and methods for diagnosing and treating diseases mediated by IL-18 receptor.

21 Claims, 34 Drawing Sheets

OTHER PUBLICATIONS

Mariuzza et al., "The structural basis of antigen-antibody recognition," Annu Rev Biophys Biophys Chem 16:139-159, 1987.

Rudikoff et al., "Single amino acid substitution altering antigen-binding specificity," Proc Natl Acad Sci USA 79(6):1979-1983, 1982.

Wu et al., "Humanization of a murine monoclonal antibody by simultaneous optimization of framework and CDR residues," J Mol Biol 294(1):151-162, 1999.

R&D Systems online catalog, "Human IL-18 Rα/IL-1 R5 Antibody," Jan. 1, 2007, retrieved from the Internet: URL:http://www.rndsystems.com/pdf/mab840.pdf [retrieved on Feb. 3, 2012].

Tokmadzic, V.S. et al., "IL-18 is present at the maternal-fetal interface and enhances cytotoxic activity of decidual lymphocytes," AJRI 48:191-200 (2002).

Wu, C. et al., "IL-18 receptor β-induced changes in the presentation of IL-18 binding sites affect ligand binding and signal transduction," J Immunol 170:5571-5577 (2003).

Imaoka H. et al., "Interleukin-18 production and pulmonary function in COPD," Eur Respir J 31:287-297 (2008).

* cited by examiner

AM$_H$1 polynucleotide sequence (SEQ ID:35)

```
caggtgcagctggtgcagtctggggggaggcgtggtccagcctggggaggtccctgagactc      60
 Q  V  Q  L  V  Q  S  G  G  G  V  V  Q  P  G  R  S  L  R  L
tcctgtgcagcgtctggattcaccttcagcggttatggcatgcactgggtccgccaggct     120
 S  C  A  A  S  G  F  T  F  S  G  Y  G  M  H  W  V  R  Q  A
ccaggcaaggggctggagtgggtggcagtaatatcaaatgatggaagtaagaaatattat     180
 P  G  K  G  L  E  W  V  A  V  I  S  N  D  G  S  K  K  Y  Y
tcagactccgtgaagggccgattcaccatctccagagacaattccaaaaacacgctgtat     240
 S  D  S  V  K  G  R  F  T  I  S  R  D  N  S  K  N  T  L  Y
ctgcagatgaacagcctgagagctgaggacacggctgtatattactgtgcgaaagggtcc     300
 L  Q  M  N  S  L  R  A  E  D  T  A  V  Y  Y  C  A  K  G  S
agttccatatggctgacccagtccctggaccactgggggcaggggaccacggtcaccgtc     360
 S  S  I  W  L  T  Q  S  L  D  H  W  G  Q  G  T  T  V  T  V
tcctca                                                            366
 S  S
```

AM$_H$1 amino acid sequence (SEQ ID:1)

```
QVQLVQSGGGVVQPGRSLRLSCAASGFTFSGYGMHWVRQAPGKGLEWVAVISNDGSKKYY      60
SDSVKGRFTISRDNSKNTLYLQMNSLRAEDTAVYYCAKGSSSIWLTQSLDHWGQGTTVTV     120
SS                                                                122
```

AM$_H$2 polynucleotide sequence (SEQ ID:36)

```
gaggtgcagctggtggagtctggggggaggcgtggtccagcctggggaggtccctgagactc     60
 E  V  Q  L  V  E  S  G  G  G  V  V  Q  P  G  R  S  L  R  L
tcctgtgcagcgtctggattcaccttcagcggttatggcatgcactgggtccgccaggct    120
 S  C  A  A  S  G  F  T  F  S  G  Y  G  M  H  W  V  R  Q  A
ccaggcaaggggctggagtgggtggcagtaatatcaaatgatggaagtaagaaatattat    180
 P  G  K  G  L  E  W  V  A  V  I  S  N  D  G  S  K  K  Y  Y
tcagactccgtgaagggccgattcaccatctccagagacaattccaaaaacacgctgtat    240
 S  D  S  V  K  G  R  F  T  I  S  R  D  N  S  K  N  T  L  Y
ctgcagatgaacagcctgagagctgaggacacggctgtatattactgtgcgaaagggtcc    300
 L  Q  M  N  S  L  R  A  E  D  T  A  V  Y  Y  C  A  K  G  S
agttccatatggctgacccagtccctggaccactgggggcaggggaccacggtcaccgtc    360
 S  S  I  W  L  T  Q  S  L  D  H  W  G  Q  G  T  T  V  T  V
tcctca                                                           366
 S  S
```

AM$_H$2 amino acid sequence (SEQ ID NO:2)

```
EVQLVESGGGVVQPGRSLRLSCAASGFTFSGYGMHWVRQAPGKGLEWVAVISNDGSKKYY      60
SDSVKGRFTISRDNSKNTLYLQMNSLRAEDTAVYYCAKGSSSIWLTQSLDHWGQGTTVTV     120
SS                                                                122
```

FIGURE 1A

AM_H3 polynucleotide sequence (SEQ ID 37)

```
caggtgcagctggtgcagtctggggggaggcgtggtccagcctgggaggtccctgagactc    60
 Q  V  Q  L  V  Q  S  G  G  G  V  V  Q  P  G  R  S  L  R  L
tcctgtgcagcgtctggattcaccttcagcggttatggcatgcactgggtccgccaggct   120
 S  C  A  A  S  G  F  T  F  S  G  Y  G  M  H  W  V  R  Q  A
ccaggcaaggggctggagtgggtggcagtaatatcaaatgatggaagtaagaaatattat   180
 P  G  K  G  L  E  W  V  A  V  I  S  N  D  G  S  K  K  Y  Y
tcagactccgtgaagggccgattcaccatctccagagacaattccaaaaacacgctgtat   240
 S  D  S  V  K  G  R  F  T  I  S  R  D  N  S  K  N  T  L  Y
ctgcagatgaacagcctgagagctgaggacacggctgtatattactgtgcgaaagggtcc   300
 L  Q  M  N  S  L  R  A  E  D  T  A  V  Y  Y  C  A  K  G  S
agttccatatggctgtcgcagtccctggacggctggggcaggggaccacggtcaccgtc   360
 S  S  I  W  L  S  Q  S  L  D  G  W  G  Q  G  T  T  V  T  V
tcctca                                                         366
 S  S
```

AM_H3 amino acid sequence (SEQ ID NO:3)

```
QVQLVQSGGGVVQPGRSLRLSCAASGFTFSGYGMHWVRQAPGKGLEWVAVISNDGSKKYY    60
SDSVKGRFTISRDNSKNTLYLQMNSLRAEDTAVYYCAKGSSSIWLSQSLDGWGQGTTVTV   120
SS                                                             122
```

AM_H4 polynucleotide sequence (SEQ ID:38)

```
gaggtgcagctggtggagtctggggggaggcgtggtccagcctgggaggtccctgagactc    60
 E  V  Q  L  V  E  S  G  G  G  V  V  Q  P  G  R  S  L  R  L
tcctgtgcagcgtctggattcaccttcagcggttatggcatgcactgggtccgccaggct   120
 S  C  A  A  S  G  F  T  F  S  G  Y  G  M  H  W  V  R  Q  A
ccaggcaaggggctggagtgggtggcagtaatatcaaatgatggaagtaagaaatattat   180
 P  G  K  G  L  E  W  V  A  V  I  S  N  D  G  S  K  K  Y  Y
tcagactccgtgaagggccgattcaccatctccagagacaattccaaaaacacgctgtat   240
 S  D  S  V  K  G  R  F  T  I  S  R  D  N  S  K  N  T  L  Y
ctgcagatgaacagcctgagagctgaggacacggctgtatattactgtgcgaaagggtcc   300
 L  Q  M  N  S  L  R  A  E  D  T  A  V  Y  Y  C  A  K  G  S
agttccatatggctgtcgcagtccctggacggctggggcaggggaccacggtcaccgtc   360
 S  S  I  W  L  S  Q  S  L  D  G  W  G  Q  G  T  T  V  T  V
tcctca                                                         366
 S  S
```

AM_H4 amino acid sequence (SEQ ID:4)

```
EVQLVESGGGVVQPGRSLRLSCAASGFTFSGYGMHWVRQAPGKGLEWVAVISNDGSKKYY    60
SDSVKGRFTISRDNSKNTLYLQMNSLRAEDTAVYYCAKGSSSIWLSQSLDGWGQGTTVTV   120
SS                                                             122
```

FIGURE 1B

AM$_H$5 polynucleotide sequence (SEQ ID:39)

```
caggtgcagctggtgcagtctgggggaggcgtggtccagcctggaggtccctgagactc        60
 Q  V  Q  L  V  Q  S  G  G  G  V  V  Q  P  G  R  S  L  R  L
tcctgtgcagcgtctggattcaccttcagcggttatggcatgcactgggtccgccaggct      120
 S  C  A  A  S  G  F  T  F  S  G  Y  G  M  H  W  V  R  Q  A
ccaggcaaggggctggagtgggtggcagtaatatcaaatgatggaagtaagaaatattat      180
 P  G  K  G  L  E  W  V  A  V  I  S  N  D  G  S  K  K  Y  Y
tcagactccgtgaagggccgattcaccatctccagagacaattccaaaaacacgctgtat      240
 S  D  S  V  K  G  R  F  T  I  S  R  D  N  S  K  N  T  L  Y
ctgcagatgaacagcctgagagctgaggacacggctgtatattactgtgcgaaagggtcc      300
 L  Q  M  N  S  L  R  A  E  D  T  A  V  Y  Y  C  A  K  G  S
agttccatatggctgacctcggccctgaacctgtgggggcaggggaccacggtcaccgtc      360
 S  S  I  W  L  T  S  A  L  N  L  W  G  Q  G  T  T  V  T  V
tcctca                                                            366
 S  S
```

AM$_H$5 amino acid sequence (SEQ ID:5)

```
QVQLVQSGGGVVQPGRSLRLSCAASGFTFSGYGMHWVRQAPGKGLEWVAVISNDGSKKYY       60
SDSVKGRFTISRDNSKNTLYLQMNSLRAEDTAVYYCAKGSSSIWLTSALNLWGQGTTVTV      120
SS                                                                122
```

AM$_H$6 polynucleotide sequence (SEQ ID:40)

```
gaggtgcagctggtggagtctgggggaggcgtggtccagcctggaggtccctgagactc        60
 E  V  Q  L  V  E  S  G  G  G  V  V  Q  P  G  R  S  L  R  L
tcctgtgcagcgtctggattcaccttcagcggttatggcatgcactgggtccgccaggct      120
 S  C  A  A  S  G  F  T  F  S  G  Y  G  M  H  W  V  R  Q  A
ccaggcaaggggctggagtgggtggcagtaatatcaaatgatggaagtaagaaatattat      180
 P  G  K  G  L  E  W  V  A  V  I  S  N  D  G  S  K  K  Y  Y
tcagactccgtgaagggccgattcaccatctccagagacaattccaaaaacacgctgtat      240
 S  D  S  V  K  G  R  F  T  I  S  R  D  N  S  K  N  T  L  Y
ctgcagatgaacagcctgagagctgaggacacggctgtatattactgtgcgaaagggtcc      300
 L  Q  M  N  S  L  R  A  E  D  T  A  V  Y  Y  C  A  K  G  S
agttccatatggctgacctcggccctgaacctgtgggggcaggggaccacggtcaccgtc      360
 S  S  I  W  L  T  S  A  L  N  L  W  G  Q  G  T  T  V  T  V
tcctca                                                            366
 S  S
```

AM$_H$6 polynucleotide sequence (SEQ ID:6)

```
EVQLVESGGGVVQPGRSLRLSCAASGFTFSGYGMHWVRQAPGKGLEWVAVISNDGSKKYY       60
SDSVKGRFTISRDNSKNTLYLQMNSLRAEDTAVYYCAKGSSSIWLTSALNLWGQGTTVTV      120
SS                                                                122
```

FIGURE 1C

AM$_H$7 polynucleotide sequence (SEQ ID:41)

```
gaggtgcagctggtggagtctgggggaggcgtggtccagcctgggaggtccctgagactc     60
 E  V  Q  L  V  E  S  G  G  G  V  V  Q  P  G  R  S  L  R  L
tcctgtgcagcgtctggattcaccttcagcggttatggcatgcactgggtccgccaggct    120
 S  C  A  A  S  G  F  T  F  S  G  Y  G  M  H  W  V  R  Q  A
ccaggcaaggggctggagtgggtggcagtaatatcaaatgatggaagtaagaaatattat    180
 P  G  K  G  L  E  W  V  A  V  I  S  N  D  G  S  K  K  Y  Y
tcagactccgtgaagggccgattcaccatctccagagacaattccaaaaacacgctgtat    240
 S  D  S  V  K  G  R  F  T  I  S  R  D  N  S  K  N  T  L  Y
ctgcagatgaacagcctgagagctgaggacacggctatatattactgtgcgaaagggtcc    300
 L  Q  M  N  S  L  R  A  E  D  T  A  I  Y  Y  C  A  K  G  S
agttccatatggttcggggagaccgttgactactggggcaggggaccacg             351
 S  S  I  W  F  G  E  T  V  D  Y  W  G  Q  G  T  T
```

AM$_H$7 amino acid sequence (SEQ ID:7)

```
EVQLVESGGGVVQPGRSLRLSCAASGFTFSGYGMHWVRQAPGKGLEWVAVISNDGSKKYY     60
SDSVKGRFTISRDNSKNTLYLQMNSLRAEDTAIYYCAKGSSSIWFGETVDYWGQGTT      117
```

AM$_H$8 polynucleotide sequence (SEQ ID:42)

```
caggtgcagctggtgcagtctggggctgaggtgaagaagcctggggcctcagtgaaggtc     60
 Q  V  Q  L  V  Q  S  G  A  E  V  K  K  P  G  A  S  V  K  V
tcctgcaaggtttccggatacaccctcactgaattatccatgcactgggtgcgacaggct    120
 S  C  K  V  S  G  Y  T  L  T  E  L  S  M  H  W  V  R  Q  A
cctggaaaagggcttgagtggatgggaggttttgatcgtgaagatgatgaaacaatccac    180
 P  G  K  G  L  E  W  M  G  G  F  D  R  E  D  D  E  T  I  H
gcacagaagttccagggcagagtcaccatgaccgaggacacatctacagacacagcctac    240
 A  Q  K  F  Q  G  R  V  T  M  T  E  D  T  S  T  D  T  A  Y
atggaactgagcagcctgcgatctgaggacacggccgtttattactgtgcaacagatctt    300
 M  E  L  S  S  L  R  S  E  D  T  A  V  Y  Y  C  A  T  D  L
atggtgtggggcgattttggatccagcactggggccaggggacactggtcaccgtctcc    360
 M  V  W  G  D  F  W  I  Q  H  W  G  Q  G  T  L  V  T  V  S
tca                                                             363
 S
```

AM$_H$8 polynucleotide sequence (SEQ ID:8)

```
QVQLVQSGAEVKKPGASVKVSCKVSGYTLTELSMHWVRQAPGKGLEWMGGFDREDDETIH     60
AQKFQGRVTMTEDTSTDTAYMELSSLRSEDTAVYYCATDLMVWGDFWIQHWGQGTLVTVS   120
S                                                              121
```

FIGURE 1D

AM_H9 polynucleotide sequence (SEQ ID:43)

```
caggtgcagctggtgcagtctggggctgaggtgaagaagcctggggcctcagtgaaggtc    60
 Q  V  Q  L  V  Q  S  G  A  E  V  K  K  P  G  A  S  V  K  V
tcctgcaaggtttccggatacacccctcactgaattatccatgcactgggtgcgacaggct   120
 S  C  K  V  S  G  Y  T  L  T  E  L  S  M  H  W  V  R  Q  A
cctggaaaagggcttgagtggatgggaggttttgatcgtgaagatgatgaaacaatccac   180
 P  G  K  G  L  E  W  M  G  G  F  D  R  E  D  D  E  T  I  H
gcacagaagttccagggcagagtcaccatgaccgaggacacatctacagacacagcctac   240
 A  Q  K  F  Q  G  R  V  T  M  T  E  D  T  S  T  D  T  A  Y
atggaactgagcagcctgcgatctgaggacacggccgtttattactgtgcaacagatctt   300
 M  E  L  S  S  L  R  S  E  D  T  A  V  Y  Y  C  A  T  D  L
atggtgtggggcgattttggatccagcactggggccaggggacactggtcaccgtctcc   360
 M  V  W  G  D  F  W  I  Q  H  W  G  Q  G  T  L  V  T  V  S
tca                                                            363
 S
```

AM_H9 amino acid sequence (SEQ ID:9)

```
QVQLVQSGAEVKKPGASVKVSCKVSGYTLTELSMHWVRQAPGKGLEWMGGFDREDDETIH    60
AQKFQGRVTMTEDTSTDTAYMELSSLRSEDTAVYYCATDLMVWGDFWIQHWGQGTLVTVS   120
S                                                              121
```

AM_H10 polynucleotide sequence (SEQ ID:44)

```
caggtgcagctggtgcagtctggggctgaggtgaagaagcctggggcctcagtgaaggtc    60
 Q  V  Q  L  V  Q  S  G  A  E  V  K  K  P  G  A  S  V  K  V
tcctgcaaggtttccggatacacccctcactgaattatccatgcactgggtgcgacaggct   120
 S  C  K  V  S  G  Y  T  L  T  E  L  S  M  H  W  V  R  Q  A
cctggaaaagggcttgagtggatgggaggttttgatcgtgaagatgatgaaacaatccac   180
 P  G  K  G  L  E  W  M  G  G  F  D  R  E  D  D  E  T  I  H
gcacagaagttccagggcagagtcaccatgaccgaggacacatctacagacacagcctac   240
 A  Q  K  F  Q  G  R  V  T  M  T  E  D  T  S  T  D  T  A  Y
atggaactgagcagcctgcgatctgaggacacggccgtttattactgtgcaacagatctt   300
 M  E  L  S  S  L  R  S  E  D  T  A  V  Y  Y  C  A  T  D  L
atggcctgggactacccgcccatccagcactggggccaggggacactggtcaccgtctcc   360
 M  A  W  D  Y  P  P  I  Q  H  W  G  Q  G  T  L  V  T  V  S
tca                                                            363
 S
```

AM_H10 amino acid sequence (SEQ ID:10)

```
QVQLVQSGAEVKKPGASVKVSCKVSGYTLTELSMHWVRQAPGKGLEWMGGFDREDDETIH    60
AQKFQGRVTMTEDTSTDTAYMELSSLRSEDTAVYYCATDLMAWDYPPIQHWGQGTLVTVS   120
S                                                              121
```

FIGURE 1E

AM_H11 polynucleotide sequence (SEQ ID:45)

```
caggtgcagctggtgcagtctggggctgaggtgaagaagcctggggcctcagtgaaggtc        60
 Q  V  Q  L  V  Q  S  G  A  E  V  K  K  P  G  A  S  V  K  V
tcctgcaaggtttccggatacacactcactgaattatccatgcactgggtgcgacaggct       120
 S  C  K  V  S  G  Y  T  L  T  E  L  S  M  H  W  V  R  Q  A
cctggaaaagggcttgagtggatgggaggttttgatcgtgaagatgatgaaacaatccac       180
 P  G  K  G  L  E  W  M  G  G  F  D  R  E  D  D  E  T  I  H
gcacagaagttccagggcagagtcaccatgaccgaggacacatctacagacacagcctac       240
 A  Q  K  F  Q  G  R  V  T  M  T  E  D  T  S  T  D  T  A  Y
atggaactgagcagcctgcgatctgaggacacggccgtttattactgtgcaacagatctt       300
 M  E  L  S  S  L  R  S  E  D  T  A  V  Y  Y  C  A  T  D  L
atggtgtggaacttcccccccatccagcactggggccaggggacactggtcaccgtctcc       360
 M  V  W  N  F  P  P  I  Q  H  W  G  Q  G  T  L  V  T  V  S
tca                                                                363
 S
```

AM_H11 amino acid sequence (SEQ ID:11)

```
QVQLVQSGAEVKKPGASVKVSCKVSGYTLTELSMHWVRQAPGKGLEWMGGFDREDDETIH        60
AQKFQGRVTMTEDTSTDTAYMELSSLRSEDTAVYYCATDLMVWNFPPIQHWGQGTLVTVS       120
S                                                                  121
```

AM_H12 polynucleotide sequence (SEQ ID:46)

```
caggtgcagctggtgcagtctggggctgaggtgaagaagcctggggcctcagtgaaggtc        60
 Q  V  Q  L  V  Q  S  G  A  E  V  K  K  P  G  A  S  V  K  V
tcctgcaaggtttccggatacacactcactgaattatccatgcactgggtgcgacaggct       120
 S  C  K  V  S  G  Y  T  L  T  E  L  S  M  H  W  V  R  Q  A
cctggaaaagggcttgagtggatgggaggttttgatcgtgaagatgatgaaacaatccac       180
 P  G  K  G  L  E  W  M  G  G  F  D  R  E  D  D  E  T  I  H
gcacagaagttccagggcagagtcaccatgaccgaggacacatctacagacacagcctac       240
 A  Q  K  F  Q  G  R  V  T  M  T  E  D  T  S  T  D  T  A  Y
atggaactgagcagcctgcgatctgaggacacggccgtttattactgtgcaacagatctt       300
 M  E  L  S  S  L  R  S  E  D  T  A  V  Y  Y  C  A  T  D  L
atggtgtgggcgattttggatccagcactggggcaaggggacaatg                     348
 M  V  W  G  D  F  W  I  Q  H  W  G  K  G  T  M
```

AM_H12 amino acid sequence (SEQ ID:12)

```
QVQLVQSGAEVKKPGASVKVSCKVSGYTLTELSMHWVRQAPGKGLEWMGGFDREDDETIH        60
AQKFQGRVTMTEDTSTDTAYMELSSLRSEDTAOVYYCATDLMVWGDFWIQHWGKGTM          111
```

FIGURE 1F

AM$_H$13 polynucleotide sequence (SEQ ID:47)

```
gaggtgcagctgttggagtctgggggaggcttggtacagcctggggggtccctgagactc    60
 E   V   Q   L   L   E   S   G   G   G   L   V   Q   P   G   G   S   L   R   L
tcctgtgcagcctctggattcacctttagcagctatgccatgagctgggtccgccaggct   120
 S   C   A   A   S   G   F   T   F   S   S   Y   A   M   S   W   V   R   Q   A
ccagggaaggggctggagtgggtctcagctattagtggtagtggtggtggcacatactac   180
 P   G   K   G   L   E   W   V   S   A   I   S   G   S   G   G   G   T   Y   Y
gcagactccgtgaagggccggttcaccatctccagagacaattccaagaacacgctgtat   240
 A   D   S   V   K   G   R   F   T   I   S   R   D   N   S   K   N   T   L   Y
ctgcaaatgaacagcctgagagccgaggacacggccgtgtattactgtgcgagaattcgg   300
 L   Q   M   N   S   L   R   A   E   D   T   A   V   Y   Y   C   A   R   I   R
ggcgactaccggacggacatctggggccagggaaccacggtcaccgtctcctca          354
 G   D   Y   R   T   D   I   W   G   Q   G   T   T   V   T   V   S   S
```

AM$_H$13 amino acid sequence (SEQ ID:13)

```
EVQLLESGGGLVQPGGSLRLSCAASGFTFSSYAMSWVRQAPGKGLEWVSAISGSGGGTYY    60
ADSVKGRFTISRDNSKNTLYLQMNSLRAEDTAVYYCARIRGDYRTDIWGQGTTVTVSS    118
```

AM$_H$14 polynucleotide sequence (SEQ ID:48)

```
gaggtgcagctgttggagtctgggggaggcttggtacagcctggggggtccctgagactc    60
 E   V   Q   L   L   E   S   G   G   G   L   V   Q   P   G   G   S   L   R   L
tcctgtgcagcctctggattcacctttagcagctatgccatgagctgggtccgccaggct   120
 S   C   A   A   S   G   F   T   F   S   S   Y   A   M   S   W   V   R   Q   A
ccagggaaggggctggagtgggtctcagctattagtggtagtggtggtggcacatactac   180
 P   G   K   G   L   E   W   V   S   A   I   S   G   S   G   G   G   T   Y   Y
gcagactccgtgaagggccggtccaccatctccagagacaattccaagaacacgctgtat   240
 A   D   S   V   K   G   R   S   T   I   S   R   D   N   S   K   N   T   L   Y
ctgcaaatgaacagcctgagagccgaggacacggccgtgtattactgtgcgagaattcgg   300
 L   Q   M   N   S   L   R   A   E   D   T   A   V   Y   Y   C   A   R   I   R
ggggactaccggacggacatctggggccggggaaccctggtcaccgtctcctca          354
 G   D   Y   R   T   D   I   W   G   R   G   T   L   V   T   V   S   S
```

AM$_H$14 amino acid sequence (SEQ ID:14)

```
EVQLLESGGGLVQPGGSLRLSCAASGFTFSSYAMSWVRQAPGKGLEWVSAISGSGGGTYY    60
ADSVKGRSTISRDNSKNTLYLQMNSLRAEDTAVYYCARIRGDYRTDIWGRGTLVTVSS    118
```

FIGURE 1G

AM_H15 polynucleotide sequence (SEQ ID:49)

```
gaggtgcagctgttggagtctgggggaggcttggcacagcctggggggtccctgagactc    60
 E  V  Q  L  L  E  S  G  G  G  L  A  Q  P  G  G  S  L  R  L
tcctgtgcagcctctgggttcacctttagcagctatgccatgagctgggtccgccaggct    120
 S  C  A  A  S  G  F  T  F  S  S  Y  A  M  S  W  V  R  Q  A
ccagggaaggggctggagtgggtctcagctattagtggtagtggtggtagcacatactac    180
 P  G  K  G  L  E  W  V  S  A  I  S  G  S  G  G  S  T  Y  Y
gcagactccgtgaagggccggttcaccatctccagagacaattccaagaacacgctgtat    240
 A  D  S  V  K  G  R  F  T  I  S  R  D  N  S  K  N  T  L  Y
ctgcaaatgaacagcctgagagccgaggacacggccgtgtattactgtgcgagagttcgg    300
 L  Q  M  N  S  L  R  A  E  D  T  A  V  Y  Y  C  A  R  V  R
ggggactaccggacggacatctggggccggggaaccctggtcaccgtctcctca          354
 G  D  Y  R  T  D  I  W  G  R  G  T  L  V  T  V  S  S
```

AM_H15 amino acid sequence (SEQ ID:15)

```
EVQLLESGGGLAQPGGSLRLSCAASGFTFSSYAMSWVRQAPGKGLEWVSAISGSGGSTYY    60
ADSVKGRFTISRDNSKNTLYLQMNSLRAEDTAVYYCARVRGDYRTDIWGRGTLVTVSS     118
```

AM_H16 polynucleotide sequence (SEQ ID:50)

```
gaggtgcagctgttggagtctgggggaggcttggtacagcctggggggtccctgagactc    60
 E  V  Q  L  L  E  S  G  G  G  L  V  Q  P  G  G  S  L  R  L
tcctgtgcagcctctagattcacctttagcagctatgccatgagctgggtccgccaggct    120
 S  C  A  A  S  R  F  T  F  S  S  Y  A  M  S  W  V  R  Q  A
ccagggaaggggctggagtgggtctcagctattagtggtagtggtggtagcacatactac    180
 P  G  K  G  L  E  W  V  S  A  I  S  G  S  G  G  S  T  Y  Y
gcagactccgtgaagggccggttcaccatctccagagacaattccaagaacacgctgtat    240
 A  D  S  V  K  G  R  F  T  I  S  R  D  N  S  K  N  T  L  Y
ctgcaaatgaacagcctgagagccgaggacacggccgtgtattactgtgcgagagttcgg    300
 L  Q  M  N  S  L  R  A  E  D  T  A  V  Y  Y  C  A  R  V  R
ggggactaccggacggacatctggggccggggaaccctggtcaccgtctcctca          354
 G  D  Y  R  T  D  I  W  G  R  G  T  L  V  T  V  S  S
```

AM_H16 amino acid sequence (SEQ ID:16)

```
EVQLLESGGGLVQPGGSLRLSCAASRFTFSSYAMSWVRQAPGKGLEWVSAISGSGGSTYY    60
ADSVKGRFTISRDNSKNTLYLQMNSLRAEDTAVYYCARVRGDYRTDIWGRGTLVTVSS     118
```

FIGURE 1H

AM_H17 polynucleotide sequence (SEQ ID:51)

```
gaggtgcagctgttggagtctggggggaggcttggtacagcctggggggtccctgagactc      60
 E   V   Q   L   L   E   S   G   G   G   L   V   Q   P   G   G   S   L   R   L
tcctgtgcagcctctagattcacctttagcagctatgccatgagctgggtccgccaggct      120
 S   C   A   A   S   R   F   T   F   S   S   Y   A   M   S   W   V   R   Q   A
ccagggaaggggctggagtgggtctcagctattagtggtagtggtggtagcacatactac      180
 P   G   K   G   L   E   W   V   S   A   I   S   G   S   G   G   S   T   Y   Y
gcagactccgtgaagggccggttcaccatctccagagacaattccaagaacacgctgtat      240
 A   D   S   V   K   G   R   F   T   I   S   R   D   N   S   K   N   T   L   Y
ctgcaaatgaacagcctgagagccgaggacacggccgtgtattactgtgcgagagttcgg      300
 L   Q   M   N   S   L   R   A   E   D   T   A   V   Y   Y   C   A   R   V   R
ggcatatacggtatggacgtctggggccggggaaccctg                          339
 G   I   Y   G   M   D   V   W   G   R   G   T   L
```

AM_H17 amino acid sequence (SEQ ID:17)

```
EVQLLESGGGLVQPGGSLRLSCAASRFTFSSYAMSWVRQAPGKGLEWVSAISGSGGSTYY      60
ADSVKGRFTISRDNSKNTLYLQMNSLRAEDTAVYYCARVRGIYGMDVWGRGTL             113
```

AM_L1 polynucleotide sequence (SEQ ID:52)

```
cagcctgtgctgactcagccccctcagtgtccgtgtcccaggacagactgccagcatc       60
 Q   P   V   L   T   Q   P   P   S   V   S   V   S   P   G   Q   T   A   S   I
acctgctctggagataaattgggggataaatatgcttcctggtatcagcagaagccaggc      120
 T   C   S   G   D   K   L   G   D   K   Y   A   S   W   Y   Q   Q   K   P   G
aagtcccctgtactggtcatctatcaagattccaatcggccctcagggatccctgagcga    180
 K   S   P   V   L   V   I   Y   Q   D   S   N   R   P   S   G   I   P   E   R
ttctctggctccaactctgggaacacagccactctgaccatcagcgggacccaggctagg    240
 F   S   G   S   N   S   G   N   T   A   T   L   T   I   S   G   T   Q   A   R
gatgaggctgactattactgtcaggcgtgggacagcagcactgcatcggtgttcggcgga    300
 D   E   A   D   Y   Y   C   Q   A   W   D   S   S   T   A   S   V   F   G   G
gggaccaag                                                        309
 G   T   K
```

AM_L1 amino acid sequence (SEQ ID:18)

```
QPVLTQPPSVSVSPGQTASITCSGDKLGDKYASWYQQKPGKSPVLVIYQDSNRPSGIPER     60
FSGSNSGNTATLTISGTQARDEADYYCQAWDSSTASVFGGGTK                       103
```

FIGURE 1I

AM_L2 polynucleotide sequence (SEQ ID:53)

```
cagcctgtgctgactcagccccctcagtgtccgtgtccccaggacagactgccagcatc    60
 Q  P  V  L  T  Q  P  P  S  V  S  V  S  P  G  Q  T  A  S  I
acctgctctggagataaattgggggataaatatgcttcctggtatcagcagaagccaggc   120
 T  C  S  G  D  K  L  G  D  K  Y  A  S  W  Y  Q  Q  K  P  G
aagtcccctgtactggtcatctatcaagattccaatcggccctcagggatccctgagcga   180
 K  S  P  V  L  V  I  Y  Q  D  S  N  R  P  S  G  I  P  E  R
ttctctggctccaactctgggaacacagccactctgaccatcagcgggacccaggctagg   240
 F  S  G  S  N  S  G  N  T  A  T  L  T  I  S  G  T  Q  A  R
gatgaggctgactattactgtcaggcgtgggaccactccttgcagcacaggttcggcgga   300
 D  E  A  D  Y  Y  C  Q  A  W  D  H  S  L  Q  H  R  F  G  G
gggaccaaggtcaccgtcctaggt                                        324
 G  T  K  V  T  V  L  G
```

AM_L2 amino acid sequence (SEQ ID:19)

```
QPVLTQPPSVSVSPGQTASITCSGDKLGDKYASWYQQKPGKSPVLVIYQDSNRPSGIPER    60
FSGSNSGNTATLTISGTQARDEADYYCQAWDHSLQHRFGGGTKVTVLG               108
```

AM_L3 polynucleotide sequence (SEQ ID:54)

```
cagcctgtgctgactcagccccctcagtgtccgtgtccccaggacagactgccagcatc    60
 Q  P  V  L  T  Q  P  P  S  V  S  V  S  P  G  Q  T  A  S  I
acctgctctggagataaattgggggataaatatgcttcctggtatcagcagaagccaggc   120
 T  C  S  G  D  K  L  G  D  K  Y  A  S  W  Y  Q  Q  K  P  G
cagacccctgtactggtcatctatcaagattccaatcggccctcagggatccctgagcga   180
 Q  T  P  V  L  V  I  Y  Q  D  S  N  R  P  S  G  I  P  E  R
ttctctggctccaactccgggaacacagccactctgaccatcagcgggacccaggctagg   240
 F  S  G  S  N  S  G  N  T  A  T  L  T  I  S  G  T  Q  A  R
gatgaggctgactattactgtcaggcgtggaccagcgccctgaactcgcagttcggcgga   300
 D  E  A  D  Y  Y  C  Q  A  W  T  S  A  L  N  S  Q  F  G  G
gggaccaaggtcaccgtcctaggt                                        324
 G  T  K  V  T  V  L  G
```

AM_L3 amino acid sequence (SEQ ID:20)

```
QPVLTQPPSVSVSPGQTASITCSGDKLGDKYASWYQQKPGQTPVLVIYQDSNRPSGIPER    60
FSGSNSGNTATLTISGTQARDEADYYCQAWTSALNSQFGGGTKVTVLG               108
```

FIGURE 1J

AM<sub>L</sub>4 polynucleotide sequence (SEQ ID:55)

```
cagcctgtgctgactcagccccctcagtgtccgtgtccccaggacagactgccagcatc     60
 Q  P  V  L  T  Q  P  P  S  V  S  V  S  P  G  Q  T  A  S  I
acctgctctggagataaattgggggataaatatgcttcctggtatcagcagaagccaggc    120
 T  C  S  G  D  K  L  G  D  K  Y  A  S  W  Y  Q  Q  K  P  G
cagtcccctgtactggtcatctatcaagattccaatcggccctcagggatccctgagcga   180
 Q  S  P  V  L  V  I  Y  Q  D  S  N  R  P  S  G  I  P  E  R
ttctctggctccaactctggggacacagccactctgaccatcagcgggacccaggctagg   240
 F  S  G  S  N  S  G  D  T  A  T  L  T  I  S  G  T  Q  A  R
gatgaggctgactattactgtcaggcgtggacgcactccctcagcacgttgttcggcgga   300
 D  E  A  D  Y  Y  C  Q  A  W  T  H  S  L  S  T  L  F  G  G
gggaccaaggtcaccgtcctaggt                                       324
 G  T  K  V  T  V  L  G
```

AM<sub>L</sub>4 amino acid sequence (SEQ ID:21)

```
QPVLTQPPSVSVSPGQTASITCSGDKLGDKYASWYQQKPGQSPVLVIYQDSNRPSGIPER     60
FSGSNSGDTATLTISGTQARDEADYYCQAWTHSLSTLFGGGTKVTVLG                108
```

AM<sub>L</sub>5 polynucleotide sequence (SEQ ID:56)

```
tcctatgagctgactcagccccctcagtgtccgtgtccccaggacagactgccagcatc     60
 S  Y  E  L  T  Q  P  P  S  V  S  V  S  P  G  Q  T  A  S  I
acctgctctggagataaattgggggataaatatgcttcctggtatcagcagaagccaggc    120
 T  C  S  G  D  K  L  G  D  K  Y  A  S  W  Y  Q  Q  K  P  G
cagtcccctgtactggtcatctatcaagattccaatcggccctcagggatccctgagcga   180
 Q  S  P  V  L  V  I  Y  Q  D  S  N  R  P  S  G  I  P  E  R
ttctctggctccaactctgggaacacagccactctgaccatcagcgggacccaggctatg   240
 F  S  G  S  N  S  G  N  T  A  T  L  T  I  S  G  T  Q  A  M
gatgaggctgactattactgtcaggcgtggacccacagcctgagcacgttgttcggcgga   300
 D  E  A  D  Y  Y  C  Q  A  W  T  H  S  L  S  T  L  F  G  G
gggaccaagctgaccgtcctaggt                                       324
 G  T  K  L  T  V  L  G
```

AM<sub>L</sub>5 amino acid sequence (SEQ ID:22)

```
SYELTQPPSVSVSPGQTASITCSGDKLGDKYASWYQQKPGQSPVLVIYQDSNRPSGIPER     60
FSGSNSGNTATLTISGTQAMDEADYYCQAWTHSLSTLFGGGTKLTVLG                108
```

FIGURE 1K

AM$_L$6 polynucleotide sequence (SEQ ID:57)

```
cagtctgtgctgactcagccaccctcagcgtctgggaccccgggcagagggtcaccatc    60
 Q  S  V  L  T  Q  P  P  S  A  S  G  T  P  G  Q  R  V  T  I
tcttgttctggaaggaactccaacatcggaagttatactgtaacctggtaccagcagctc   120
 S  C  S  G  R  N  S  N  I  G  S  Y  T  V  T  W  Y  Q  Q  L
ccaggaacggccccaaactcctcatctatagtaatagtcagcggccctcaggggtccct    180
 P  G  T  A  P  K  L  L  I  Y  S  N  S  Q  R  P  S  G  V  P
gaccgattctcaggctccaagtctggcacctcagcctccttggccatcagtgggctccag   240
 D  R  F  S  G  S  K  S  G  T  S  A  S  L  A  I  S  G  L  Q
tctgaagatgaggctgattattactgtgcagcatgggatgacagcctgaatggcccggtg   300
 S  E  D  E  A  D  Y  Y  C  A  A  W  D  D  S  L  N  G  P  V
ttcggcggagggaccaag                                             318
 F  G  G  G  T  K
```

AM$_L$6 amino acid sequence (SEQ ID:23)

```
QSVLTQPPSASGTPGQRVTISCSGRNSNIGSYTVTWYQQLPGTAPKLLIYSNSQRPSGVP    60
DRFSGSKSGTSASLAISGLQSEDEADYYCAAWDDSLNGPVFGGGTK                 106
```

AM$_L$7 polynucleotide sequence (SEQ ID:58)

```
cagtctgtgctgactcagccaccctcagcgtctgggaccccgggcagagggtcaccatc    60
 Q  S  V  L  T  Q  P  P  S  A  S  G  T  P  G  Q  R  V  T  I
tcttgttctggaaggaactccaacatcggaagttatactgtaacctggtaccagcagctc   120
 S  C  S  G  R  N  S  N  I  G  S  Y  T  V  T  W  Y  Q  Q  L
ccaggaacggccccaaactcctcatctatagtaatagtcagcggccctcaggggtccct    180
 P  G  T  A  P  K  L  L  I  Y  S  N  S  Q  R  P  S  G  V  P
gaccgattctcaggctccaagtctggcacctcagcctccttggccatcagtgggctccag   240
 D  R  F  S  G  S  K  S  G  T  S  A  S  L  A  I  S  G  L  Q
tctgaagatgaggctgattattactgtgtggtgtgggatgacgtgctgaatggcccggtg   300
 S  E  D  E  A  D  Y  Y  C  V  V  W  D  D  V  L  N  G  P  V
ttcggcggagggaccaagctgaccgtcctaggt                              333
 F  G  G  G  T  K  L  T  V  L  G
```

AM$_L$7 amino acid sequence (SEQ ID:24)

```
QSVLTQPPSASGTPGQRVTISCSGRNSNIGSYTVTWYQQLPGTAPKLLIYSNSQRPSGVP    60
DRFSGSKSGTSASLAISGLQSEDEADYYCVVWDDVLNGPVFGGGTKLTVLG            111
```

FIGURE 1L

AM_L 8 polynucleotide sequence (SEQ ID:59)

```
cagtctgtgctgactcagccaccctcagcgtctgggaccccgggcagagggtcaccatc     60
 Q  S  V  L  T  Q  P  P  S  A  S  G  T  P  G  Q  R  V  T  I
tcttgttctggaaggaactccaacatcggaagttatactgtaacctggtaccagcagctc    120
 S  C  S  G  R  N  S  N  I  G  S  Y  T  V  T  W  Y  Q  Q  L
ccaggaacggcccccaaactcctcatctatagtaatagtcagcggccctcagggtccct    180
 P  G  T  A  P  K  L  L  I  Y  S  N  S  Q  R  P  S  G  V  P
gaccgattctcaggctccaagtctggcacctcagcctccttggccatcagtgggctccag    240
 D  R  F  S  G  S  K  S  G  T  S  A  S  L  A  I  S  G  L  Q
tctgaagatgaggctgattattactgtgtcgtgtgggatgacaagctgaatggcccggtg    300
 S  E  D  E  A  D  Y  Y  C  V  V  W  D  D  K  L  N  G  P  V
ttcggcggagggaccaagctgaccgtcctaggt                               333
 F  G  G  G  T  K  L  T  V  L  G
```

AM_L 8 polynucleotide sequence (SEQ ID:25)

```
QSVLTQPPSASGTPGQRVTISCSGRNSNIGSYTVTWYQQLPGTAPKLLIYSNSQRPSGVP     60
DRFSGSKSGTSASLAISGLQSEDEADYYCVVWDDKLNGPVFGGGTKLTVLG             111
```

AM_L 9 polynucleotide sequence (SEQ ID:60)

```
cagtctgtgctgactcagccaccctcagcgtctgggaccccgggcagagggtcaccatc     60
 Q  S  V  L  T  Q  P  P  S  A  S  G  T  P  G  Q  R  V  T  I
tcttgttctggaaggaactccaacatcggaagttatactgtaacctggtaccagcagctc    120
 S  C  S  G  R  N  S  N  I  G  S  Y  T  V  T  W  Y  Q  Q  L
ccaggaacggcccccaaactcctcatctatagtaatagtcagcggccctcagggtccct    180
 P  G  T  A  P  K  L  L  I  Y  S  N  S  Q  R  P  S  G  V  P
gaccgattctcaggctccaagtctggcacctcagcctccttggccatcagtgggctccag    240
 D  R  F  S  G  S  K  S  G  T  S  A  S  L  A  I  S  G  L  Q
tctgaagatgaggctgattattactgtgtggtgtgggacgagatcctgaatggcccggtg    300
 S  E  D  E  A  D  Y  Y  C  V  V  W  D  E  I  L  N  G  P  V
ttcggcggagggaccaagctgaccgtcctaggt                               333
 F  G  G  G  T  K  L  T  V  L  G
```

AM_L 9 amino acid sequence (SEQ ID:26)

```
QSVLTQPPSASGTPGQRVTISCSGRNSNIGSYTVTWYQQLPGTAPKLLIYSNSQRPSGVP     60
DRFSGSKSGTSASLAISGLQSEDEADYYCVVWDEILNGPVFGGGTKLTVLG             111
```

FIGURE 1M

AM$_L$10 polynucleotide sequence (SEQ ID:61)

```
tcgtctgagctgactcaggaccctgctgtgtctgtggccttgggacagacagtcaggatc      60
 S   S   E   L   T   Q   D   P   A   V   S   V   A   L   G   Q   T   V   R   I
acatgccaaggagacagcctcagaagctattatgcaagctggtaccagcagaagccagga      120
 T   C   Q   G   D   S   L   R   S   Y   Y   A   S   W   Y   Q   Q   K   P   G
caggcccctgtacttgtcatctctgctaaaaacaaccggccctcagggatcccagaccga     180
 Q   A   P   V   L   V   I   S   A   K   N   N   R   P   S   G   I   P   D   R
ttctctggctccagctcaggaaacacagcttccttgaccatcactggggctcaggcggaa     240
 F   S   G   S   S   S   G   N   T   A   S   L   T   I   T   G   A   Q   A   E
gatgaagctgactattactgtaactcccgggacagcagtaaccatgtggtattcggcgga     300
 D   E   A   D   Y   Y   C   N   S   R   D   S   S   N   H   V   V   F   G   G
gggaccaag                                                         309
 G   T   K
```

AM$_L$10 amino acid sequence (SEQ ID:27)

```
SSELTQDPAVSVALGQTVRITCQGDSLRSYYASWYQQKPGQAPVLVISAKNNRPSGIPDR       60
FSGSSSGNTASLTITGAQAEDEADYYCNSRDSSNHVVFGGGTK                       103
```

AM$_L$11 polynucleotide sequence (SEQ ID:62)

```
cagtctgtgctgactcagccaccctcagcgtctgggaccccgggcagagggtcaccatc       60
 Q   S   V   L   T   Q   P   P   S   A   S   G   T   P   G   Q   R   V   T   I
tcttgttctggaaggaactccaacatcggaagttatactgtaacctggtaccagcagctc     120
 S   C   S   G   R   N   S   N   I   G   S   Y   T   V   T   W   Y   Q   Q   L
ccaggaacggccccccaaactcctcatctatagtaatagtcagcggccctcaggggtccct    180
 P   G   T   A   P   K   L   L   I   Y   S   N   S   Q   R   P   S   G   V   P
gaccgattctcaggctccaagtctggcacctcagcctccttggccatcagtgggctccag    240
 D   R   F   S   G   S   K   S   G   T   S   A   S   L   A   I   S   G   L   Q
tctgaagatgaggctgattattactgtctcgtgtgggacgacgtcctgaatggcccggtg    300
 S   E   D   E   A   D   Y   Y   C   L   V   W   D   D   V   L   N   G   P   V
ttcggcggagggaccaagctgaccgtcctaggt                                 333
 F   G   G   G   T   K   L   T   V   L   G
```

AM$_L$11 amino acid sequence (SEQ ID:28)

```
QSVLTQPPSASGTPGQRVTISCSGRNSNIGSYTVTWYQQLPGTAPKLLIYSNSQRPSGVP       60
DRFSGSKSGTSASLAISGLQSEDEADYYCLVWDDVLNGPVFGGGTKLTVLG               111
```

FIGURE 1N

AM_L12 polynucleotide sequence (SEQ ID:63)

```
tcgtctgagctgactcaggaccctgctgtgtctgtggccttgggacagacagtcaggatc    60
 S  S  E  L  T  Q  D  P  A  V  S  V  A  L  G  Q  T  V  R  I
acatgccaaggagacagcctcagaagctattatgcaagctggtaccagcagaagccagga   120
 T  C  Q  G  D  S  L  R  S  Y  Y  A  S  W  Y  Q  Q  K  P  G
caggcccctgtacttgtcatctctgctaaaaacaaccggccctcagggatcccagaccga   180
 Q  A  P  V  L  V  I  S  A  K  N  N  R  P  S  G  I  P  D  R
ttctctggctccagctcaggaaacacagcttccttgaccatcactggggctcaggcggaa   240
 F  S  G  S  S  S  G  N  T  A  S  L  T  I  T  G  A  Q  A  E
gatgaggctgactattactgtgcgtcccggaacggctggaaccatgtggtattcggcgga   300
 D  E  A  D  Y  Y  C  A  S  R  N  G  W  N  H  V  V  F  G  G
gggaccaagctgaccgtcctaggt                                       324
 G  T  K  L  T  V  L  G
```

AM_L12 amino acid sequence (SEQ ID:29)

```
SSELTQDPAVSVALGQTVRITCQGDSLRSYYASWYQQKPGQAPVLVISAKNNRPSGIPDR    60
FSGSSSGNTASLTITGAQAEDEADYYCASRNGWNHVVFGGGTKLTVLG              108
```

AM_L13 polynucleotide sequence (SEQ ID:64)

```
tcgtctgagctgactcaggaccctgctgtgtctgtggccttgggacagacagtcagggtc    60
 S  S  E  L  T  Q  D  P  A  V  S  V  A  L  G  Q  T  V  R  V
acatgccaaggagacagcctcagaagctattatgcaagctggtaccagcagaagccagga   120
 T  C  Q  G  D  S  L  R  S  Y  Y  A  S  W  Y  Q  Q  K  P  G
caggcccctgtacttgtcatctctgctaaaaacaaccggccctcagggatcccagaccga   180
 Q  A  P  V  L  V  I  S  A  K  N  N  R  P  S  G  I  P  D  R
ttctctggctccagctcaggaaacacagcttccttgaccatcactggggctcaggcggaa   240
 F  S  G  S  S  S  G  N  T  A  S  L  T  I  T  G  A  Q  A  E
gatgaggctgactattactgtgcgtcccggaacggctggaaccatgtggtattcggcgga   300
 D  E  A  D  Y  Y  C  A  S  R  N  G  W  N  H  V  V  F  G  G
gggaccaagctgaccgtcctaggt                                       324
 G  T  K  L  T  V  L  G
```

AM_L13 amino acid sequence (SEQ ID:30)

```
SSELTQDPAVSVALGQTVRVTCQGDSLRSYYASWYQQKPGQAPVLVISAKNNRPSGIPDR    60
FSGSSSGNTASLTITGAQAEDEADYYCASRNGWNHVVFGGGTKLTVLG              108
```

FIGURE 10

AM$_L$14 polynucleotide sequence (SEQ ID:65)

```
tcgtctgagctgactcaggaccctgctgtgtctgtggccttgggacagacagtcaggatc    60
 S  S  E  L  T  Q  D  P  A  V  S  V  A  L  G  Q  T  V  R  I
acatgccaaggagacagcctcagaagctattatgcaagctggtaccagcagaagccagga   120
 T  C  Q  G  D  S  L  R  S  Y  Y  A  S  W  Y  Q  Q  K  P  G
caggcccctgtacttgtcatctctgctaaaaacaaccggccctcagggatcccagaccga   180
 Q  A  P  V  L  V  I  S  A  K  N  N  R  P  S  G  I  P  D  R
ttctctggctccagctcaggaaacacagcttccttgaccatcactggggctcaggcggaa   240
 F  S  G  S  S  S  G  N  T  A  S  L  T  I  T  G  A  Q  A  E
gatgaggctgactattactgtgcgtcccggaacggctggaaccatgtggtattcggcgga   300
 D  E  A  D  Y  Y  C  A  S  R  N  G  W  N  H  V  V  F  G  G
gggaccaagctgaccgtcctaggt                                        324
 G  T  K  L  T  V  L  G
```

AM$_L$14 amino acid sequence (SEQ ID:31)

```
SSELTQDPAVSVALGQTVRITCQGDSLRSYYASWYQQKPGQAPVLVISAKNNRPSGIPDR     60
FSGSSSGNTASLTITGAQAEDEADYYCASRNGWNHVVFGGGTKLTVLG               108
```

AM$_L$15 polynucleotide sequence (SEQ ID:66)

```
tcgtctgagctgactcaggaccctgctgtgtctgtggccttgggacagacagtcagggtc    60
 S  S  E  L  T  Q  D  P  A  V  S  V  A  L  G  Q  T  V  R  V
acatgccaaggagacagcctcagaagctattatgcaagctggtaccagcagaagccagga   120
 T  C  Q  G  D  S  L  R  S  Y  Y  A  S  W  Y  Q  Q  K  P  G
caggcccctgtacttgtcatctctgctaaaaacaaccggccctcagggatcccagaccga   180
 Q  A  P  V  L  V  I  S  A  K  N  N  R  P  S  G  I  P  D  R
ttctctggctccagctcaggaaacacagcttccttgaccatcactggggctcaggcggaa   240
 F  S  G  S  S  S  G  N  T  A  S  L  T  I  T  G  A  Q  A  E
gatgaggctgactattactgtgcgtcccggaacggctggaaccatgtggtattcggcgga   300
 D  E  A  D  Y  Y  C  A  S  R  N  G  W  N  H  V  V  F  G  G
gggaccaagctgaccgtcctaggt                                        324
 G  T  K  L  T  V  L  G
```

AM$_L$15 amino acid sequence (SEQ ID:32)

```
SSELTQDPAVSVALGQTVRVTCQGDSLRSYYASWYQQKPGQAPVLVISAKNNRPSGIPDR     60
FSGSSSGNTASLTITGAQAEDEADYYCASRNGWNHVVFGGGTKLTVLG               120
```

FIGURE 1P

AM$_L$16 polynucleotide sequence (SEQ ID:67)

```
tcgtctgagctgactcaggaccctgctgtgtctgtggccttgggacagacagtcaggatc    60
 S  S  E  L  T  Q  D  P  A  V  S  V  A  L  G  Q  T  V  R  I
acatgccaaggagacagcctcagaagctattatgcaagctggtaccagcagaagccagga    120
 T  C  Q  G  D  S  L  R  S  Y  Y  A  S  W  Y  Q  Q  K  P  G
caggcccctgtacttgtcatctctgctaaaaacaaccggccctcagggatcccagaccga    180
 Q  A  P  V  L  V  I  S  A  K  N  N  R  P  S  G  I  P  D  R
ttctctggctccagctcaggaaacacagcttccttgaccatcactggggctcaggcggaa    240
 F  S  G  S  S  S  G  N  T  A  S  L  T  I  T  G  A  Q  A  E
gatgaggctgactattactgtgcgacccggaacggctggaaccatgtggtattcggcgga    300
 D  E  A  D  Y  Y  C  A  T  R  N  G  W  N  H  V  V  F  G  G
gggaccaagctgaccgtcctaggt                                        324
 G  T  K  L  T  V  L  G
```

AM$_L$16 amino acid sequence (SEQ ID:33)

```
SSELTQDPAVSVALGQTVRITCQGDSLRSYYASWYQQKPGQAPVLVISAKNNRPSGIPDR    60
FSGSSSGNTASLTITGAQAEDEADYYCATRNGWNHVVFGGGTKLTVLG                108
```

AM$_L$17 polynucleotide sequence (SEQ ID:68)

```
tcgtctgagctgactcaggaccctgctgtgtctgtggccttgggacagacagtcagggtc    60
 S  S  E  L  T  Q  D  P  A  V  S  V  A  L  G  Q  T  V  R  V
acatgccaaggagacagcctcagaagctattatgcaagctggtaccagcagaagccagga    120
 T  C  Q  G  D  S  L  R  S  Y  Y  A  S  W  Y  Q  Q  K  P  G
caggcccctgtacttgtcatctctgctaaaaacaaccggccctcagggatcccagaccga    180
 Q  A  P  V  L  V  I  S  A  K  N  N  R  P  S  G  I  P  D  R
ttctctggctccagctcaggaaacacagcttccttgaccatcactggggctcaggcggaa    240
 F  S  G  S  S  S  G  N  T  A  S  L  T  I  T  G  A  Q  A  E
gatgaggctgactattactgtgcgacccggaacggctggaaccatgtggtattcggcgga    300
 D  E  A  D  Y  Y  C  A  T  R  N  G  W  N  H  V  V  F  G  G
gggaccaagctgaccgtcctaggt                                        324
 G  T  K  L  T  V  L  G
```

AM$_L$17 amino acid sequence (SEQ ID:34)

```
SSELTQDPAVSVALGQTVRVTCQGDSLRSYYASWYQQKPGQAPVLVISAKNNRPSGIPDR    60
FSGSSSGNTASLTITGAQAEDEADYYCATRNGWNHVVFGGGTKLTVLG                108
```

FIGURE 1Q

AM_H1 amino acid sequence (SEQ ID:1)

QVQLVQSGGGVVQPGRSLRLSCAASGFTFSSGYGMHWVRQAPGKGLEWVAVISNDGSKKYYSDSVKGRFTISRDNSKNTLYLQMNSLRAEDTAVYYCAKGSSSIWLIQSLDHWGQGTTVTVSS
　　　　　　　　　　　　　　CDR1　　　　　　　　　　　CDR2　　　　　　　　　　　　　　　　　　　　　　　CDR3

AM_H2 amino acid sequence (SEQ ID NO:2)

EVQLVESGGGVVQPGRSLRLSCAASGFTFSSGYGMHWVRQAPGKGLEWVAVISNDGSKKYYSDSVKGRFTISRDNSKNTLYLQMNSLRAEDTAVYYCAKGSSSIWLIQSLDHWGQGTTVTVSS
　　　　　　　　　　　　　　CDR1　　　　　　　　　　　CDR2　　　　　　　　　　　　　　　　　　　　　　　CDR3

AM_H3 amino acid sequence (SEQ ID NO:3)

QVQLVQSGGGVVQPGRSLRLSCAASGFTFSSGYGMHWVRQAPGKGLEWVAVISNDGSKKYYSDSVKGRFTISRDNSKNTLYLQMNSLRAEDTAVYYCAKGSSSIWLSQSLDGWGQGTTVTVSS
　　　　　　　　　　　　　　CDR1　　　　　　　　　　　CDR2　　　　　　　　　　　　　　　　　　　　　　　CDR3

AM_H4 amino acid sequence (SEQ ID:4)

EVQLVESGGGVVQPGRSLRLSCAASGFTFSSGYGMHWVRQAPGKGLEWVAVISNDGSKKYYSDSVKGRFTISRDNSKNTLYLQMNSLRAEDTAVYYCAKGSSSIWLSQSLDGWGQGTTVTVSS
　　　　　　　　　　　　　　CDR1　　　　　　　　　　　CDR2　　　　　　　　　　　　　　　　　　　　　　　CDR3

AM_H5 amino acid sequence (SEQ ID:5)

QVQLVQSGGGVVQPGRSLRLSCAASGFTFSSGYGMHWVRQAPGKGLEWVAVISNDGSKKYYSDSVKGRFTISRDNSKNTLYLQMNSLRAEDTAVYYCAKGSSSIWLTSALNLWGQGTTVTVSS
　　　　　　　　　　　　　　CDR1　　　　　　　　　　　CDR2　　　　　　　　　　　　　　　　　　　　　　　CDR3

AM_H6 polynucleotide sequence (SEQ ID:6)

EVQLVESGGGVVQPGRSLRLSCAASGFTFSSGYGMHWVRQAPGKGLEWVAVISNDGSKKYYSDSVKGRFTISRDNSKNTLYLQMNSLRAEDTAVYYCAKGSSSIWLTSALNLWGQGTTVTVSS
　　　　　　　　　　　　　　CDR1　　　　　　　　　　　CDR2　　　　　　　　　　　　　　　　　　　　　　　CDR3

AM_H7 amino acid sequence (SEQ ID:7)

EVQLVESGGGVVQPGRSLRLSCAASGFTFSSGYGMHWVRQAPGKGLEWVAVISNDGSKKYYSDSVKGRFTISRDNSKNTLYLQMNSLRAEDTAIYYCAKGSSSIWFGETVDIWGQGTT
　　　　　　　　　　　　　　CDR1　　　　　　　　　　　CDR2　　　　　　　　　　　　　　　　　　　　　　　CDR3

FIGURE 2A

AM_H8 polynucleotide sequence (SEQ ID:8)

QVQLVQSGAEVKKPGASVKVSCKVSGYTLTELSMHWVRQAPGKGLEWMGGFDREDDETIHAQKFQGRVTMTEDTSTDTAYMELSSLRSEDTAVYYCATDLMYMGDFWIQHWGQGTLVTVSS
                            CDR1                   CDR2                           CDR3

AM_H9 amino acid sequence (SEQ ID:9)

QVQLVQSGAEVKKPGASVKVSCKVSGYTLTELSMHWVRQAPGKGLEWMGGFDREDDETIHAQKFQGRVTMTEDTSTDTAYMELSSLRSEDTAVYYCATDLMYMGDFWIQHWGQGTLVTVSS
                            CDR1                   CDR2                           CDR3

AM_H10 amino acid sequence (SEQ ID:10)

QVQLVQSGAEVKKPGASVKVSCKVSGYTLTELSMHWVRQAPGKGLEWMGGFDREDDETIHAQKFQGRVTMTEDTSTDTAYMELSSLRSEDTAVYYCATDLMAWDYEPIQHWGQGTLVTVSS
                            CDR1                   CDR2                           CDR3

AM_H11 amino acid sequence (SEQ ID:11)

QVQLVQSGAEVKKPGASVKVSCKVSGYTLTELSMHWVRQAPGKGLEWMGGFDREDDETIHAQKFQGRVTMTEDTSTDTAYMELSSLRSEDTAVYYCATDLMVWNPPIQHWGQGTLVTVSS
                            CDR1                   CDR2                           CDR3

AM_H12 amino acid sequence (SEQ ID:12)

QVQLVQSGAEVKKPGASVKVSCKVSGYTLTELSMHWVRQAPGKGLEWMGGFDREDDETIHAQKFQGRVTMTEDTSTDTAYMELSSLRSEDTAVYYCATDLMVWGDFWIQHWGKGTM
                            CDR1                   CDR2                           CDR3

AM_H13 amino acid sequence (SEQ ID:13)

EVQLLESGGGLVQPGGSLRLSCAASGFTPSSYAMSWVRQAPGKGLEWVSAISGSGGGTYYADSVKGRFTISRDNSKNTLYLQMNSLRAEDTAVYYCARIRGDYRIDINGQGTLVTVSS
                            CDR1                   CDR2                           CDR3

AM_H14 amino acid sequence (SEQ ID:14)

EVQLLESGGGLVQPGGSLRLSCAASGFTPSSYAMSWVRQAPGKGLEWVSAISGSGSGTYYADSVKGRSTIRDNSKNTLYLQMNSLRAEDTAVYYCARIRGDYRIDINGRGTLVTVSS
                            CDR1                   CDR2                           CDR3

FIGURE 2B

AM$_H$15 amino acid sequence (SEQ ID:15)

EVQLLESGGGLAQPGGSLRLSCAASGFTFSSYAMSWVRQAPGKGLEWVSAISGSGSTYYADSVKGRFTISRDNSKNTLYLQMNSLRAEDTAVYYCARVRGDYRTDIWGRGTLVTVSS
　　　　　　　　　　　　　　　　　CDR1　　　　　　　　　CDR2　　　　　　　　　　　　　　　　　　　　　　　　　　　CDR3

AM$_H$16 amino acid sequence (SEQ ID:16)

EVQLLESGGGLVQPGGSLRLSCAASRFTFSSYAMSWVRQAPGKGLEWVSAISGSGSTYYADSVKGRFTISRDNSKNTLYLQMNSLRAEDTAVYYCARVRGDYRTDIWGRGTLVTVSS
　　　　　　　　　　　　　　　　　CDR1　　　　　　　　　CDR2　　　　　　　　　　　　　　　　　　　　　　　　　　　CDR3

AM$_H$17 amino acid sequence (SEQ ID:17)

EVQLLESGGGLVQPGGSLRLSCAASRFTFSSYAMSWVRQAPGKGLEWVSAISGSGSTYYADSVKGRFTISRDNSKNTLYLQMNSLRAEDTAVYYCARVRGIYGMDVNGRGTL
　　　　　　　　　　　　　　　　　CDR1　　　　　　　　　CDR2　　　　　　　　　　　　　　　　　　　　　　　　　CDR3

AM$_L$1 amino acid sequence (SEQ ID:18)

QPVLTQPSVSVSPGQTASITCSGDKLGDKYASWYQQKPGKSPVLVIYQDSNRPSGIPERFSGSNSGNTATLTISGTQARDEADYYCQAMDSSTASVFGGGTK
　　　　　　　　　　　　　CDR1　　　　　　　　　　CDR2　　　　　　　　　　　　　　　　　　　　　　　CDR3

AM$_L$2 amino acid sequence (SEQ ID:19)

QPVLTQPPSVSVSPGQTASITCSGDKLGDKYASWYQQKPGKSPVLVIYQDSNRPSGIPERFSGSNSGNTATLTISGTQARDEADYYCQAMDHSLQHRFGGGTKVTVLG
　　　　　　　　　　　　　CDR1　　　　　　　　　　CDR2　　　　　　　　　　　　　　　　　　　　　　　　CDR3

AM$_L$3 amino acid sequence (SEQ ID:20)

QPVLTQPPSVSVSPGQTASITCSGDKLGDKYASWYQQKPGQTPVLVIYQDSNRPSGIPERFSGSNSGNTATLTISGTQARDEADYYCQANTSAINSQFGGGTKVTVLG
　　　　　　　　　　　　　CDR1　　　　　　　　　　CDR2　　　　　　　　　　　　　　　　　　　　　　　　CDR3

AM$_L$4 amino acid sequence (SEQ ID:21)

QPVLTQPPSVSVSPGQTASITCSGDKLGDKYASWYQQKPGQSPVLVIYTDSNRPSGIPERFSGSNSGDTATLTISGTQARDEADYYCQAWTHSLSTLFGGGTKVTVLG
　　　　　　　　　　　　　CDR1　　　　　　　　　　CDR2　　　　　　　　　　　　　　　　　　　　　　　　CDR3

FIGURE 2C

AM_L5 amino acid sequence (SEQ ID:22)

SYELTQPPSVSVSPGQTASITC SGDALGDKYAS WYQQKPGQSPVLVIY QDSNRPSGI PERFSGSNSGNTATLTISGTQAMDEADYYC QAWTHSLSTL FGGGTKLTVLG
　　　　　　　　　　　　 CDR1　　　　　　　　　　　　　　　　 CDR2　　　　　　　　　　　　　　　　　　　　　　　　　　　　　　　　　　 CDR3

AM_L6 amino acid sequence (SEQ ID:23)

QSVLTQPPSASGTPGQRVTISC SGRNSNIGSYTVT WYQQLPGTAPKLLIY SNSQRPS GVPDRFSGSKSGTSASLAISGLQSEDEADYYC AAWDDSLNGPV FGGGTK
　　　　　　　　　　　　 CDR1　　　　　　　　　　　　　　　　 CDR2　　　　　　　　　　　　　　　　　　　　　　　　　　　　　　　　　　 CDR3

AM_L7 amino acid sequence (SEQ ID:24)

QSVLTQPPSASGTPGQRVTISC SGRNSNIGSYTVT WYQQLPGTAPKLLIY SNSQRPS GVPDRFSGSKSGTSASLAISGLQSEDEADYYC CVVMDDVLNGPV FGGGTKLTVLG
　　　　　　　　　　　　 CDR1　　　　　　　　　　　　　　　　 CDR2　　　　　　　　　　　　　　　　　　　　　　　　　　　　　　　　　　 CDR3

AM_L8 polynucleotide sequence (SEQ ID:25)

AM_L9 amino acid sequence (SEQ ID:26)

QSVLTQPPSASGTPGQRVTISC SGRNSNIGSYTVT WYQQLPGTAPKLLIY SNSQRPS GVPDRFSGSKSGTSASLAISGLQSEDEADYYC CVVMDDKLNGPV FGGGTKLTVLG
　　　　　　　　　　　　 CDR1　　　　　　　　　　　　　　　　 CDR2　　　　　　　　　　　　　　　　　　　　　　　　　　　　　　　　　　 CDR3

AM_L10 amino acid sequence (SEQ ID:27)

SSELTQDPAVSVALGQTVRITC QGDSLRSYYAS WYQQKPGQAPVLVIS AKNNRPSGI PDRFSGSSSGNTASLTITGAQAEDEADYYC NSRDSSNHYV FGGGTK
　　　　　　　　　　　　 CDR1　　　　　　　　　　　　　　　　 CDR2　　　　　　　　　　　　　　　　　　　　　　　　　　　　　　　　　　 CDR3

AM_L11 amino acid sequence (SEQ ID:28)

QSVLTQPPSASGTPGQRVTISC SGRNSNIGSYTVT WYQQLPGTAPKLLIY SNSQRPS GVPDRFSGSKSGTSASLAISGLQSEDEADYYC CVVMDDVLNGPV FGGGTKLTVLG
　　　　　　　　　　　　 CDR1　　　　　　　　　　　　　　　　 CDR2　　　　　　　　　　　　　　　　　　　　　　　　　　　　　　　　　　 CDR3

FIGURE 2D

AM₁12 amino acid sequence (SEQ ID:29)

SSELTQDPAVSVALGQTVRITCQGDSLRSYYASWYQQKPGQAPVLVISAKNNRPSGIPDRFSGSSSGNTASLTITGAQAEDEADYYCASRNGWNHVVFGGGTKLTVLG
　　　　　　　　　　　　　　　CDR1　　　　　　　　　　　　　CDR2　　　　　　　　　　　　　　　　　　　　　CDR3

AM₁13 amino acid sequence (SEQ ID:30)

SSELTQDPAVSVALGQTVRITCQGDSLRSYYASWYQQKPGQAPVLVISAKNNRPSGIPDRFSGSSSGNTASLTITGAQAEDEADYYCASRNGWNHVVFGGGTKLTVLG
　　　　　　　　　　　　　　　CDR1　　　　　　　　　　　　　CDR2　　　　　　　　　　　　　　　　　　　　　CDR3

AM₁14 amino acid sequence (SEQ ID:31)

SSELTQDPAVSVALGQTVRITCQGDSLRSYYASWYQQKPGQAPVLVISAKNNRPSGIPDRFSGSSSGNTASLTITGAQAEDEADYYCASRNGWNHVVFGGGTKLTVLG
　　　　　　　　　　　　　　　CDR1　　　　　　　　　　　　　CDR2　　　　　　　　　　　　　　　　　　　　　CDR3

AM₁15 amino acid sequence (SEQ ID:32)

SSELTQDPAVSVALGQTVRITCQGDSLRSYYASWYQQKPGQAPVLVISAKNNRPSGIPDRFSGSSSGNTASLTITGAQAEDEADYYCASRNGWNHVVFGGGTKLTVLG
　　　　　　　　　　　　　　　CDR1　　　　　　　　　　　　　CDR2　　　　　　　　　　　　　　　　　　　　　CDR3

AM₁16 amino acid sequence (SEQ ID:33)

SSELTQDPAVSVALGQTVRITCQGDSLRSYYASWYQQKPGQAPVLVISAKNNRPSGIPDRFSGSSSGNTASLTITGAQAEDEADYYCATRNGWNHVVFGGGTKLTVLG
　　　　　　　　　　　　　　　CDR1　　　　　　　　　　　　　CDR2　　　　　　　　　　　　　　　　　　　　　CDR3

AM₁17 amino acid sequence (SEQ ID:34)

SSELTQDPAVSVALGQTVRITCQGDSLRSYYASWYQQKPGQAPVLVISAKNNRPSGIPDRFSGSSSGNTASLTITGAQAEDEADYYCATRNGWNHVVFGGGTKLTVLG
　　　　　　　　　　　　　　　CDR1　　　　　　　　　　　　　CDR2　　　　　　　　　　　　　　　　　　　　　CDR3

FIGURE 2E

Heavy Chain

|  |  | 1 |  |  | CDR1 |  |  | CDR2 | 70 |
|---|---|---|---|---|---|---|---|---|---|
| AM_H1 | SEQ ID NO: 1 | QVQLVQSGGG | VVQPGRSLRL | SCAASGFTFS | GYGMHWVRQA | PGKGLEWVAV | ISNDGSKKYX | SDSVKGRFTI |
| AM_H2 | SEQ ID NO: 2 | EVQLVESGGG | VVQPGRSLRL | SCAASGFTFS | GYGMHWVRQA | PGKGLEWVAV | ISNDGSKKYY | SDSVKGRFTI |
| AM_H3 | SEQ ID NO: 3 | QVQLVQSGGG | VVQPGRSLRL | SCAASGFTFS | GYGMHWVRQA | PGKGLEWVAV | ISNDGSKKYY | SDSVKGRFTI |
| AM_H4 | SEQ ID NO: 4 | EVQLVESGGG | VVQPGRSLRL | SCAASGFTFS | GYGMHWVRQA | PGKGLEWVAV | ISNDGSKKYY | SDSVKGRFTI |
| AM_H5 | SEQ ID NO: 5 | EVQLVESGGG | VVQPGRSLRL | SCAASGFTFS | GYGMHWVRQA | PGKGLEWVAV | ISNDGSKKYY | SDSVKGRFTI |
| AM_H6 | SEQ ID NO: 6 | EVQLVESGGG | VVQPGRSLRL | SCAASGFTFS | GYGMHWVRQA | PGKGLEWVAV | ISNDGSKKYY | SDSVKGRFTI |
| AM_H15 | SEQ ID NO:15 | EVQLLESGGG | LAQPGGSLRL | SCAASGFTFS | SYAMSWVRQA | PGKGLEWVSA | ISGSGGSTYY | ADSVKGRFTI |
| AM_H16 | SEQ ID NO:16 | EVQLLESGGG | LVQPGGSLRL | SCAASRFTFS | SYAMSWVRQA | PGKGLEWVSA | ISGSGGSTYY | ADSVKGRFTI |
| AM_H13 | SEQ ID NO:13 | EVQLLESGGG | LVQPGGSLRL | SCAASGFTFS | SYAMSWVRQA | PGKGLEWVSA | ISGSGGGTYY | ADSVKGRFTI |
| AM_H14 | SEQ ID NO:14 | EVQLLESGGG | LVQPGGSLRL | SCAASGFTFS | SYAMSWVRQA | PGKGLEWVSA | ISGSGGGTYY | ADSVKGRSTI |
| AM_H8 | SEQ ID NO: 8 | QVQLVQSGAE | VKKPGASVKV | SCKVSGYTLT | ELSMHWVRQA | PGKGLEWMGG | FDREDDETIH | AQKFQGRVTM |
| AM_H9 | SEQ ID NO: 9 | QVQLVQSGAE | VKKPGASVKV | SCKVSGYTLT | ELSMHWVRQA | PGKGLEWMGG | FDREDDETIH | AQKFQGRVTM |
| AM_H10 | SEQ ID NO:10 | QVQLVQSGAE | VKKPGASVKV | SCKVSGYTLT | ELSMHWVRQA | PGKGLEWMGG | FDREDDETIH | AQKFQGRVTM |
| AM_H11 | SEQ ID NO:11 | QVQLVQSGGG | VVQPGRSLRL | SCAASGFTFS | GYGMHWVRQA | PGKGLEWVAV | ISNDGSKKYY | SDSVKGRFTI |
| AM_H7 | SEQ ID NO: 7 | EVQLVESGGG | VVQPGRSLRL | SCAASGFTFS | ELSMHWVRQA | PGKGLEWVAV | FDREDDETIH | AQKFQGRVTM |
| AM_H12 | SEQ ID NO:12 | QVQLVQSGAE | VKKPGASVKV | SCKVSGYTLT | ELSMHWVRQA | PGKGLEWMGG | FDREDDETIH | AQKFQGRVTM |
| AM_H17 | SEQ ID NO:17 | EVQLLESGGG | LVQPGGSLRL | SCAASRFTFS | SYAMSWVRQA | PGKGLEWVSA | ISGSGGSTYY | ADSVKGRFTI |

|  |  | 71 |  |  | CDR3 |  | 122 |  |
|---|---|---|---|---|---|---|---|---|
| AM_H1 | SEQ ID NO: 1 | SRDNSKNTLY | LQMNSLRAED | TAVYYCAKGS | SSIWLTQSLD | HWGQGTTVTV | SS | ... |
| AM_H2 | SEQ ID NO: 2 | SRDNSKNTLY | LQMNSLRAED | TAVYYCAKGS | SSIWLTQSLD | HWGQGTTVTV | SS | ... |
| AM_H3 | SEQ ID NO: 3 | SRDNSKNTLY | LQMNSLRAED | TAVYYCAKGS | SSIWLSQSLD | GWGQGTTVTV | SS | ... |
| AM_H4 | SEQ ID NO: 4 | SRDNSKNTLY | LQMNSLRAED | TAVYYCAKGS | SSIWLSQSLD | GWGQGTTVTV | SS | ... |
| AM_H5 | SEQ ID NO: 5 | SRDNSKNTLY | LQMNSLRAED | TAVYYCAKGS | SSIWLTSALN | LWGQGTTVTV | SS | ... |
| AM_H6 | SEQ ID NO: 6 | SRDNSKNTLY | LQMNSLRAED | TAVYYCAKGS | SSIWLTSALN | LWGQGTTVTV | SS | ... |
| AM_H15 | SEQ ID NO:15 | SRDNSKNTLY | LQMNSLRAED | TAVYYCARVR | GDY....RTD | IWGRGTLVTV | SS | ... |
| AM_H16 | SEQ ID NO:16 | SRDNSKNTLY | LQMNSLRAED | TAVYYCARVR | GDY....RTD | IWGRGTLVTV | SS | ... |
| AM_H13 | SEQ ID NO:13 | SRDNSKNTLY | LQMNSLRAED | TAVYYCARIR | GDY....RTD | IWGQGTTVTV | SS | ... |
| AM_H14 | SEQ ID NO:14 | SRDNSKNTLY | LQMNSLRAED | TAVYYCARIR | GDY....RTD | IWGRGTLVTV | SS | ... |
| AM_H8 | SEQ ID NO: 8 | TEDTSTDTAY | MELSSLRSED | TAVYYCATDL | M.VWGDFWIQ | HWGQGTLVTV | SS | ... |
| AM_H9 | SEQ ID NO: 9 | TEDTSTDTAY | MELSSLRSED | TAVYYCATDL | M.VWGDFWIQ | HWGQGTLVTV | SS | ... |
| AM_H10 | SEQ ID NO:10 | TEDTSTDTAY | MELSSLRSED | TAVYYCATDL | M.AWDYPPIQ | HWGQGTLVTV | SS | ... |
| AM_H11 | SEQ ID NO:11 | SRDNSKNTLY | LQMNSLRAED | TAVYYCATDL | M.VWNFPPIQ | HWGQGTLVTV | SS | ... |
| AM_H7 | SEQ ID NO: 7 | SRDNSKNTLY | LQMNSLRAED | TAIYYCAKGS | SSIWFGETVD | YWGQGTT... | | ... |
| AM_H12 | SEQ ID NO:12 | TEDTSTDTAY | MELSSLRSED | TAVYYCATDL | M VWGDFWIQ | HWGKGTM... | | ... |
| AM_H17 | SEQ ID NO:17 | SRDNSKNTLY | LQMNSLRAED | TAVYYCAR.. | ..VRGIYGMD | VWGRGTL... | | ... |

FIGURE 3A

Light Chain

|  |  | 1 | CDR1 | | | CDR2 | 70 |
|---|---|---|---|---|---|---|---|
| AM_L17 | SEQ ID NO:34 | SSELTQDPAV | SVALGQTVRV | TCQG..DSLR | SYYASWYQQK | PGQAPVLVIS | AKNNRPSGIP | DRFSGSSSGN |
| AM_L16 | SEQ ID NO:33 | SSELTQDPAV | SVALGQTVRI | TCQG..DSLR | SYYASWYQQK | PGQAPVLVIS | AKNNRPSGIP | DRFSGSSSGN |
| AM_L15 | SEQ ID NO:32 | SSELTQDPAV | SVALGQTVRV | TCQS..DSLR | SYYASWYQQK | PGQAPVLVIS | AKNNRPSGIP | DRFSGSSSGN |
| AM_L13 | SEQ ID NO:30 | SSELTQDPAV | SVALGQTVRV | TCQG..DSIR | SYYASWYQQK | PGQAPVLVIS | AKNNRPSGIP | DRFSGSSSGN |
| AM_L14 | SEQ ID NO:31 | SSELTQDPAV | SVALGQTVRI | TCQG..DSLR | SYYASWYQQK | PGQAPVLVIS | AKNNRPSGIP | DRFSGSSSGN |
| AM_L12 | SEQ ID NO:29 | QSELTQDPAV | SVALGQTVRI | TCSG..DSLR | SYYASWYQQK | PGQAPVLVIS | AKNNRPSGIP | DRFSGSSSGN |
| AM_L3 | SEQ ID NO:20 | QPVLTQPPSV | SVSPGQTASI | TCSG..DKLG | DKYASWYQQK | PGQTPVLVIY | QDSNRPSGIP | DRFSGSNSGN |
| AM_L4 | SEQ ID NO:21 | QPVLTQPPSV | SVSPGQTASI | TCSG..DKLG | DKYASWYQQK | PGQSPVLVIY | QDSNRPSGIP | ERFSGSNSGD |
| AM_L2 | SEQ ID NO:19 | QPVLTQPPSV | SVSPGQTASI | TCSG..DKLG | DKYASWYQQK | PGKSPVLVIY | QDSNRPSGIP | ERFSGSNSGN |
| AM_L5 | SEQ ID NO:22 | SYELTQPPSV | SVSPGQTASI | TCSG..DKLG | DKYASWYQQK | PGQSPVLVIY | QDSNRPSGIP | ERFSGSNSGN |
| AM_L11 | SEQ ID NO:28 | QSVLTQPPSA | SGTPGQRVTI | SCSGRNSNIG | SYTVTWYQQL | PGTAPKLLIY | SNSQRPSGVP | DRFSGSKSGT |
| AM_L7 | SEQ ID NO:24 | QSVLTQPPSA | SGTPGQRVTI | SCSGRNSNIG | SYTVTWYQQL | PGTAPKLLIY | SNSQRPSGVP | DRFSGSKSGT |
| AM_L9 | SEQ ID NO:26 | QSVLTQPPSA | SGTPGQRVTI | SCSGRNSNIG | SYTVTWYQQL | PGTAPKLLIY | SNSQRPSGVP | DRFSGSKSGT |
| AM_L8 | SEQ ID NO:25 | QSVLTQPPSA | SGTPGQRVTI | SCSGRNSNIG | SYTVTWYQQL | PGTAPKLLIY | SNSQRPSGVP | DRFSGSKSGT |
| AM_L10 | SEQ ID NO:27 | SSELTQDPAV | SVALGQTVRI | TCQG..DSLR | SYYASWYQQK | PGQAPVLVIS | AKNNRPSGIP | DRFSGSSSGN |
| AM_L1 | SEQ ID NO:18 | QPVLTQPPSV | SVSPGQTASI | TCSG..DKLG | DKYASWYQQK | PGKSPVLVIY | QDSNRPSGIP | ERFSGSNSGN |
| AM_L6 | SEQ ID NO:23 | QSVLTQPPSA | SGTPGQRVTI | SCSGRNSNIG | SYTVTWYQQL | PGTAPKLLIY | SNSQRPSGVP | DRFSGSKSGT |

|  |  | 51 | | CDR3 | | 129 |
|---|---|---|---|---|---|---|
| AM_L17 | SEQ ID NO:34 | TASLTITGAQ | AEDEADYYCA | TRNGWNH.VV | FGGGTKLTVL | G........ |
| AM_L16 | SEQ ID NO:33 | TASLTITGAQ | AEDEADYYCA | TRNGWNH.VV | FGGGTKLTVL | G........ |
| AM_L15 | SEQ ID NO:32 | TASLTITGAQ | AEDEADYYCA | SRNGWNH.VV | FGGGTKLTVL | G........ |
| AM_L13 | SEQ ID NO:30 | TASLTITGAQ | AEDEADYYCA | SRNGWNH.VV | FGGGTKLTVL | G........ |
| AM_L14 | SEQ ID NO:31 | TASLTITGAQ | AEDEADYYCA | SRNGWNH.VV | FGGGTKLTVL | G........ |
| AM_L12 | SEQ ID NO:29 | TASLTITGAQ | AEDEADYYCA | SRNGWNH.VV | FGGGTKLTVL | G........ |
| AM_L3 | SEQ ID NO:20 | TATLTISGTQ | ARDEADYYCQ | AWTSALN.SQ | FGGGTKVTVL | G........ |
| AM_L4 | SEQ ID NO:21 | TATLTISGTQ | ARDEADYYCQ | AWTHSLS.TL | FGGGTKVTVL | G........ |
| AM_L2 | SEQ ID NO:19 | TATLTISGTQ | ARDEADYYCQ | AWDHSLQ.HR | FGGGTKVTVL | G........ |
| AM_L5 | SEQ ID NO:22 | TATLTISGTQ | AMDEADYYCQ | AWTHSLS.TL | FGGGTKLTVL | G........ |
| AM_L11 | SEQ ID NO:28 | SASLAISGLQ | SEDEADYYCL | VWDDVLNGPV | FGGGTKLTVL | G........ |
| AM_L7 | SEQ ID NO:24 | SASLAISGLQ | SEDEADYYCV | VWDDVLNGPV | FGGGTKLTVL | G........ |
| AM_L9 | SEQ ID NO:26 | SASLAISGLQ | SEDEADYYCV | VWDEILNGPV | FGGGTKLTVL | G........ |
| AM_L8 | SEQ ID NO:25 | SASLAISGLQ | SEDEADYYCV | VWDDKLNGPV | FGGGTKLTVL | G........ |
| AM_L10 | SEQ ID NO:27 | TASLTITGAQ | AEDEADYYCN | SRDSS.NHVV | FGGGTK.... |  |
| AM_L1 | SEQ ID NO:18 | TATLTISGTQ | ARDEADYYCQ | AWDSS.TASV | FGGGTK.... |  |
| AM_L6 | SEQ ID NO:23 | SASLAISGLQ | SEDEADYYCA | AWDDSLNGPV | FGGGTK.... |  |

MNCRELPLTLWVLISVSTAESCTSRPHITVVEGEPFYLKHCSCSLAHEIETTTKSWYKSSGSQEHVELNPR
SSSRIALHDCVLEFWPVELNDTGSYFFQMKNYTQKWKLNVIRRNKHSCFTERQVTSKIVEVKKFFQITCE
NSYYQTLVNSTSLYKNCKKLLLENNKNPTIKKNAEFEDQGYYSCVHFLHHNGKLFNITKTFNITIVEDRSNI
VPVLLGPKLNHVAVELGKNVRLNCSALLNEEDVIYWMFGEENGSDPNIHEEKEMRIMTPEGKWHASKVL
RIENIGESNLNVLYNCTVASTGGTDTKSFILVRKADMADIPGHVFTRGMIIAVLILVAVVCLVTVCVIYRVDLV
LFYRHLTRRDETLTDGKTYDAFVSYLKECRPENGEEHTFAVEILPRVLEKHFGYKLCIFERDVVPGGAVVD
EIHSLIEKSRRLIIVLSKSYMSNEVRYELESGLHEALVERKIKIILIEFTPVTDFTFLPQSLKLLKSHRVLKWKA
DKSLSYNSRFWKNLLYLMPAKTVKPGRDEPEVLPVLSES

Amino acids of the human IL-18

AM_H6 (SEQ ID NO:74)

GTCGACGCCGCCACCATGGGGTCAACCGCCATCCTTGGCCTCCTCCTGGCTGT
CCTGCAGGGAGGGCGCGCCGAGGTGCAGCTGGTGGAGTCTGGGGGAGGCGT
GGTCCAGCCTGGGAGGTCCCTGAGACTCTCCTGTGCAGCGTCTGGATTCACCT
TCAGCGGTTATGGCATGCACTGGGTCCGCCAGGCTCCAGGCAAGGGGCTGGA
GTGGGTGGCAGTAATATCAAATGATGGAAGTAAGAAATATTATTCAGACTCC
GTGAAGGGCCGATTCACCATCTCCAGAGACAATTCCAAAAACACGCTGTATC
TGCAGATGAACAGCCTGAGAGCTGAGGACACGGCTGTATATTACTGTGCGAA
AGGGTCCAGTTCCATATGGCTGACCTCGGCCCTGAACCTGTGGGGGCAGGGG
ACCACGGTCACCGTCTCCTCAGCTAGCACCAAGGGCCCATCGGTCTTCCCCCT
GGCGCCCTGCTCCAGGAGCACCTCCGAGAGCACAGCGGCCCTGGGCTGCCTG
GTCAAGGACTACTTCCCCGAACCGGTGACGGTGTCGTGGAACTCAGGCGCTC
TGACCAGCGGCGTGCACACCTTCCCAGCTGTCCTACAGTCCTCAGGACTCTAC
TCCCTCAGCAGCGTGGTGACCGTGCCCTCCAGCAACTTCGGCACCCAGACCT
ACACCTGCAACGTAGATCACAAGCCCAGCAACACCAAGGTGGACAAGACAG
TTGAGCGCAAATGTTGTGTCGAGTGCCCACCGTGCCCAGCACCACCTGTGGC
AGGACCGTCAGTCTTCCTCTTCCCCCCAAAACCCAAGGACACCCTCATGATCT
CCCGGACCCCTGAGGTCACGTGCGTGGTGGTGGACGTGAGCCACGAAGACCC
CGAGGTCCAGTTCAACTGGTACGTGGACGGCGTGGAGGTGCATAATGCCAAG
ACAAAGCCACGGGAGGAGCAGTTCAACAGCACGTTCCGTGTGGTCAGCGTCC
TCACCGTTGTGCACCAGGACTGGCTGAACGGCAAGGAGTACAAGTGCAAGGT
CTCCAACAAAGGCCTCCCAGCCCCCATCGAGAAAACCATCTCCAAAACCAAA
GGGCAGCCCCGAGAACCACAGGTGTACACCCTGCCCCCATCCCGGGAGGAG
ATGACCAAGAACCAGGTCAGCCTGACCTGCCTGGTCAAAGGCTTCTACCCCA
GCGACATCGCCGTGGAGTGGGAGAGCAATGGGCAGCCGGAGAACAACTACA
AGACCACACCTCCCATGCTGGACTCCGACGGCTCCTTCTTCCTCTACAGCAAG
CTCACCGTGGACAAGAGCAGGTGGCAGCAGGGGAACGTCTTCTCATGCTCCG
TGATGCATGAGGCTCTGCACAACCACTACACGCAGAAGAGCCTCTCCCTGTC
TCCGGGTAAATGAGCGGCCGC

AM_H6 (SEQ ID NO:73)

MGSTAILGLLLAVLQGGRA^EVQLVESGGGVVQPGRSLRLSCAASGFTFSG
YGMHWVRQAPGKGLEWVAVISNDGSKKYYSDSVKGRFTISRDNSKNTLYL
QMNSLRAEDTAVYYCAKGSSSIWLTSALNLWGQGTTVTVSSASTKGPSVF
PLAPCSRSTSESTAALGCLVKDYFPEPVTVSWNSGALTSGVHTFPAVLQS
SGLYSLSSVVTVPSSNFGTQTYTCNVDHKPSNTKVDKTVERKCCVECPPC
PAPPVAGPSVFLFPPKPKDTLMISRTPEVTCVVVDVSHEDPEVQFNWYVD
GVEVHNAKTKPREEQFNSTFRVVSVLTVVHQDWLNGKEYKCKVSNKGLPA
PIEKTISKTKGQPREPQVYTLPPSREEMTKNQVSLTCLVKGFYPSDIAVE
WESNGQPENNYKTTPPMLDSDGSFFLYSKLTVDKSRWQQGNVFSCSVMHE
ALHNHYTQKSLSLSPGK

FIGURE 6

AM$_L$12 (SEQ ID NO:76)

GTCGACGTTTAAACGCCGCCACCATGGAGACAGACACACTCCTGCTATGGGT
ACTGCTGCTCTGGGTTCCAGGTTCCACTGGTTCGTCTGAGCTGACTCAGGACC
CTGCTGTGTCTGTGGCCTTGGGACAGACAGTCAGGATCACATGCCAAGGAGA
CAGCCTCAGAAGCTATTATGCAAGCTGGTACCAGCAGAAGCCAGGACAGGCC
CCTGTACTTGTCATCTCTGCTAAAAACAACCGGCCCTCAGGGATCCCAGACC
GATTCTCTGGCTCCAGCTCAGGAAACACAGCTTCCTTGACCATCACTGGGGCT
CAGGCGGAAGATGAGGCTGACTATTACTGTGCGTCCCGGAACGGCTGGAACC
ATGTGGTATTCGGCGGAGGGACCAAGCTGACCGTCCTAGGCCAACCGAAAGC
GGCGCCCTCGGTCACTCTGTTCCCGCCCTCCTCTGAGGAGCTTCAAGCCAACA
AGGCCACACTGGTGTGTCTCATAAGTGACTTCTACCCGGGAGCCGTGACAGT
GGCCTGGAAGGCAGATAGCAGCCCCGTCAAGGCGGGAGTGGAGACCACCAC
ACCCTCCAAACAAAGCAACAACAAGTACGCGGCCAGCAGCTATCTGAGCCTG
ACGCCTGAGCAGTGGAAGTCCCACAGAAGCTACAGCTGCCAGGTCACGCATG
AAGGGAGCACCGTGGAGAAGACAGTGGCCCCTACAGAATGTTCATAGGCGG
CCGC

AM$_L$12 (SEQ ID NO:75)

METDTLLLWVLLLWVPGSTG^SSELTQDPAVSVALGQTVRITCQGDSLRSYYA
SWYQQKPGQAPVLVISAKNNRPSGIPDRFSGSSSGNTASLTITGAQAEDEADY
YCASRNGWNHVVFGGGTKLTVLGQPKAAPSVTLFPPSSEELQANKATLVCLI
SDFYPGAVTVAWKADSSPVKAGVETTTPSKQSNNKYAASSYLSLTPEQWKS
HRSYSCQVTHEGSTVEKTVAPTECS

FIGURE 7

AM$_H$4 (SEQ ID NO:78)

ATGGGGTCAACCGCCATCCTTGGCCTCCTCCTGGCTGTCCTGCAGGGAGGGC
GCGCCGAGGTGCAGCTGGTGGAGTCTGGGGGAGGCGTGGTCCAGCCTGGGA
GGTCCCTGAGACTCTCCTGTGCAGCGTCTGGATTCACCTTCAGCGGTTATGGC
ATGCACTGGGTCCGCCAGGCTCCAGGCAAGGGGCTGGAGTGGGTGGCAGTAA
TATCAAATGATGGAAGTAAGAAATATTATTCAGACTCCGTGAAGGGCCGATT
CACCATCTCCAGAGACAATTCCAAAAACACGCTGTATCTGCAGATGAACAGC
CTGAGAGCTGAGGACACGGCTGTATATTACTGTGCGAAAGGGTCCAGTTCCA
TATGGCTGTCGCAGTCCCTGGACGGCTGGGGGCAGGGGACCACGGTCACCGT
CTCCTCAGCTAGCACCAAGGGCCCATCGGTCTTCCCCCTGGCGCCCTGCTCCA
GGAGCACCTCCGAGAGCACAGCGGCCCTGGGCTGCCTGGTCAAGGACTACTT
CCCCGAACCGGTGACGGTGTCGTGGAACTCAGGCGCTCTGACCAGCGGCGTG
CACACCTTCCCAGCTGTCCTACAGTCCTCAGGACTCTACTCCCTCAGCAGCGT
GGTGACCGTGCCCTCCAGCAACTTCGGCACCCAGACCTACACCTGCAACGTA
GATCACAAGCCCAGCAACACCAAGGTGGACAAGACAGTTGAGCGCAAATGT
TGTGTCGAGTGCCCACCGTGCCCAGCACCACCTGTGGCAGGACCGTCAGTCT
TCCTCTTCCCCCCAAAACCCAAGGACACCCTCATGATCTCCCGGACCCCTGAG
GTCACGTGCGTGGTGGTGGACGTGAGCCACGAAGACCCCGAGGTCCAGTTCA
ACTGGTACGTGGACGGCGTGGAGGTGCATAATGCCAAGACAAAGCCACGGG
AGGAGCAGTTCAACAGCACGTTCCGTGTGGTCAGCGTCCTCACCGTTGTGCA
CCAGGACTGGCTGAACGGCAAGGAGTACAAGTGCAAGGTCTCCAACAAAGG
CCTCCCAGCCCCCATCGAGAAAACCATCTCCAAAACCAAAGGGCAGCCCCGA
GAACCACAGGTGTACACCCTGCCCCCATCCCGGGAGGAGATGACCAAGAACC
AGGTCAGCCTGACCTGCCTGGTCAAAGGCTTCTACCCCAGCGACATCGCCGT
GGAGTGGGAGAGCAATGGGCAGCCGGAGAACAACTACAAGACCACACCTCC
CATGCTGGACTCCGACGGCTCCTTCTTCCTCTACAGCAAGCTCACCGTGGACA
AGAGCAGGTGGCAGCAGGGGAACGTCTTCTCATGCTCCGTGATGCATGAGGC
TCTGCACAACCACTACACGCAGAAGAGCCTCTCCCTGTCTCCGGGTAAATGA

AM$_H$4 (SEQ ID NO:77)

MGSTAILGLLLAVLQGGRA^EVQLVESGGGVVQPGRSLRLSCAASGFTFSG
YGMHWVRQAPGKGLEWVAVISNDGSKKYYSDSVKGRFTISRDNSKNTLYL
QMNSLRAEDTAVYYCAKGSSSIWLSQSLDGWGQGTTVTVSSASTKGPSVF
PLAPCSRSTSESTAALGCLVKDYFPEPVTVSWNSGALTSGVHTFPAVLQS
SGLYSLSSVVTVPSSNFGTQTYTCNVDHKPSNTKVDKTVERKCCVECPPC
PAPPVAGPSVFLFPPKPKDTLMISRTPEVTCVVVDVSHEDPEVQFNWYVD
GVEVHNAKTKPREEQFNSTFRVVSVLTVVHQDWLNGKEYKCKVSNKGLPA
PIEKTISKTKGQPREPQVYTLPPSREEMTKNQVSLTCLVKGFYPSDIAVE
WESNGQPENNYKTTPPMLDSDGSFFLYSKLTVDKSRWQQGNVFSCSVMHE
ALHNHYTQKSLSLSPGK

FIGURE 8

AM$_L$14 (SEQ ID NO:80)

ATGGAGACAGACACACTCCTGCTATGGGTACTGCTGCTCTGGGTTCCAGGTTC
CACTGGTTCGTCTGAGCTGACTCAGGACCCTGCTGTGTCTGTGGCCTTGGGAC
AGACAGTCAGGATCACATGCCAAGGAGACAGCCTCAGAAGCTATTATGCAAG
CTGGTACCAGCAGAAGCCAGGACAGGCCCCTGTACTTGTCATCTCTGCTAAA
AACAACCGGCCCTCAGGGATCCCAGACCGATTCTCTGGCTCCAGCTCAGGAA
ACACAGCTTCCTTGACCATCACTGGGGCTCAGGCGGAAGATGAGGCTGACTA
TTACTGTGCGTCCCGGAACGGCTGGAACCATGTGGTATTCGGCGGAGGGACC
AAGCTGACCGTCCTAGGCCAACCGAAAGCGGCGCCCTCGGTCACTCTGTTCC
CGCCCTCCTCTGAGGAGCTTCAAGCCAACAAGGCCACACTGGTGTGTCTCAT
AAGTGACTTCTACCCGGGAGCCGTGACAGTGGCCTGGAAGGCAGATAGCAGC
CCCGTCAAGGCGGGAGTGGAGACCACCACACCCTCCAAACAAAGCAACAAC
AAGTACGCGGCCAGCAGCTATCTGAGCCTGACGCCTGAGCAGTGGAAGTCCC
ACAGAAGCTACAGCTGCCAGGTCACGCATGAAGGGAGCACCGTGGAGAAGA
CAGTGGCCCCTACAGAATGTTCATAGGCGGCCGC

AM$_L$14 (SEQ ID NO:79)

METDTLLLWVLLLWVPGSTG^SSELTQDPAVSVALGQTVRITCQGDSLRSYYA
SWYQQKPGQAPVLVISAKNNRPSGIPDRFSGSSSGNTASLTITGAQAEDEADY
YCASRNGWNHVVFGGGTKLTVLGQPKAAPSVTLFPPSSEELQANKATLVCLI
SDFYPGAVTVAWKADSSPVKAGVETTTPSKQSNNKYAASSYLSLTPEQWKS
HRSYSCQVTHEGSTVEKTVAPTECS

FIGURE 9

AM_H9 (SEQ ID NO:82)

ATGGGGTCAACCGCCATCCTTGGCCTCCTCCTGGCTGTCCTGCAGGGAGGGC
GCGCCCAGGTGCAGCTGGTGCAGTCTGGGGCTGAGGTGAAGAAGCCTGGGGC
CTCAGTGAAGGTCTCCTGCAAGGTTTCCGGATACACCCTCACTGAATTATCCA
TGCACTGGGTGCGACAGGCTCCTGGAAAAGGGCTTGAGTGGATGGGAGGTTT
TGATCGTGAAGATGATGAAACAATCCACGCACAGAAGTTCCAGGGCAGAGTC
ACCATGACCGAGGACACATCTACAGACACAGCCTACATGGAACTGAGCAGCC
TGCGATCTGAGGACACGGCCGTTTATTACTGTGCAACAGATCTTATGGTGTGG
GGCGATTTTTGGATCCAGCACTGGGGCCAGGGGACACTGGTCACCGTCTCCT
CAGCTAGCACCAAGGGCCCATCGGTCTTCCCCCTGGCGCCCTGCTCCAGGAG
CACCTCCGAGAGCACAGCGGCCCTGGGCTGCCTGGTCAAGGACTACTTCCCC
GAACCGGTGACGGTGTCGTGGAACTCAGGCGCTCTGACCAGCGGCGTGCACA
CCTTCCCAGCTGTCCTACAGTCCTCAGGACTCTACTCCCTCAGCAGCGTGGTG
ACCGTGCCCTCCAGCAACTTCGGCACCCAGACCTACACCTGCAACGTAGATC
ACAAGCCCAGCAACACCAAGGTGGACAAGACAGTTGAGCGCAAATGTTGTGT
CGAGTGCCCACCGTGCCCAGCACCACCTGTGGCAGGACCGTCAGTCTTCCTCT
TCCCCCCAAAACCCAAGGACACCCTCATGATCTCCCGGACCCCTGAGGTCAC
GTGCGTGGTGGTGGACGTGAGCCACGAAGACCCCGAGGTCCAGTTCAACTGG
TACGTGGACGGCGTGGAGGTGCATAATGCCAAGACAAAGCCACGGGAGGAG
CAGTTCAACAGCACGTTCCGTGTGGTCAGCGTCCTCACCGTTGTGCACCAGG
ACTGGCTGAACGGCAAGGAGTACAAGTGCAAGGTCTCCAACAAAGGCCT
CCCAGCCCCCATCGAGAAAACCATCTCCAAAACCAAAGGGCAGCCCCGAGA
ACCACAGGTGTACACCCTGCCCCCATCCCGGGAGGAGATGACCAAGAACCAG
GTCAGCCTGACCTGCCTGGTCAAAGGCTTCTACCCCAGCGACATCGCCGTGG
AGTGGGAGAGCAATGGGCAGCCGGAGAACAACTACAAGACCACACCTCCCA
TGCTGGACTCCGACGGCTCCTTCTTCCTCTACAGCAAGCTCACCGTGGACAAG
AGCAGGTGGCAGCAGGGGAACGTCTTCTCATGCTCCGTGATGCATGAGGCTC
TGCACAACCACTACACGCAGAAGAGCCTCTCCCTGTCTCCGGGTAAATGA

AM_H9 (SEQ ID NO:81)

MGSTAILGLLLAVLQGGRA^QVQLVQSGAEVKKPGASVKVSCKVSGYTLTE
LSMHWVRQAPGKGLEWMGGFDREDDETIHAQKFQGRVTMTEDTSTDTAYM
ELSSLRSEDTAVYYCATDLMVWGDFWIQHWGQGTLVTVSSASTKGPSVFP
LAPCSRSTSESTAALGCLVKDYFPEPVTVSWNSGALTSGVHTFPAVLQSS
GLYSLSSVVTVPSSNFGTQTYTCNVDHKPSNTKVDKTVERKCCVECPPCP
APPVAGPSVFLFPPKPKDTLMISRTPEVTCVVVDVSHEDPEVQFNWYVDG
VEVHNAKTKPREEQFNSTFRVVSVLTVVHQDWLNGKEYKCKVSNKGLPAP
IEKTISKTKGQPREPQVYTLPPSREEMTKNQVSLTCLVKGFYPSDIAVEW
ESNGQPENNYKTTPPMLDSDGSFFLYSKLTVDKSRWQQGNVFSCSVMHEA
LHNHYTQKSLSLSPGK

FIGURE 10

AM$_L$9 (SEQ ID NO:84)

ATGGAGACAGACACACTCCTGCTATGGGTACTGCTGCTCTGGGTTCCAGGTTC
CACTGGTGCTAGCCAGTCTGTGCTGACTCAGCCACCCTCAGCGTCTGGGACCC
CCGGGCAGAGGGTCACCATCTCTTGTTCTGGAAGGAACTCCAACATCGGAAG
TTATACTGTAACCTGGTACCAGCAGCTCCCAGGAACGGCCCCCAAACTCCTC
ATCTATAGTAATAGTCAGCGGCCCTCAGGGGTCCCTGACCGATTCTCAGGCTC
CAAGTCTGGCACCTCAGCCTCCTTGGCCATCAGTGGGCTCCAGTCTGAAGAT
GAGGCTGATTATTACTGTGTGGTGTGGGACGAGATCCTGAATGGCCCGGTGT
TCGGCGGAGGGACCAAGCTGACCGTCCTAGGCCAACCGAAAGCGGCGCCCTC
GGTCACTCTGTTCCCGCCCTCCTCTGAGGAGCTTCAAGCCAACAAGGCCACA
CTGGTGTGTCTCATAAGTGACTTCTACCCGGGAGCCGTGACAGTGGCCTGGA
AGGCAGATAGCAGCCCCGTCAAGGCGGGAGTGGAGACCACCACACCCTCCA
AACAAAGCAACAACAAGTACGCGGCCAGCAGCTATCTGAGCCTGACGCCTG
AGCAGTGGAAGTCCCACAGAAGCTACAGCTGCCAGGTCACGCATGAAGGGA
GCACCGTGGAGAAGACAGTGGCCCCTACAGAATGTTCATAG

AM$_L$9 (SEQ ID NO:83)

METDTLLLWVLLLWVPGSTG^ASQSVLTQPPSASGTPGQRVTISCSGRNSN
IGSYTVTWYQQLPGTAPKLLIYSNSQRPSGVPDRFSGSKSGTSASLAISG
LQSEDEADYYCVVWDEILNGPVFGGGTKLTVLGQPKAAPSVTLFPPSSEE
LQANKATLVCLISDFYPGAVTVAWKADSSPVKAGVETTTPSKQSNNKYAA
SSYLSLTPEQWKSHRSYSCQVTHEGSTVEKTVAPTECS

FIGURE 11

AM$_H$11 (SEQ ID NO:86)

ATGGGGTCAACCGCCATCCTTGGCCTCCTCCTGGCTGTCCTGCAGGGAGGGC
GCGCCCAGGTGCAGCTGGTGCAGTCTGGGGCTGAGGTGAAGAAGCCTGGGGC
CTCAGTGAAGGTCTCCTGCAAGGTTTCCGGATACACCCTCACTGAATTATCCA
TGCACTGGGTGCGACAGGCTCCTGGAAAAGGGCTTGAGTGGATGGGAGGTTT
TGATCGTGAAGATGATGAAACAATCCACGCACAGAAGTTCCAGGGCAGAGTC
ACCATGACCGAGGACACATCTACAGACACAGCCTACATGGAACTGAGCAGCC
TGCGATCTGAGGACACGGCCGTTTATTACTGTGCAACAGATCTTATGGTGTGG
AACTTCCCCCCCATCCAGCACTGGGGCCAGGGGACACTGGTCACCGTCTCCT
CAGCTAGCACCAAGGGCCCATCGGTCTTCCCCCTGGCGCCCTGCTCCAGGAG
CACCTCCGAGAGCACAGCGGCCCTGGGCTGCCTGGTCAAGGACTACTTCCCC
GAACCGGTGACGGTGTCGTGGAACTCAGGCGCTCTGACCAGCGGCGTGCACA
CCTTCCCAGCTGTCCTACAGTCCTCAGGACTCTACTCCCTCAGCAGCGTGGTG
ACCGTGCCCTCCAGCAACTTCGGCACCCAGACCTACACCTGCAACGTAGATC
ACAAGCCCAGCAACACCAAGGTGGACAAGACAGTTGAGCGCAAATGTTGTGT
CGAGTGCCCACCGTGCCCAGCACCACCTGTGGCAGGACCGTCAGTCTTCCTCT
TCCCCCCAAAAACCCAAGGACACCCTCATGATCTCCCGGACCCCTGAGGTCAC
GTGCGTGGTGGTGGACGTGAGCCACGAAGACCCCGAGGTCCAGTTCAACTGG
TACGTGGACGGCGTGGAGGTGCATAATGCCAAGACAAAGCCACGGGAGGAG
CAGTTCAACAGCACGTTCCGTGTGGTCAGCGTCCTCACCGTTGTGCACCAGG
ACTGGCTGAACGGCAAGGAGTACAAGTGCAAGGTCTCCAACAAAGGCCTCCC
AGCCCCCATCGAGAAAACCATCTCCAAAACCAAAGGGCAGCCCCGAGAACC
ACAGGTGTACACCCTGCCCCCATCCCGGGAGGAGATGACCAAGAACCAGGTC
AGCCTGACCTGCCTGGTCAAAGGCTTCTACCCCAGCGACATCGCCGTGGAGT
GGGAGAGCAATGGGCAGCCGGAGAACAACTACAAGACCACACCTCCCATGC
TGGACTCCGACGGCTCCTTCTTCCTCTACAGCAAGCTCACCGTGGACAAGAG
CAGGTGGCAGCAGGGGAACGTCTTCTCATGCTCCGTGATGCATGAGGCTCTG
CACAACCACTACACGCAGAAGAGCCTCTCCCTGTCTCCGGGTAAATGA

AM$_H$11 (SEQ ID NO:85)

MGSTAILGLLLAVLQGGRA^QVQLVQSGAEVKKPGASVKVSCKVSGYTLTE
LSMHWVRQAPGKGLEWMGGFDREDDETIHAQKFQGRVTMTEDTSTDTAYM
ELSSLRSEDTAVYYCATDLMVWNFPPIQHWGQGTLVTVSSASTKGPSVFP
LAPCSRSTSESTAALGCLVKDYFPEPVTVSWNSGALTSGVHTFPAVLQSS
GLYSLSSVVTVPSSNFGTQTYTCNVDHKPSNTKVDKTVERKCCVECPPCP
APPVAGPSVFLFPPKPKDTLMISRTPEVTCVVVDVSHEDPEVQFNWYVDG
VEVHNAKTKPREEQFNSTFRVVSVLTVVHQDWLNGKEYKCKVSNKGLPAP
IEKTISKTKGQPREPQVYTLPPSREEMTKNQVSLTCLVKGFYPSDIAVEW
ESNGQPENNYKTTPPMLDSDGSFFLYSKLTVDKSRWQQGNVFSCSVMHEA
LHNHYTQKSLSLSPGK

FIGURE 12

AM$_L$7 (SEQ ID NO:88)

ATGGAGACAGACACACTCCTGCTATGGGTACTGCTGCTCTGGGTTCCAGGTTC
CACTGGTGCTAGCCAGTCTGTGCTGACTCAGCCACCCTCAGCGTCTGGGACCC
CCGGGCAGAGGGTCACCATCTCTTGTTCTGGAAGGAACTCCAACATCGGAAG
TTATACTGTAACCTGGTACCAGCAGCTCCCAGGAACGGCCCCCAAACTCCTC
ATCTATAGTAATAGTCAGCGGCCCTCAGGGGTCCCTGACCGATTCTCAGGCTC
CAAGTCTGGCACCTCAGCCTCCTTGGCCATCAGTGGGCTCCAGTCTGAAGAT
GAGGCTGATTATTACTGTGTGGTGTGGGATGACGTGCTGAATGGCCCGGTGTT
CGGCGGAGGGACCAAGCTGACCGTCCTAGGCCAACCGAAAGCGGCGCCCTC
GGTCACTCTGTTCCCGCCCTCCTCTGAGGAGCTTCAAGCCAACAAGGCCACA
CTGGTGTGTCTCATAAGTGACTTCTACCCGGGAGCCGTGACAGTGGCCTGGA
AGGCAGATAGCAGCCCCGTCAAGGCGGGAGTGGAGACCACCACACCCTCCA
AACAAAGCAACAACAAGTACGCGGCCAGCAGCTATCTGAGCCTGACGCCTG
AGCAGTGGAAGTCCCACAGAAGCTACAGCTGCCAGGTCACGCATGAAGGGA
GCACCGTGGAGAAGACAGTGGCCCCTACAGAATGTTCATAG

AM$_L$7 (SEQ ID NO:87)

METDTLLLWVLLLWVPGSTG^ASQSVLTQPPSASGTPGQRVTISCSGRNSN
IGSYTVTWYQQLPGTAPKLLIYSNSQRPSGVPDRFSGSKSGTSASLAISG
LQSEDEADYYCVVWDDVLNGPVFGGGTKLTVLGQPKAAPSVTLFPPSSEE
LQANKATLVCLISDFYPGAVTVAWKADSSPVKAGVETTTPSKQSNNKYAA
SSYLSLTPEQWKSHRSYSCQVTHEGSTVEKTVAPTECS

FIGURE 13

IL-18 RECEPTOR ANTIGEN BINDING PROTEINS

This application is a National Stage application under 35 U.S.C. §371 of International Application No. PCT/US2008/071047 (which designated the United States), having an international filing date of Jul. 24, 2008, which claims the priority benefit of U.S. Provisional Patent Application Ser. No. 61/073,142, filed Jun. 17, 2008, U.S. Provisional Patent Application Ser. No. 60/951,692, filed Jul. 24, 2007, and U.S. Provisional Patent Application Ser. No. 60/951,691, filed Jul. 24, 2007 each of which is hereby incorporated by reference in its entirety.

REFERENCE TO THE SEQUENCE LISTING

The present application is being filed along with a Sequence Listing in electronic format. The Sequence Listing is provided as a file entitled Sequence Listing.txt, created Jan. 21, 2010, which is 134 KB in size. The information in the electronic format of the Sequence Listing is incorporated herein by reference in its entirety.

I. FIELD OF THE INVENTION

Provided herein are IL-18 receptor antigen binding proteins and polynucleotides encoding the same. Expression vectors and host cells comprising the same for production of the antigen binding proteins are also provided. In addition, provided are compositions and methods for diagnosing and treating diseases mediated by IL-18 receptor.

II. BACKGROUND

IL-18 is a proinflammatory cytokine that belongs to the IL-1 family of ligands. Okamura et al., 1995, *Nature* 378:88-91. Also referred to as IFN-γ-inducing factor, IL-18 is a cytokine that plays an important role in the TH1 response, primarily by its ability to induce IFN-γ production in T cells and natural killer cells. IL-18 is related to the IL-1 family in both structure and function. In terms of structure, IL-18 and IL-1β share significant primary amino acid sequences and are both folded as β-sheet polypeptides. In terms of function, IL-18 induces gene expression and synthesis of IL-1, TNF, Fas ligand, and several cytokines.

The activity of IL-18 is transduced through a signal transducing pathway initiated by its forming of a IL-18 receptor (IL-18R) complex. The IL-18R includes a binding chain termed α-IL-18 receptor (α-IL-18R), a member of the IL-1R family previously identified as the IL-1R-related protein (IL-1Rrp), and a β-IL-18 receptor (β-IL-18R), also a member of the IL-1R family and previously identified as AcPL; both chains are required for signaling. Born et al., 1998, *J. Biol. Chem.* 273:29445-50. The IL-18/IL-18R complex recruits IL-1R-activating kinase and TNF receptor-associated factor-6, which phosphorylates nuclear factor kappaB (NFkappaB)-inducing kinase with subsequent activation of NFkappaB. IL-18 participates in both innate and acquired immunity. Dinarello, 1999, *J. Allergy Clin. Immun.* 103:11-24.

Increased levels of IL-18 and/or involvement of IL-18 mediated signals in pathogenesis have been demonstrated in a variety of human disease states, including autoimmune diseases (WO2004/002519; WO2005/063290; WO2004/034988; Mallet et al., 2002, *Circ. Res.* 91:441-448), hepatic diseases (Finitto et al., 2004, *Liver* 53:392-400; Tsutsui et al., 2000, *Immunological Reviews* 174:192-209; Ludwiczek et al., 2002, *J. Clinical Immunology* 22:331-337), pancreatic diseases, and cardiovascular diseases (Gerdes et al, 2002, *J. Exp. Med.* 195:245-257; WO03/080104; WO02/060479; WO01/85201; Raeburn et al., 2002, *Am. J. Physiol. Heart Circ. Physiol.* 283:H650-H657). Accordingly, it is desirable to generate new agents capable of modulating the IL-18/IL-18 receptor interaction.

III. SUMMARY

Provided herein are α- and β-IL-18 receptor (also referred to herein collectively as "IL-18 receptor" or "IL-18R") antigen binding proteins and polynucleotides that encode them. The IL-18 receptor antigen binding proteins inhibit, interfere with, or modulate at least one of the biological responses mediated by IL-18 and as such can be useful for ameliorating the effects of IL-18 mediated diseases or disorders. Also provided are expression systems, including cell lines, for the production of α- and β-IL-18 receptor antigen binding proteins and methods for diagnosing and treating diseases associated with aberrant IL-18 activity.

In one embodiment, antigen binding proteins bind the α- and β-IL-18 receptor, and comprise (a) a scaffold structure; and (b) at least one complementary determining region (CDR), selected from the CDRH regions of any of SEQ ID NOs:89-139 or the CDRL regions of any of SEQ ID NOs:140-190. In this embodiment, of particular use are antigen binding proteins with a CDRH3 or CDRL3 region of SEQ ID NO:91, 94, 97, 100, 103, 106, 109, 112, 115, 118, 121, 124, 127, 130, 133, 136, 139 or SEQ ID NO:142, 145, 148, 151, 154, 157, 160, 163, 166, 169, 172, 175, 178, 181, 184, 187, 190, respectively. Additional embodiments utilize antigen binding proteins with one CDR selected from the CDRH regions of any of SEQ ID NOs:89-139 and a CDRL region of any of SEQ ID NOs:140-190 (e.g., the antigen binding protein has two CDR regions, one heavy and one light; again, in a specific embodiment the antigen binding proteins have both a CDRH3 and a CDRL3 region).

The antigen binding proteins can bind to an IL-18 receptor α- or β-chain having the amino acid sequence of SEQ ID NO:69 or SEQ ID NO:71, respectively.

Described herein are antigen binding proteins that comprise a heavy chain amino acid sequence that comprises at least one CDR selected from the group consisting of: (a) a CDRH1 of any of SEQ ID NOs:89, 92, 95, 98, 101, 104, 107, 110, 113, 116, 119, 122, 125, 128, 131, 134, 137; (b) a CDRH2 of any of SEQ ID NOs:90, 93, 96, 99, 102, 105, 108, 111, 114, 117, 120, 123, 126, 129, 132, 135, 138; and (c) a CDRH3 of any of SEQ ID NOs:91, 94, 97, 100, 103, 106, 109, 112, 115, 118, 121, 124, 127, 130, 133, 136, 139; and/or a light chain amino acid sequence that comprises at least one CDR selected from the group consisting of: (a) a CDRL1 of any of SEQ ID NOs:140, 143, 146, 149, 152, 155, 158, 161, 164, 167, 170, 173, 176, 179, 182, 185, 188; (b) a CDRL2 of any of SEQ ID NOs:141, 144, 147, 150, 153, 156, 159, 162, 165, 168, 171, 174, 177, 180, 183, 186, 189; and (c) a CDRL3 of any of SEQ ID NOs:142, 145, 148, 151, 154, 157, 160, 163, 166, 169, 172, 175, 178, 181, 184, 187, 190.

In certain aspects, the antigen binding protein comprises a heavy chain amino acid sequence having a CDRH1, a CDRH2, and a CDRH3 of any of SEQ ID NOs:89-139, and/or a light chain amino acid sequence that comprises a CDRL1, a CDRL2, and a CDRL3 of any of SEQ ID NOs:140-190. Preferred antigen binding proteins comprise a heavy chain amino acid sequence selected from the group consisting of SEQ ID NOs:1-17 and/or a light chain amino acid sequence selected from the group consisting of SEQ ID NOs:18-34. Preferred CDRH3s include those set forth in any of SEQ ID NOs:91, 94, 97, 100, 103, 106, 109, 112, 115, 118, 121, 124, 127, 130, 133, 136, 139. Preferred CDRL3s include those set forth in any of SEQ ID NOs:142, 145, 148, 151, 154, 157, 160, 163, 166, 169, 172, 175, 178, 181, 184, 187, 190.

In certain aspects, the antigen binding protein comprises one or more IgG heavy or light chains, including those of the IgG1-, IgG2-IgG3- or IgG4-type. Preferred IgG heavy chains include, but are not limited to, those set forth in SEQ ID NO:73, 77, 81, and 85. Preferred IgG light chains include, but are not limited to, those set forth in SEQ ID NO:75, 79, 83, and 87.

As described herein, antigen binding proteins that bind to amino acid residues 250-253 and 267-271 of a three dimensional structure formed by mature α-IL-18 receptor (SEQ ID NO:69) are particularly useful in blocking the interaction of IL-18 with IL-18 receptor.

An antigen binding protein can be a monoclonal antibody, a human antibody, a recombinant antibody, a chimeric antibody, a humanized antibody, a bispecific antibody, or a fragment thereof. Antibody fragments include, but are not limited to, a minibody, a domain antibody, a F(ab) fragment, a F(ab') fragment, a F(ab')$_2$ fragment, a Fv fragment, a scFv fragment, a Fd fragment, a diabody, or a single chain antibody molecule.

In other aspects, provided herein are isolated nucleic acids encoding one or more IL-18 receptor antigen binding proteins. Such nucleic acids can be comprised within a vector and operably linked to a control sequence. Also, provided herein are host cells transformed with such isolated nucleic acids.

Additionally, provided herein are pharmaceutical compositions comprising an IL-18 receptor antigen binding protein and a pharmaceutically acceptable carrier. Such pharmaceutical compositions are useful in methods for preventing or treating a condition associated with IL-18 receptor in a patient, which comprise administering an effective amount thereof to the patient. Diseases and conditions associated with IL-18 receptor include inflammatory and autoimmmune diseases (such as psoriasis, rheumatoid arthritis, juvenile idiopathic arthritis, Still's disease, ankylosing spondylitis, osteo arthritis, ulcerative arthritis, coleliac disease, psoriatic arthritis, chronic obstructive pulmonary disease, asthma, particularly chronic severe asthma, acute respiratory distress syndrome, sepsis, Alzheimer disease, lupus, allergic rhinitis, idiopathic thrombocytopenic purpura, transplantation, atopic dermatitis, type II diabetes, Crohn's disease, inflammatory bowel disease, multiple sclerosis, autoimmune hepatitis, HIV, atopic dermatitis, myasthenia gravis, sarcoidosis), a hepatic disease (such as hepatitis), a pancreatic disease (such as chronic pancreatitis or acute pancreatitis), and a cardiovascular disease (such as acute heart attacks, atheromatous plaque rupture, post-ischemic heart failure, reperfusion injury, vascular inflammation, chronic heart failure, atherosclerosis, cardiovascular complications of rheumatoid arthritis, and atherogenesis).

Further provided herein are methods of inhibiting the binding of IL-18 to IL-18 receptor comprising contacting an IL-18 receptor with an IL-18 receptor antigen binding protein. Upon binding IL-18 receptor, the IL-18 receptor antigen binding protein will prevent or block binding of the receptor to IL-18.

IV. DESCRIPTION OF THE DRAWINGS

FIGS. 1A, 1B, 1C, 1D, 1E, 1F, 1G, 1H, 1I, 1J, 1K, 1L, 1M, 1N, 1O, 1P, and 1Q depict nucleic acid and amino acid sequences of VH and VL variable domains of α- and β-IL-18 receptor antigen binding proteins.

FIGS. 2A, 2B, 2C, 2D, and 2E show the CDR1, CDR2, and CDR3 regions of various heavy and light chain variable regions of antigen binding proteins. The amino acid sequences of the various heavy and light chain regions are identified in SEQ ID NOs:1-34. The sequences of the individual CDRs are identified in SEQ ID NOs:89-190.

FIGS. 3A and 3B depict an alignment of the amino acid sequences of heavy and light chain variable sequences of α- and β-IL-18 receptor antigen binding proteins. The CDR1, CDR2 and CDR3 regions are highlighted in grey.

FIG. 4 depicts a chart showing various possible combinations of heavy chain variable regions and light chain variable region sequences. Shown are dimers of each one heavy and one light chain variable region. As naturally occurring antibodies typically are tetramers, an antibody may comprise a combination of two of the depicted dimers.

FIG. 5 depicts the portions of the α-IL-18 receptor amino acid sequences that form the epitope for a specific antigen binding protein embodiment.

FIG. 6 depicts the complete AM$_H$6 heavy chain nucleotide and amino acid sequences (SEQ ID NOs:74 and 73, respectively). The arrow indicates the cleavage site of the leader sequence.

FIG. 7 depicts the complete AM$_L$12 light chain nucleotide and amino acid sequences (SEQ ID NOs:76 and 75, respectively). The arrow indicates the cleavage site of the leader sequence.

FIG. 8 depicts the complete AM$_H$4 heavy chain nucleotide and amino acid sequences (SEQ ID NOs:78 and 77, respectively). The arrow indicates the cleavage site of the leader sequence.

FIG. 9 depicts the complete AM$_L$14 light chain nucleotide and amino acid sequences (SEQ ID NOs:80 and 79, respectively). The arrow indicates the cleavage site of the leader sequence.

FIG. 10 depicts the complete AM$_H$9 heavy chain nucleotide and amino acid sequences (SEQ ID NOs:82 and 81, respectively). The arrow indicates the cleavage site of the leader sequence.

FIG. 11 depicts the complete AM$_L$9 light chain nucleotide and amino acid sequences (SEQ ID NOs:84 and 83, respectively). The arrow indicates the cleavage site of the leader sequence.

FIG. 12 depicts the complete AM$_H$11 heavy chain nucleotide and amino acid sequences (SEQ ID NOs:86 and 85, respectively). The arrow indicates the cleavage site of the leader sequence.

FIG. 13 depicts the complete AM$_L$7 light chain nucleotide and amino acid sequences (SEQ ID NOs:88 and 87, respectively). The arrow indicates the cleavage site of the leader sequence.

V. DETAILED DESCRIPTION OF PREFERRED EMBODIMENTS

The section headings used herein are for organizational purposes only and are not to be construed as limiting the subject matter described.

Standard techniques may be used for recombinant DNA, oligonucleotide synthesis, tissue culture and transformation, protein purification etc. Enzymatic reactions and purification techniques may be performed according to the manufacturer's specifications or as commonly accomplished in the art or as described herein. The following procedures and techniques may be generally performed according to conventional methods well known in the art and as described in various general and more specific references that are cited and discussed throughout the specification. See, e.g., Sambrook et al., 2001, *Molecular Cloning: A Laboratory Manual*, 3$^{rd}$ ed., Cold Spring Harbor Laboratory Press, Cold Spring Harbor, N.Y., which is incorporated herein by reference for any purpose. Unless specific definitions are provided, the nomenclature used in connection with, and the laboratory procedures and techniques of, analytical chemistry, organic chemistry, and medicinal and pharmaceutical chemistry described herein are those well known and commonly used in the art. Standard techniques may be used for chemical synthesis, chemical analyses, pharmaceutical preparation, formulation, and delivery and treatment of patients.

A. General Overview

Provided herein are antigen binding proteins that bind an α- or β-IL-18 receptor; the amino acid sequence of the human α- and β-IL-18 receptor are depicted in SEQ ID NOs:69 and 71, respectively. The antigen binding proteins of the invention comprise a scaffold structure with one or more complementarity-determining region (CDRs) as depicted in FIGS. 2A-2E, 3A and 3B, namely the CDRH1, CDRH2, CDRH3, CDRL1, CDRL2 and CDRL3 portion of SEQ ID NOs:1-34 (see, also SEQ ID NOs:89-292, depicting the amino acid sequences of the various CDRs). In certain embodiments, the scaffold structure of the antigen binding proteins is based on antibodies (including, but not limited to, monoclonal antibodies, human antibodies, murine antibodies, chimeric antibodies, humanized antibodies, bispecific antibodies), antibody fragments (such as minibodies, domain antibodies, F(ab) fragments, F(ab') fragments, F(ab)$_2$ fragments, F(ab')$_2$ fragments, Fv fragments, scFv fragments, Fd fragments), synthetic antibodies (sometimes referred to herein as "antibody mimetics"), antibody fusions (sometimes referred to as "antibody conjugates"), including Fc fusions. The various structures are further described and defined hereinbelow.

α- and β-IL-18 receptor antigen binding proteins are useful in treating conditions associated with IL-18 activity, including TH1-driven autoimmune diseases (WO2004/002519; WO2005/063290; WO2004/034988; Mallet et al., 2002, *Circ. Res.* 91:441-448), hepatic diseases (Finitto et al., 2004, *Liver* 53:392-400; Tsutsui et al., 2000, *Immunological Reviews* 174:192-209; Ludwiczek et al., 2002, *J. Clinical Immunology* 22:331-337), pancreatic diseases (Yoshida et al., 1998, *Anticancer Res.* 18:333-5), and cardiovascular diseases (Gerdes et al, 2002, *J. Exp. Med.* 195:245-257; WO03/080104; WO02/060479; WO01/85201; Raeburn et al., 2002, *Am. J. Physiol. Heart Circ. Physiol.* 283:H650-H657), as is further described below. Other uses for antigen binding proteins include, for example, diagnosis of IL-18 associated diseases or conditions and screening assays to determine the presence or absence of the α- or β-IL-18 receptor. Also provided are α- or β-IL-18 receptor antigen binding proteins, particularly antigen binding proteins that include at least one complementarity determining region (CDR) including heavy and/or light CDRs, as more fully described below, and combinations thereof.

The antigen binding proteins of the invention interfere with, block or modulate the interaction between IL-18 and the IL-18 receptor. In some embodiments, the antigen binding proteins interrupt the IL-18 pathway, thereby decreasing at least one biological activity of IL-18, including, but not limited to, induction of IFN-γ production, induction of killer cell formation, and enhancement of cytotoxicity of killer cells. As demonstrated in the Examples herein, antigen binding proteins that reduce IL-18 induced production of IFN-γ by KG cells include those comprising $AM_H8$ and $AM_L11$, $AM_H9$ and $AM_L9$, $AM_H10$ and $AM_L8$, $AM_H11$ and $AM_L7$, $AM_H15$ and $AM_L3$, $AM_H13$ and $AM_L4$, $AM_H13$ and $AM_L5$, $AM_H16$ and $AM_L2$, $AM_H2$ and $AM_L16$, $AM_H2$ and $AM_L17$, $AM_H1$ and $AM_L16$, $AM_H1$ and $AM_L17$, $AM_H4$ and $AM_L14$, $AM_H4$ and $AM_L15$, $AM_H3$ and $AM_L14$, $AM_H3$ and $AM_L15$, $AM_H6$ and $AM_L12$, $AM_H6$ and $AM_L13$, $AM_H5$ and $AM_L12$, and $AM_H5$ and $AM_L13$.

The antigen binding proteins of the invention thus may serve to identify conditions related to IL-18 or IL-18 receptor induced immune responses. In addition, the antigen binding proteins may be utilized to regulate and/or suppress IL-18 or IL-18 receptor mediated immune responses, as such having efficacy in the treatment and prevention of various diseases caused by excessive immune responses, e.g., inflammatory diseases. Accordingly, the α- and β-IL-18 receptor antigen binding proteins of the present invention can be used for the diagnosis, prevention or treatment of diseases or conditions associated with the IL-18 and IL-18 receptor mediated signal transduction pathway.

B. IL-18 Receptor Antigen Binding Proteins

In one aspect, antigen binding proteins that bind an α- or β-IL-18 receptor are provided. By "antigen binding protein" as used herein is meant a protein that specifically binds a specified antigen. In specific embodiments, the antigen is a human α- or β-IL-18 receptor.

By "protein," as used herein, is meant at least two covalently attached amino acids, which includes proteins, polypeptides, oligopeptides and peptides. In some embodiments, the two or more covalently attached amino acids are attached by a peptide bond. The protein may be made up of naturally occurring amino acids and peptide bonds, for example when the protein is made recombinantly using expression systems and host cells, as outlined below. Alternatively, the protein may include synthetic amino acids (e.g., homophenylalanine, citrulline, ornithine, and norleucine), or peptidomimetic structures, i.e., "peptide or protein analogs", such as peptoids (see, Simon et al., 1992, *Proc. Natl. Acad. Sci. U.S.A.* 89:9367, incorporated by reference herein), which can be resistant to proteases or other physiological and/or storage conditions. Such synthetic amino acids may be incorporated in particular when the antigen binding protein is synthesized in vitro by conventional methods well known in the art. In addition, any combination of peptidomimetic, synthetic and naturally occurring residues/structures can be used. "Amino acid" also includes imino acid residues such as proline and hydroxyproline. The amino acid "R group" or "side chain" may be in either the (L)- or the (D)-configuration. In a specific embodiment, the amino acids are in the (L)- or (D)-configuration.

In certain aspects, the invention provides recombinant antigen binding proteins that bind an IL-18 receptor, in some embodiments a human IL-18 receptor. In this context, a "recombinant protein" is a protein made using recombinant techniques, i.e., through the expression of a recombinant nucleic acid as described herein. Methods and techniques for the production of recombinant proteins are well known in the art.

In some embodiments, the antigen binding proteins are isolated proteins or substantially pure proteins. An "isolated" protein is unaccompanied by at least some of the material with which it is normally associated in its natural state, preferably constituting at least about 5%, more preferably at least about 50% by weight of the total protein in a given sample. A "substantially pure" protein comprises at least about 75% by weight of the total protein, with at least about 80% being preferred, and at least about 90% being particularly preferred. The definition includes the production of an antigen binding protein from one organism in a different organism or host cell. Alternatively, the protein may be made at a significantly higher concentration than is normally seen, through the use of an inducible promoter or high expression promoter, such that the protein is made at increased concentration levels.

The antigen binding proteins can specifically bind to an IL-18 receptor, preferably a human IL-18 receptor. "Specifically binds" as used herein means the equilibrium dissociation constant is at least $10^{-6}$ M, preferably $10^{-7}$ to $10^{-10}$ M, more preferably $<10^{-8}$ to $<10^{-10}$ M, even more preferably $<10^{-9}$ to $<10^{-10}$ M. In a specific embodiment, the antigen binding protein binds to a human IL-18 receptor having the amino acid sequence of SEQ ID NO:69 or 71. An epitope in the α- or β-IL-18 receptor to which preferred antigen binding proteins specifically bind is detailed below.

In embodiments where the antigen binding protein is used for therapeutic applications, an important characteristic of an IL-18 receptor antigen binding protein is whether it can inhibit, interfere with or modulate one or more biological activities of an IL-18 receptor. In this case, an antigen binding protein binds specifically and/or substantially inhibits binding of IL-18 to its receptor when an excess of antibody reduces the quantity of IL-18 bound to IL-18 receptor, or vice versa, by at least about 20%, 40%, 60%, 80%, 85%, or more (for example by measuring binding in an in vitro competitive binding assay). IL-18 receptor has many distinct biological effects, which can be measured in many different assays in different cell types. The ability of an IL-18 receptor antigen binding protein to inhibit, interfere with, or modulate the biological activity of IL-18 can be determined, for example, by measuring the inhibition of IFN-γ release in KG1 cells, as described in Example 4 or using a similar assay in which the ability of an antigen binding protein to inhibit IFN-γ release is measured.

Not every antigen binding protein that specifically binds to an antigen can block antigen binding to its normal ligand and thus inhibit or modulate the biological effects of the antigen. As is known in the art, such an effect can depend on what portion of the antigen the antigen binding protein binds to, and on both the absolute and the relative concentrations of the antigen and the antigen binding protein, in this case, an IL-18 receptor and the IL-18 receptor antigen binding protein. To be considered capable of inhibiting or modulating the biological activity of an IL-18 receptor as meant herein, an antigen binding protein may be able, for example, to inhibit the release of IFN-γ observed in the presence of IL-18, as measured in the KG1 cell assay of Example 4 or a similar assay, by at least about 20%, 40%, 60%, 80%, 85%, 90%, 95%, 99%, or more when the IL-18 concentration is within a range, for example, at about $EC_{80}$ or $EC_{90}$, where the effects of an agent that inhibits its biological activity can be readily apparent. An $EC_{80}$, as meant herein, is the amount of IL-18 required for 80% of the maximal effect of IL-18 to be observed. If the IL-18 concentration is well above $EC_{90}$, effects of an inhibiting agent may be less apparent due to the excess of IL-18. The concentration of an antigen binding protein required to inhibit, interfere with or modulate the biological activity of IL-18 receptor can vary widely and may depend upon how tightly the antibody binds to IL-18 receptor. For example, one molecule or less of an antigen binding protein per molecule of IL-18 may be sufficient to inhibit, interfere with or modulate biological activity in the KG1 cell assay. In some embodiments, a ratio of IL-18 receptor/antibody of about 1,000:1 to about 1:1,000, including about 2:1, 1:1, 1:2, 1:4, 1:6, 1:8, 1:10, 1:20, 1:40, 1:60, 1:100, 1:500, 1:1,000 or more may be required to inhibit, interfere with or modulate the biological activity of IL-18 receptor when the IL-18 concentration is from about $EC_{50}$ to about $EC_{90}$. Ratios of IL-18 receptor antigen binding protein between these values are also possible.

As a general structure, the antigen binding proteins of the invention comprise (a) a scaffold, and (b) one or a plurality of CDRs, regions that are determinative to antigen binding specificity and affinity. A "complementary determining region" or "CDR," as used herein, refers to a binding protein region that constitutes the major surface contact points for antigen binding. One or more CDRs are embedded in the scaffold structure of the antigen binding protein. The scaffold structure of the antigen binding proteins may be the framework of an antibody, or fragment or variant thereof, or may be completely synthetic in nature. The various scaffold structures of antigen binding proteins are further described hereinbelow.

1. CDRs

An antigen binding protein may have six CDRs (as typically does each "arm" of a naturally occurring antibody), for example one heavy chain CDR1 ("CDRH1"), one heavy chain CDR2 ("CDRH2"), one heavy chain CDR3 ("CDRH3"), one light chain CDR1 ("CDRL1"), one light chain CDR2 ("CDRL2"), one light chain CDR3 ("CDRL3"). The term "naturally occurring" as used throughout the specification in connection with biological materials such as polypeptides, nucleic acids, host cells, and the like, refers to materials which are found in nature. In naturally occurring antibodies, a CDRH1 typically comprises about five (5) to about seven (7) amino acids, CDRH2 typically comprises about sixteen (16) to about nineteen (19) amino acids, and CDRH3 typically comprises about three (3) to about twenty five (25) amino acids. CDRL1 typically comprises about ten (10) to about seventeen (17) amino acids, CDRL2 typically comprises about seven (7) amino acids, and CDRL3 typically comprises about seven (7) to about ten (10) amino acids. Preferred CDRs are depicted in FIGS. 2A-2E, 3A, and 3B.

The structure and properties of CDRs within a naturally occurring antibody are described further in this Section hereinbelow. Briefly, in a traditional antibody scaffold, the CDRs are embedded within a framework in the heavy and light chain variable region where they constitute the regions responsible for antigen binding and recognition. A variable region comprises at least three heavy or light chain CDRs, see, supra (Kabat et al., 1991, *Sequences of Proteins of Immunological Interest*, Public Health Service N.I.H., Bethesda, Md.; see also Chothia and Lesk, 1987, *J. Mol. Biol.* 196:901-917; Chothia et al., 1989, *Nature* 342: 877-883), within a framework region (designated framework regions 1-4, FR1, FR2, FR3, and FR4, by Kabat et al., 1991, supra; see also Chothia and Lesk, 1987, supra). See, infra. The CDRs provided by the present invention, however, may not only be used to define the antigen binding domain of a traditional antibody structure, but may be embedded in a variety of other scaffold structures, as described herein.

In certain embodiments, one or more CDRs of an antigen binding protein are each independently selected from the CDRH regions of any of SEQ ID NOs:89-139 and the CDRL regions of any of SEQ ID NOs:140-190. Thus, in one embodiment, the invention provides an antigen binding protein that binds an α- or β-IL-18 receptor, wherein said antigen binding protein comprises (a) a scaffold structure (as described below); and (b) at least one CDR selected from the CDRH regions of any of SEQ ID NOs:89-139 and the CDRL regions of any of SEQ ID NOs:140-190. In this embodiment, of particular use are antigen binding proteins with a CDRH3 or CDRL3 region. Additional embodiments utilize antigen binding proteins with one CDR selected from the CDRH regions of any of SEQ ID NOs:89-139 and a CDRL region of any of SEQ ID NOs:140-190 (e.g., the antigen binding protein has two CDR regions, one CDRH and one CDHL, a specific embodiment are antigen binding proteins with both a CDRH3 and a CDRL3 region).

As will be appreciated by those in the art, particularly useful embodiments may contain one, two, three, four, five or six of independently selected CDRs of SEQ ID NOs:89-190. However, as will be appreciated by those in the art, specific embodiments generally utilize combinations of CDRs that are non-repetitive, e.g., antigen binding proteins are generally not made with two CDRH2 regions, etc.

Figure 4:
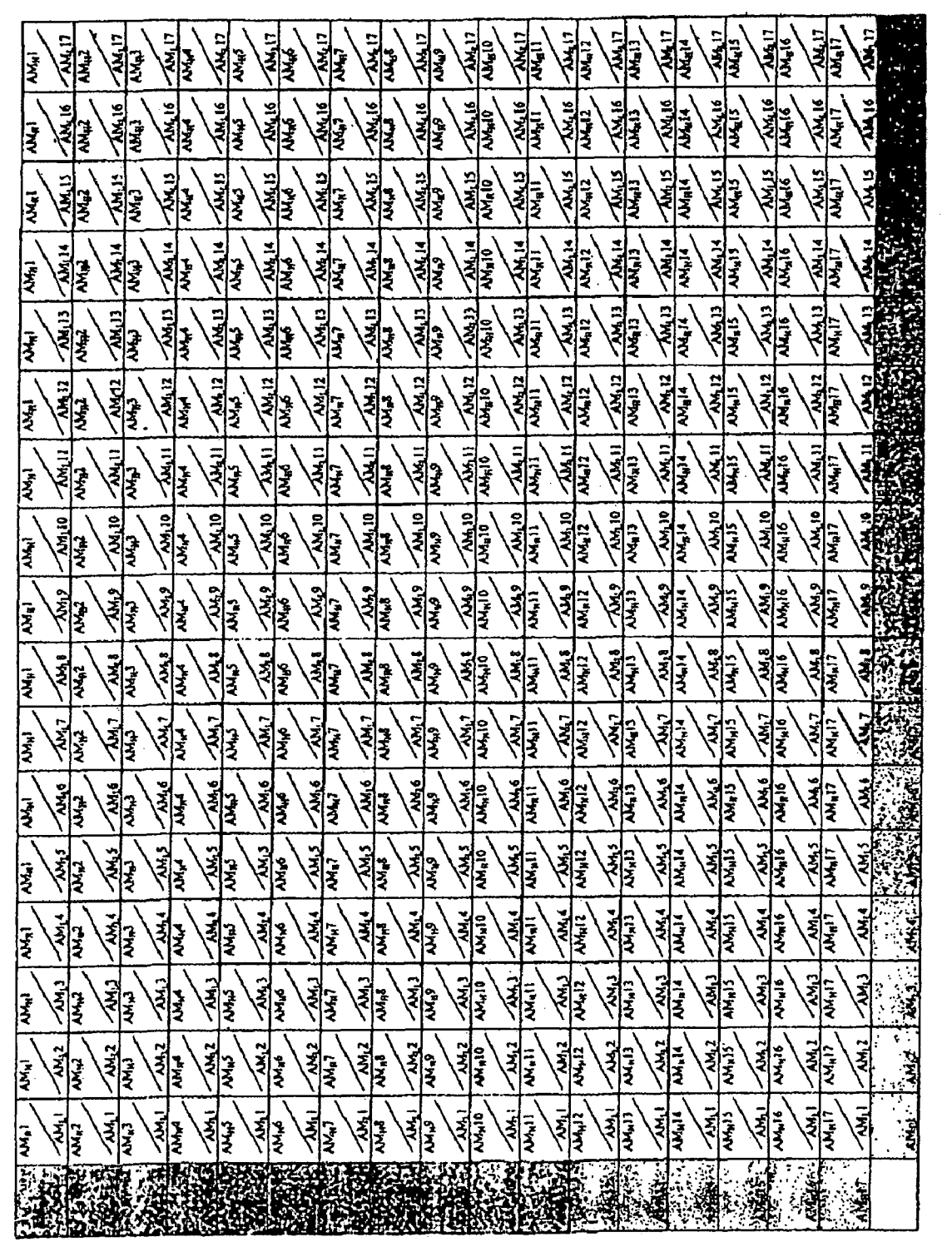

In some embodiments, antigen binding proteins are generated that comprise a CDRH3 region and a CDRL3 region, particularly with the CDRH3 region being selected from a CDRH3 region of any of SEQ ID NOs:91, 94, 97, 100, 103, 106, 109, 112, 115, 118, 121, 124, 127, 130, 133, 136, 139 and the CDRL3 region being selected from a CDRL3 region of any of SEQ ID NOs:142, 145, 148, 151, 154, 157, 160, 163, 166, 169, 172, 175, 178, 181, 184, 187, 190. Particular combinations are depicted in FIG. 4.

In additional embodiments, antigen binding proteins are utilized that comprise a CDRH1, a CDRH2, and a CDRH3 region independently selected from SEQ ID NOs:89-139. In more specific embodiments, of particular use may be antigen binding proteins of this type that have all three CDRH regions selected from the same variable region of any of SEQ ID NOs:1-17.

In further embodiments, antigen binding proteins are utilized that comprise a CDRL1, a CDRL2, and a CDRL3 region independently selected from SEQ ID NOs:140-190. In more specific embodiments, of particular use are antigen binding proteins of this type that have all three CDRL regions selected from the same variable region of any of SEQ ID NOs:18-34.

In an additional embodiment, the antigen binding protein comprises a CDRH1, CDRH2, and CDRH3 region independently selected from SEQ ID NOs:89-139, again, in one embodiment with all three regions selected from the same SEQ ID NO, and a CDRL1, CDRL2, and CDRL3 region independently selected from SEQ ID NOs:140-190, again, in one embodiment with all three regions selected from the same variable region of any of SEQ ID NOs:1-34.

In yet another aspect of the invention provides for an antigen binding protein that binds the α- or βIL-18 receptor where the isolated antigen binding protein comprises a heavy chain amino acid sequence that comprises a CDRH1, a CDRH2, or a CDRH3, each selected from any of SEQ ID NOs:89-139, or a fragment thereof, or a light chain amino acid sequence that comprises a CDRL1, a CDRL2, or a CDRL3, each selected from any of SEQ ID NOs:140-190, or a fragment thereof. A heavy or light chain variable region "fragment," as used herein includes at least one CDR and at least a portion of a framework region of an antibody framework of SEQ ID NOs:1-34, said portion comprising at least one amino acid.

In yet another aspect, the invention provides for an antigen binding protein that binds an α- or β-IL-18 receptor where the isolated antigen binding protein comprises a heavy chain amino acid sequence that comprises a CDRH1, a CDRH2, and a CDRH3, each independently selected from any of SEQ ID NOs:89-139, or a light chain amino acid sequence that comprises a CDRL1, a CDRL2, and a CDRL3, each independently selected from any of SEQ ID NOs:140-190. In a specific embodiment, the CDRs are from the same contiguous heavy chain amino acid sequence of SEQ ID NOs:1-17 or from the same contiguous light chain amino acid sequence of SEQ ID NOs:18-34.

A further aspect of the invention provides for an isolated antigen binding protein that binds an α- or β-IL-18 receptor where the isolated antigen binding protein comprises a heavy chain amino acid sequence that comprises a CDRH1, a CDRH2, and a CDRH3, each independently selected from any of SEQ ID NOs:89-139, and a light chain amino acid sequence that comprises a CDRL1, a CDRL2, and a CDRL3, each independently selected from any of SEQ ID NOs:140-190. In a specific embodiment, the heavy chain CDRs are from the same contiguous heavy chain amino acid sequence of SEQ ID NO:1-17 and the light chain CDRs are from the same contiguous light chain amino acid sequence of SEQ ID NO:18-34.

An additional aspect of the invention provides for an isolated antigen binding protein that binds an α- or β-IL-18 receptor where the isolated antigen binding protein comprises a heavy chain amino acid sequence of any of SEQ ID NOs:1-17, or a light chain amino acid sequence of any of SEQ ID NOs:18-34.

A further aspect of the invention provides for an isolated antigen binding protein that binds an α- or β-IL-18 receptor where the isolated antigen binding protein comprises a heavy chain amino acid sequence of any of SEQ ID NOs:1-17, and a light chain amino acid sequence of any of SEQ ID NOs:18-34. It is noted that the any the heavy chain sequences of SEQ ID NOs:1-17 can be mixed and matched with any of the light chain sequences of SEQ ID NOs:18-34. The resulting possible combinations are depicted in FIG. 4. Shown are dimers of a combination of each one heavy and one light chain variable region. As most antibodies are tetramers, an antigen binding protein of the invention may comprise any combination of any two of the depicted dimers thus including both hetero- and homo-tetramers, with homo-tetramers (e.g., two identical dimers) being specific.

In again a further aspect the antigen binding protein of the invention comprises any of the sequences depicted in SEQ ID NOs:73-88.

TABLE 1 provides a brief description of the sequences as they relate to their sequence identification numbers. The CDRs within the variable regions of the invention are identified in FIGS. 2A-2E, 3A and 3B.

TABLE 1

Brief Description Of Sequence Listings

| Brief Description | Sequence Identification Number |
|---|---|
| Amino acid sequence encoding the heavy chain variable region $AM_H1$ | SEQ ID NO: 1 |
| Amino acid sequence encoding the heavy chain variable region $AM_H2$ | SEQ ID NO: 2 |
| Amino acid sequence encoding the heavy chain variable region $AM_H3$ | SEQ ID NO: 3 |
| Amino acid sequence encoding the heavy chain variable region $AM_H4$ | SEQ ID NO: 4 |
| Amino acid sequence encoding the heavy chain variable region $AM_H5$ | SEQ ID NO: 5 |

TABLE 1-continued

Brief Description Of Sequence Listings

| Brief Description | Sequence Identification Number |
|---|---|
| Amino acid sequence encoding the heavy chain variable region $AM_H6$ | SEQ ID NO: 6 |
| Amino acid sequence encoding the heavy chain variable region $AM_H7$ | SEQ ID NO: 7 |
| Amino acid sequence encoding the heavy chain variable region $AM_H8$ | SEQ ID NO: 8 |
| Amino acid sequence encoding the heavy chain variable region $AM_H9$ | SEQ ID NO: 9 |
| Amino acid sequence encoding the heavy chain variable region $AM_H10$ | SEQ ID NO: 10 |
| Amino acid sequence encoding the heavy chain variable region $AM_H11$ | SEQ ID NO: 11 |
| Amino acid sequence encoding the heavy chain variable region $AM_H12$ | SEQ ID NO: 12 |
| Amino acid sequence encoding the heavy chain variable region $AM_H13$ | SEQ ID NO: 13 |
| Amino acid sequence encoding the heavy chain variable region $AM_H14$ | SEQ ID NO: 14 |
| Amino acid sequence encoding the heavy chain variable region $AM_H15$ | SEQ ID NO: 15 |
| Amino acid sequence encoding the heavy chain variable region $AM_H16$ | SEQ ID NO: 16 |
| Amino acid sequence encoding the heavy chain variable region $AM_H17$ | SEQ ID NO: 17 |
| Amino acid sequence encoding the light chain variable region $AM_L1$ | SEQ ID NO: 18 |
| Amino acid sequence encoding the light chain variable region $AM_L2$ | SEQ ID NO: 19 |
| Amino acid sequence encoding the light chain variable region $AM_L3$ | SEQ ID NO: 20 |
| Amino acid sequence encoding the light chain variable region $AM_L4$ | SEQ ID NO: 21 |
| Amino acid sequence encoding the light chain variable region $AM_L5$ | SEQ ID NO: 22 |
| Amino acid sequence encoding the light chain variable region $AM_L6$ | SEQ ID NO: 23 |
| Amino acid sequence encoding the light chain variable region $AM_L7$ | SEQ ID NO: 24 |
| Amino acid sequence encoding the light chain variable region $AM_L8$ | SEQ ID NO: 25 |
| Amino acid sequence encoding the light chain variable region $AM_L9$ | SEQ ID NO: 26 |
| Amino acid sequence encoding the light chain variable region $AM_L10$ | SEQ ID NO: 27 |
| Amino acid sequence encoding the light chain variable region $AM_L11$ | SEQ ID NO: 28 |
| Amino acid sequence encoding the light chain variable region $AM_L12$ | SEQ ID NO: 29 |
| Amino acid sequence encoding the light chain variable region $AM_L13$ | SEQ ID NO: 30 |
| Amino acid sequence encoding the light chain variable region $AM_L14$ | SEQ ID NO: 31 |
| Amino acid sequence encoding the light chain variable region $AM_L15$ | SEQ ID NO: 32 |
| Amino acid sequence encoding the light chain variable region $AM_L16$ | SEQ ID NO: 33 |
| Amino acid sequence encoding the light chain variable region $AM_L17$ | SEQ ID NO: 34 |
| Nucleotide sequence encoding the heavy chain variable region $AM_H1$ | SEQ ID NO: 35 |
| Nucleotide sequence encoding the heavy chain variable region $AM_H2$ | SEQ ID NO: 36 |
| Nucleotide sequence encoding the heavy chain variable region $AM_H3$ | SEQ ID NO: 37 |
| Nucleotide sequence encoding the heavy chain variable region $AM_H4$ | SEQ ID NO: 38 |
| Nucleotide sequence encoding the heavy chain variable region $AM_H5$ | SEQ ID NO: 39 |
| Nucleotide sequence encoding the heavy chain variable region $AM_H6$ | SEQ ID NO: 40 |
| Nucleotide sequence encoding the heavy chain variable region $AM_H7$ | SEQ ID NO: 41 |
| Nucleotide sequence encoding the heavy chain variable region $AM_H8$ | SEQ ID NO: 42 |
| Nucleotide sequence encoding the heavy chain variable region $AM_H9$ | SEQ ID NO: 43 |
| Nucleotide sequence encoding the heavy chain variable region $AM_H10$ | SEQ ID NO: 44 |
| Nucleotide sequence encoding the heavy chain variable region $AM_H11$ | SEQ ID NO: 45 |
| Nucleotide sequence encoding the heavy chain variable region $AM_H12$ | SEQ ID NO: 46 |
| Nucleotide sequence encoding the heavy chain variable region $AM_H13$ | SEQ ID NO: 47 |
| Nucleotide sequence encoding the heavy chain variable region $AM_H14$ | SEQ ID NO: 48 |
| Nucleotide sequence encoding the heavy chain variable region $AM_H15$ | SEQ ID NO: 49 |
| Nucleotide sequence encoding the heavy chain variable region $AM_H16$ | SEQ ID NO: 50 |
| Nucleotide sequence encoding the heavy chain variable region $AM_H17$ | SEQ ID NO: 51 |
| Nucleotide sequence encoding the light chain variable region $AM_L1$ | SEQ ID NO: 52 |
| Nucleotide sequence encoding the light chain variable region $AM_L2$ | SEQ ID NO: 53 |
| Nucleotide sequence encoding the light chain variable region $AM_L3$ | SEQ ID NO: 54 |
| Nucleotide sequence encoding the light chain variable region $AM_L4$ | SEQ ID NO: 55 |
| Nucleotide sequence encoding the light chain variable region $AM_L5$ | SEQ ID NO: 56 |
| Nucleotide sequence encoding the light chain variable region $AM_L6$ | SEQ ID NO: 57 |
| Nucleotide sequence encoding the light chain variable region $AM_L7$ | SEQ ID NO: 58 |
| Nucleotide sequence encoding the light chain variable region $AM_L8$ | SEQ ID NO: 59 |
| Nucleotide sequence encoding the light chain variable region $AM_L9$ | SEQ ID NO: 60 |
| Nucleotide sequence encoding the light chain variable region $AM_L10$ | SEQ ID NO: 61 |
| Nucleotide sequence encoding the light chain variable region $AM_L11$ | SEQ ID NO: 62 |
| Nucleotide sequence encoding the light chain variable region $AM_L12$ | SEQ ID NO: 63 |
| Nucleotide sequence encoding the light chain variable region $AM_L13$ | SEQ ID NO: 64 |
| Nucleotide sequence encoding the light chain variable region $AM_L14$ | SEQ ID NO: 65 |
| Nucleotide sequence encoding the light chain variable region $AM_L15$ | SEQ ID NO: 66 |
| Nucleotide sequence encoding the light chain variable region $AM_L16$ | SEQ ID NO: 67 |
| Nucleotide sequence encoding the light chain variable region $AM_L17$ | SEQ ID NO: 68 |
| Amino acid sequence of human α-IL-18 receptor | SEQ ID NO: 69 |
| Nucleotide sequence of human α-IL-18 receptor | SEQ ID NO: 70 |
| Amino acid sequence of human β-IL-18 receptor | SEQ ID NO: 71 |
| Nucleotide sequence of human β-IL-18 receptor | SEQ ID NO: 72 |
| Amino acid sequence of complete heavy chain of $AM_H6$ | SEQ ID NO: 73 |
| Nucleotide sequence of complete heavy chain of $AM_H6$ | SEQ ID NO: 74 |
| Amino acid sequence of complete light chain of $AM_L12$ | SEQ ID NO: 75 |
| Nucleotide sequence of complete light chain of $AM_L12$ | SEQ ID NO: 76 |
| Amino acid sequence of complete heavy chain of $AM_H4$ | SEQ ID NO: 77 |
| Nucleotide sequence of complete heavy chain of $AM_H4$ | SEQ ID NO: 78 |
| Amino acid sequence of complete light chain of $AM_L14$ | SEQ ID NO: 79 |
| Nucleotide sequence of complete light chain of $AM_L14$ | SEQ ID NO: 80 |

TABLE 1-continued

| Brief Description | Sequence Identification Number |
|---|---|
| Amino acid sequence of complete heavy chain of $AM_H9$ | SEQ ID NO: 81 |
| Nucleotide sequence of complete heavy chain of $AM_H9$ | SEQ ID NO: 82 |
| Amino acid sequence of complete light chain of $AM_L9$ | SEQ ID NO: 83 |
| Nucleotide sequence of complete light chain of $AM_L9$ | SEQ ID NO: 84 |
| Amino acid sequence of complete heavy chain of $AM_H11$ | SEQ ID NO: 85 |
| Nucleotide sequence of complete heavy chain of $AM_H11$ | SEQ ID NO: 86 |
| Amino acid sequence of complete light chain of $AM_L7$ | SEQ ID NO: 87 |
| Nucleotide sequence of complete light chain of $AM_L7$ | SEQ ID NO: 88 |
| Amino acid sequence encoding CDR1, CDR 2, CDR 3, respectively, of heavy chain variable region $AM_H1$ | SEQ ID NO: 89, 90, 91 |
| Amino acid sequence encoding CDR1, CDR 2, CDR 3, respectively, of heavy chain variable region $AM_H2$ | SEQ ID NO: 92, 93, 94 |
| Amino acid sequence encoding CDR1, CDR 2, CDR 3, respectively, of heavy chain variable region $AM_H3$ | SEQ ID NO: 95, 96, 97 |
| Amino acid sequence encoding CDR1, CDR 2, CDR 3, respectively, of heavy chain variable region $AM_H4$ | SEQ ID NO: 98, 99, 100 |
| Amino acid sequence encoding CDR1, CDR 2, CDR 3, respectively, of heavy chain variable region $AM_H5$ | SEQ ID NO: 101, 102, 103 |
| Amino acid sequence encoding CDR1, CDR 2, CDR 3, respectively, of heavy chain variable region $AM_H6$ | SEQ ID NO: 104, 105, 106 |
| Amino acid sequence encoding CDR1, CDR 2, CDR 3, respectively, of heavy chain variable region $AM_H7$ | SEQ ID NO: 107, 108, 109 |
| Amino acid sequence encoding CDR1, CDR 2, CDR 3, respectively, of heavy chain variable region $AM_H8$ | SEQ ID NO: 110, 111, 112 |
| Amino acid sequence encoding CDR1, CDR 2, CDR 3, respectively, of heavy chain variable region $AM_H9$ | SEQ ID NO: 113, 114, 115 |
| Amino acid sequence encoding CDR1, CDR 2, CDR 3, respectively, of heavy chain variable region $AM_H10$ | SEQ ID NO: 116, 117, 118 |
| Amino acid sequence encoding CDR1, CDR 2, CDR 3, respectively, of heavy chain variable region $AM_H11$ | SEQ ID NO: 119, 120, 121 |
| Amino acid sequence encoding CDR1, CDR 2, CDR 3, respectively, of heavy chain variable region $AM_H12$ | SEQ ID NO: 122, 123, 124 |
| Amino acid sequence encoding CDR1, CDR 2, CDR 3, respectively, of heavy chain variable region $AM_H13$ | SEQ ID NO: 125, 126, 127 |
| Amino acid sequence encoding CDR1, CDR 2, CDR 3, respectively, of heavy chain variable region $AM_H14$ | SEQ ID NO: 128, 129, 130 |
| Amino acid sequence encoding CDR1, CDR 2, CDR 3, respectively, of heavy chain variable region $AM_H15$ | SEQ ID NO: 131, 132, 133 |
| Amino acid sequence encoding CDR1, CDR 2, CDR 3, respectively, of heavy chain variable region $AM_H16$ | SEQ ID NO: 134, 135, 136 |
| Amino acid sequence encoding CDR1, CDR 2, CDR 3, respectively, of heavy chain variable region $AM_H17$ | SEQ ID NO: 137, 138, 139 |
| Amino acid sequence encoding CDR1, CDR 2, CDR 3, respectively, of light chain variable region $AM_L1$ | SEQ ID NO: 140, 141, 142 |
| Amino acid sequence encoding CDR1, CDR 2, CDR 3, respectively, of light chain variable region $AM_L2$ | SEQ ID NO: 143, 144, 145 |
| Amino acid sequence encoding CDR1, CDR 2, CDR 3, respectively, of light chain variable region $AM_L3$ | SEQ ID NO: 146, 147, 148 |
| Amino acid sequence encoding CDR1, CDR 2, CDR 3, respectively, of light chain variable region $AM_L4$ | SEQ ID NO: 149, 150, 151 |
| Amino acid sequence encoding CDR1, CDR 2, CDR 3, respectively, of light chain variable region $AM_L5$ | SEQ ID NO: 152, 153, 154 |
| Amino acid sequence encoding CDR1, CDR 2, CDR 3, respectively, of light chain variable region $AM_L6$ | SEQ ID NO: 155, 156, 157 |
| Amino acid sequence encoding CDR1, CDR 2, CDR 3, respectively, of light chain variable region $AM_L7$ | SEQ ID NO: 158, 159, 160 |
| Amino acid sequence encoding CDR1, CDR 2, CDR 3, respectively, of light chain variable region $AM_L8$ | SEQ ID NO: 161, 162, 163 |
| Amino acid sequence encoding CDR1, CDR 2, CDR 3, respectively, of light chain variable region $AM_L9$ | SEQ ID NO: 164, 165, 166 |
| Amino acid sequence encoding CDR1, CDR 2, CDR 3, respectively, of light chain variable region $AM_L10$ | SEQ ID NO: 167, 168, 169 |
| Amino acid sequence encoding CDR1, CDR 2, CDR 3, respectively, of light chain variable region $AM_L11$ | SEQ ID NO: 170, 171, 172 |
| Amino acid sequence encoding CDR1, CDR 2, CDR 3, respectively, of light chain variable region $AM_L12$ | SEQ ID NO: 173, 174, 175 |
| Amino acid sequence encoding CDR1, CDR 2, CDR 3, respectively, of light chain variable region $AM_L13$ | SEQ ID NO: 176, 177, 178 |
| Amino acid sequence encoding CDR1, CDR 2, CDR 3, respectively, of light chain variable region $AM_L14$ | SEQ ID NO: 179, 180, 181 |
| Amino acid sequence encoding CDR1, CDR 2, CDR 3, respectively, of light chain variable region $AM_L15$ | SEQ ID NO: 182, 183, 184 |
| Amino acid sequence encoding CDR1, CDR 2, CDR 3, respectively, of light chain variable region $AM_L16$ | SEQ ID NO: 185, 186, 187 |

TABLE 1-continued

Brief Description Of Sequence Listings

| Brief Description | Sequence Identification Number |
|---|---|
| Amino acid sequence encoding CDR1, CDR 2, CDR 3, respectively, of light chain variable region $AM_L17$ | SEQ ID NO: 188, 189, 190 |
| Nucleotide sequence encoding CDR1, CDR 2, CDR 3, respectively, of heavy chain variable region $AM_H1$ | SEQ ID NO: 191, 192, 193 |
| Nucleotide sequence encoding CDR1, CDR 2, CDR 3, respectively, of heavy chain variable region $AM_H2$ | SEQ ID NO: 194, 195, 196 |
| Nucleotide sequence encoding CDR1, CDR 2, CDR 3, respectively, of heavy chain variable region $AM_H3$ | SEQ ID NO: 197, 198, 199 |
| Nucleotide sequence encoding CDR1, CDR 2, CDR 3, respectively, of heavy chain variable region $AM_H4$ | SEQ ID NO: 200, 201, 202 |
| Nucleotide sequence encoding CDR1, CDR 2, CDR 3, respectively, of heavy chain variable region $AM_H5$ | SEQ ID NO: 203, 204, 205 |
| Nucleotide sequence encoding CDR1, CDR 2, CDR 3, respectively, of heavy chain variable region $AM_H6$ | SEQ ID NO: 206, 207, 208 |
| Nucleotide sequence encoding CDR1, CDR 2, CDR 3, respectively, of heavy chain variable region $AM_H7$ | SEQ ID NO: 209, 210, 211 |
| Nucleotide sequence encoding CDR1, CDR 2, CDR 3, respectively, of heavy chain variable region $AM_H8$ | SEQ ID NO: 212, 213, 214 |
| Nucleotide sequence encoding CDR1, CDR 2, CDR 3, respectively, of heavy chain variable region $AM_H9$ | SEQ ID NO: 215, 216, 217 |
| Nucleotide sequence encoding CDR1, CDR 2, CDR 3, respectively, of heavy chain variable region $AM_H10$ | SEQ ID NO: 218, 219, 220 |
| Nucleotide sequence encoding CDR1, CDR 2, CDR 3, respectively, of heavy chain variable region $AM_H11$ | SEQ ID NO: 221, 222, 223 |
| Nucleotide sequence encoding CDR1, CDR 2, CDR 3, respectively, of heavy chain variable region $AM_H12$ | SEQ ID NO: 224, 225, 226 |
| Nucleotide sequence encoding CDR1, CDR 2, CDR 3, respectively, of heavy chain variable region $AM_H13$ | SEQ ID NO: 227, 228, 229 |
| Nucleotide sequence encoding CDR1, CDR 2, CDR 3, respectively, of heavy chain variable region $AM_H14$ | SEQ ID NO: 230, 231, 232 |
| Nucleotide sequence encoding CDR1, CDR 2, CDR 3, respectively, of heavy chain variable region $AM_H15$ | SEQ ID NO: 233, 234, 235 |
| Nucleotide sequence encoding CDR1, CDR 2, CDR 3, respectively, of heavy chain variable region $AM_H16$ | SEQ ID NO: 236, 237, 238 |
| Nucleotide sequence encoding CDR1, CDR 2, CDR 3, respectively, of heavy chain variable region $AM_H17$ | SEQ ID NO: 239, 240, 241 |
| Nucleotide sequence encoding CDR1, CDR 2, CDR 3, respectively, of light chain variable region $AM_L1$ | SEQ ID NO: 242, 243, 244 |
| Nucleotide sequence encoding CDR1, CDR 2, CDR 3, respectively, of light chain variable region $AM_L2$ | SEQ ID NO: 245, 246, 247 |
| Nucleotide sequence encoding CDR1, CDR 2, CDR 3, respectively, of light chain variable region $AM_L3$ | SEQ ID NO: 248, 249, 250 |
| Nucleotide sequence encoding CDR1, CDR 2, CDR 3, respectively, of light chain variable region $AM_L4$ | SEQ ID NO: 251, 252, 253 |
| Nucleotide sequence encoding CDR1, CDR 2, CDR 3, respectively, of light chain variable region $AM_L5$ | SEQ ID NO: 254, 255, 256 |
| Nucleotide sequence encoding CDR1, CDR 2, CDR 3, respectively, of light chain variable region $AM_L6$ | SEQ ID NO: 257, 258, 259 |
| Nucleotide sequence encoding CDR1, CDR 2, CDR 3, respectively, of light chain variable region $AM_L7$ | SEQ ID NO: 260, 261, 262 |
| Nucleotide sequence encoding CDR1, CDR 2, CDR 3, respectively, of light chain variable region $AM_L8$ | SEQ ID NO: 263, 264, 265 |
| Nucleotide sequence encoding CDR1, CDR 2, CDR 3, respectively, of light chain variable region $AM_L9$ | SEQ ID NO: 266, 267, 268 |
| Nucleotide sequence encoding CDR1, CDR 2, CDR 3, respectively, of light chain variable region $AM_L10$ | SEQ ID NO: 269, 270, 271 |
| Nucleotide sequence encoding CDR1, CDR 2, CDR 3, respectively, of light chain variable region $AM_L11$ | SEQ ID NO: 272, 273, 274 |
| Nucleotide sequence encoding CDR1, CDR 2, CDR 3, respectively, of light chain variable region $AM_L12$ | SEQ ID NO: 275, 276, 277 |
| Nucleotide sequence encoding CDR1, CDR 2, CDR 3, respectively, of light chain variable region $AM_L13$ | SEQ ID NO: 278, 279, 280 |
| Nucleotide sequence encoding CDR1, CDR 2, CDR 3, respectively, of light chain variable region $AM_L14$ | SEQ ID NO: 281, 282, 283 |
| Nucleotide sequence encoding CDR1, CDR 2, CDR 3, respectively, of light chain variable region $AM_L15$ | SEQ ID NO: 284, 285, 286 |
| Nucleotide sequence encoding CDR1, CDR 2, CDR 3, respectively, of light chain variable region $AM_L16$ | SEQ ID NO: 287, 288, 289 |
| Nucleotide sequence encoding CDR1, CDR 2, CDR 3, respectively, of light chain variable region $AM_L17$ | SEQ ID NO: 290, 291, 292 |

2. Scaffolds

As noted herein, the antigen binding proteins can comprise a scaffold structure into which the CDR(s) are grafted. The scaffold structure may be based on antibodies (including, but not limited to, monoclonal antibodies, human antibodies, murine antibodies, chimeric antibodies, humanized antibodies, bispecific antibodies), antibody fragments (such as minibodies, domain antibodies, F(ab) fragments, F(ab') fragments, F(ab)$_2$ fragments, F(ab')$_2$ fragments, Fv fragments, scFv fragments, Fd fragments), synthetic antibodies (sometimes referred to herein as "antibody mimetics"), antibody fusions (sometimes referred to as "antibody conjugates"), including Fc fusions. Some embodiments include the use of human scaffold components. The invention as such at least encompasses any of the below described scaffolds comprising one or several of the CDRs as identified in SEQ ID NOs:89-190, preferably of SEQ ID NOs:89-189, that can bind to and/or inhibit the biological activity of IL-18 receptor. In some embodiments, the scaffold comprises one or several heavy chain variable regions as identified in SEQ ID NOs:1-17, and or one or several light chain variable regions as identified in any of SEQ ID NOs:18-34. In some embodiments, the scaffold comprises an IgG chain as identified in any of SEQ ID NOs:77-88.

In one embodiment, the scaffold into which one or several CDRs are grafted is an antibody. As used herein, the term "antibody" refers to a multimeric protein having a traditional antibody structure, comprising at least two, more typically four polypeptide chains. An antibody binds specifically to an antigen and may be able to inhibit or modulate the biological activity of the antigen. In certain embodiments, antibodies are produced by recombinant DNA techniques. In additional embodiments, antibodies are produced by enzymatic or chemical cleavage of naturally occurring antibodies.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2.

Within light and heavy chains, the variable and constant regions are joined by a "J" region of about twelve (12) or more amino acids, with the heavy chain also including a "D" region of about ten (10) more amino acids. See, generally, Paul, W., ed., 1989, Fundamental Immunology Ch. 7, 2nd ed. Raven Press, N.Y. The variable regions of each light/heavy chain pair form the antibody binding site.

Some naturally occurring antibodies, for example found in camels and llamas, are dimers consisting of two heavy chain and include no light chains. Muldermans et al., 2001, *J. Biotechnol.* 74:277-302; Desmyter et al., 2001, *J. Biol. Chem.* 276:26285-26290. Crystallographic studies of a camel antibody have revealed that the CDR3 regions form a surface that interacts with the antigen and thus is critical for antigen binding like in the more typical tetrameric antibodies.

The variable regions of the heavy and light chains typically exhibit the same general structure of relatively conserved framework regions (FR) joined by three hypervariable regions, also called complementarity determining regions or CDRs. The CDRs are the hypervariable regions of an antibody (or antigen binding protein, as outlined herein), which are responsible for antigen recognition and binding. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest. Chothia et al., 1987, *J. Mol. Biol.* 196:901-917; Chothia et al., 1989, *Nature* 342:878-883.

CDRs constitute the major surface contact points for antigen binding. See, e.g., Chothia and Lesk, 1987, *J. Mol. Biol.* 196:901-917. Further, CDR3 of the light chain and, especially, CDR3 of the heavy chain may constitute the most important determinants in antigen binding within the light and heavy chain variable regions. See, e.g., Chothia and Lesk, 1987, supra; Desiderio et al., 2001, *J. Mol. Biol.* 310:603-615; Xu and Davis, 2000, *Immunity* 13:37-45; Desmyter et al., 2001, *J. Biol. Chem.* 276:26285-26290; and Muyldermans, 2001, *J. Biotechnol.* 74:277-302. In some antibodies, the heavy chain CDR3 appears to constitute the major area of contact between the antigen and the antibody. Desmyter et al., 2001, supra. In vitro selection schemes in which CDR3 alone is varied can be used to vary the binding properties of an antibody. Muyldermans, 2001, supra; Desiderio et al., 2001, supra.

Naturally occurring antibody chains typically include a signal sequence, which directs the antibody chain into the cellular pathway for protein secretion and which is not present in the mature antibody. A polynucleotide encoding an antibody chain may encode a naturally occurring signal sequence or a heterologous signal sequence as described below.

In one embodiment, the antigen binding protein is a monoclonal antibody, with from one (1) to six (6) of the depicted CDRs of any of SEQ ID NOs:89-190, as outlined herein. The antibodies of the invention may be of any type including IgM, IgG (including IgG1, IgG2, IgG3, IgG4), IgD, IgA, or IgE antibody. In specific embodiment, the antigen binding protein is an IgG type antibody. In an even more specific embodiment, the antigen binding protein is an IgG2 type antibody.

In some embodiments, for example when the antigen binding protein is an antibody with complete heavy and light chains, the CDRs are all from the same species, e.g., human. In some embodiments, however, the scaffold components can be a mixture from different species. As such, if the antigen binding protein is an antibody, such antibody may be a chimeric antibody and/or a humanized antibody. In general, both "chimeric antibodies" refer to antibodies that combine regions from more than one species. For example, "chimeric antibodies" traditionally comprise variable region(s) from a mouse (or rat, in some cases) and the constant region(s) from a human.

For example in embodiments wherein the antigen binding protein contains less than six CDRs from the sequences outlined above, additional CDRs may be either from other species (e.g., murine CDRs), or may be different human CDRs than those depicted in the sequences. For example, human CDRH3 and CDRL3 regions from the appropriate sequences identified herein may be used, with CDRH1, CDRH2, CDRL1 and CDRL2 being optionally selected from alternate species, or different human antibody sequences, or combinations thereof. For example, the CDRs of the invention can replace the CDR regions of commercially relevant chimeric or humanized antibodies.

Specific embodiments of the invention utilize scaffold components of the antigen binding proteins that are human components.

"Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, Nature 321:522-525, Verhoeyen et al., 1988, Science 239: 1534-1536. Humanized antibodies can also be generated using mice with a genetically engineered immune system. Roque et al., 2004, Biotechnol. Prog. 20:639-654. In the present invention, the identified CDRs are human, and thus both humanized and chimeric antibodies in this context include some non-human CDRs; for example, humanized antibodies may be generated that comprise the CDRH3 and CDRL3 regions, with one or more of the other CDR regions being of a different special origin.

In one embodiment, the IL-18 antigen binding protein is a multispecific antibody, and notably a bispecific antibody, also sometimes referred to as "diabodies". These are antibodies that bind to two (or more) different antigens. Diabodies can be manufactured in a variety of ways known in the art (Holliger and Winter, 1993, Current Opinion Biotechnol. 4:446-449), e.g., prepared chemically or from hybrid hybridomas.

In one embodiment, the IL-18 antigen binding protein is a fully human antibody, i.e., an antibody fully composed of human components. In this embodiment, as outlined above, specific structures comprise complete heavy and light chains depicted comprising the CDR regions depicted in FIGS. 2A-2E, 3A and 3B. Additional embodiments utilize one or more of the CDRs of the invention, with the other CDRs, framework regions, J and D regions, constant regions, etc., coming from other human antibodies. For example, the CDRs of the invention can replace the CDRs of any number of human antibodies, particularly commercially relevant antibodies.

In one embodiment, the IL-18 antigen binding protein is an antibody fragment, that is a fragment of any of the antibodies outlined herein that retain binding specificity to an α- or β-18 receptor.

Specific antibody fragments include, but are not limited to, (i) the Fab fragment consisting of VL, VH, CL and CH1 domains, (ii) the Fab' fragment consisting of VL, VH, CL and CH1 domains plus the heavy chain hinge region; (ii) the Fd fragment consisting of the VH and CH1 domains, (iii) the Fv fragment consisting of the VL and VH domains of a single antibody; (iv) the dAb fragment (Ward et al., 1989, Nature 341:544-546) which consists of a single variable, (v) isolated CDR regions, (vi) F(ab')$_2$ fragments, a bivalent fragment comprising two linked Fab' fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883), (viii) bispecific single chain Fv dimers (PCT/US92/09965) and (ix) "diabodies" or "triabodies", multivalent or multispecific fragments constructed by gene fusion (Tomlinson et. al., 2000, Methods Enzymol. 326: 461-479; WO94/13804; Holliger et al., 1993, Proc. Natl. Acad. Sci. U.S.A. 90:6444-6448). The antibody fragments may be modified. For example, the molecules may be stabilized by the incorporation of disulphide bridges linking the VH and VL domains (Reiter et al., 1996, Nature Biotech. 14:1239-1245). Again, as outlined herein, the non-CDR components of these fragments are preferably human sequences.

In one embodiment, the IL-18 antigen binding protein is a minibody. Minibodies are minimized antibody-like proteins comprising a scFv joined to a CH3 domain. Hu et al., 1996, Cancer Res. 56:3055-3061.

In one embodiment, the IL-18 antigen binding protein is a domain antibody; see for example U.S. Pat. No. 6,248,516. Domain antibodies (dAbs) are functional binding domains of antibodies, corresponding to the variable regions of either the heavy (VH) or light (VL) chains of human antibodies dABs have a molecular weight of approximately 13 kDa, or less than one-tenth the size of a full antibody. dABs are well expressed in a variety of hosts including bacterial, yeast, and mammalian cell systems. In addition, dAbs are highly stable and retain activity even after being subjected to harsh conditions, such as freeze-drying or heat denaturation. See, for example, U.S. Pat. Nos. 6,291,158; 6,582,915; 6,593,081; 6,172,197; US Serial No. 2004/0110941; European Patent 0368684; U.S. Pat. No. 6,696,245, WO04/058821, WO04/003019 and WO03/002609.

In one embodiment, the IL-18 antigen binding protein is an antibody fusion protein or an antibody fragment fusion, such as an Fc fusion (sometimes collectively referred to herein as an "antibody conjugate"). The conjugate partner can be proteinaceous or non-proteinaceous; the latter generally being generated using functional groups on the antigen binding protein (see the discussion on covalent modifications of the antigen binding proteins) and on the conjugate partner. For example linkers are known in the art; for example, homo- or hetero-bifunctional linkers as are well known (see, 1994 Pierce Chemical Company catalog, technical section on cross-linkers, pages 155-200, incorporated herein by reference).

Suitable conjugates include, but are not limited to, labels as described below, drugs and cytotoxic agents including, but not limited to, cytotoxic drugs (e.g., chemotherapeutic agents) or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antigen binding proteins, or binding of a radionuclide to a chelating agent that has been covalently attached to the antigen binding protein. Additional embodiments utilize calicheamicin, auristatins, geldanamycin and maytansine.

In one embodiment, the IL-18 antigen binding protein is an antibody analog, sometimes referred to as "synthetic antibodies." For example, a variety of recent work utilizes either alternative protein scaffolds or artificial scaffolds with grafted CDRs. Such scaffolds include, but are not limited to, mutations introduced to stabilize the three-dimensional structure of the binding protein as well as wholly synthetic scaffolds consisting for example of biocompatible polymers. See, for example, Korndorfer et al., 2003, Proteins: Structure, Function, and Bioinformatics, Volume 53, Issue 1:121-129. Roque et al., 2004, Biotechnol. Prog. 20:639-654. In addition, peptide antibody mimetics ("PAMs") can be used, as well as scaffolds based on antibody mimetics utilizing fibronection components as a scaffold. Alternate scaffolds that may be used to produce an IL-18 antigen binding protein are reviewed in Hey et al., 2005, *Trends Biotechnol.* 23:514-22 and Binz et al., *Nature Biotechnology* 23:1257-68 (both incorporated herein by reference in their entirety).

3. CDR Variants

Also included within the invention are variants of the CDRH1, CDRH2, CDRH3, CDRL1, CDRL2 and CDRL3 amino acid sequences depicted in SEQ ID NOs:89-190. Thus variant CDRs are included within the definition of CDR as used herein. These variants fall into one or more of three classes: substitutional, insertional or deletional variants, with the former being specific.

As it is known in the art, a number of different programs can be used to identify the degree of sequence identity or similarity a protein or nucleic acid has to a known sequence.

For amino acid sequences, sequence identity and/or similarity is determined by using standard techniques known in the art, including, but not limited to, the local sequence identity algorithm of Smith and Waterman, 1981, *Adv. Appl. Math.* 2:482, the sequence identity alignment algorithm of Needleman and Wunsch, 1970, *J. Mol. Biol.* 48:443, the search for similarity method of Pearson and Lipman, 1988, *Proc. Nat. Acad. Sci. U.S.A.* 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., 1984, *Nucl. Acid Res.* 12:387-395, preferably using the default settings, or by inspection. Preferably, percent identity is calculated by FastDB based upon the following parameters: mismatch penalty of 1; gap penalty of 1; gap size penalty of 0.33; and joining penalty of 30, *"Current Methods in Sequence Comparison and Analysis,"* Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, 1987, *J. Mol. Evol.* 35:351-360; the method is similar to that described by Higgins and Sharp, 1989, *CABIOS* 5:151-153. Useful PILEUP parameters including a default gap weight of 3.00, a default gap length weight of 0.10, and weighted end gaps.

Another example of a useful algorithm is the BLAST algorithm, described in: Altschul et al., 1990, *J. Mol. Biol.* 215: 403-410; Altschul et al., 1997, *Nucleic Acids Res.* 25:3389-3402; and Karin et al., 1993, *Proc. Natl. Acad. Sci. U.S.A.* 90:5873-5787. A particularly useful BLAST program is the WU-BLAST-2 program which was obtained from Altschul et al., 1996, *Methods in Enzymology* 266:460-480. WU-BLAST-2 uses several search parameters, most of which are set to the default values. The adjustable parameters are set with the following values: overlap span=1, overlap fraction=0.125, word threshold (T)=II. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., 1993, *Nucl. Acids Res.* 25:3389-3402. Gapped BLAST uses BLOSUM-62 substitution scores; threshold T parameter set to 9; the two-hit method to trigger ungapped extensions, charges gap lengths of k a cost of 10+k; $X_u$ set to 16, and $X_g$ set to 40 for database search stage and to 67 for the output stage of the algorithms. Gapped alignments are triggered by a score corresponding to about 22 bits.

Generally, the amino acid homology, similarity, or identity between individual variant CDRs are at least 80% to the sequences depicted herein, and more typically with preferably increasing homologies or identities of at least 85%, 90%, 91%, 92%, 93%, 94%, 95%, 96%, 97%, 98%, 99%, and almost 100%.

In a similar manner, "percent (%) nucleic acid sequence identity" with respect to the nucleic acid sequence of the binding proteins identified herein is defined as the percentage of nucleotide residues in a candidate sequence that are identical with the nucleotide residues in the coding sequence of the antigen binding protein. A specific method utilizes the BLASTN module of WU-BLAST-2 set to the default parameters, with overlap span and overlap fraction set to 1 and 0.125, respectively.

Generally, the nucleic acid sequence homology, similarity, or identity between the nucleotide sequences encoding individual variant CDRs and the nucleotide sequences depicted herein are at least 60%, and more typically with preferably increasing homologies or identities of at least 65%, 70%, 75%, 80%, 85%, 90%, 91%, 92%, 93%, 94%, 95%, 96%, 97%, 98%, 99%, and almost 100%.

Homology between nucleotide sequences is often defined by their ability to hybridize to each other. The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein.

High stringency conditions are known in the art; see, for example Sambrook et al., 2001, supra, and *Short Protocols in Molecular Biology*, Second Edition, Ausubel et al. eds., John Wiley & Sons, 1992, both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, *Techniques In Biochemistry and Molecular Biology—Hybridization with Nucleic Acid Probes*, "Overview of principles of hybridization and the strategy of nucleic acid assays" (1993).

Generally, stringent conditions are selected to be about 5-10° C. lower than the thermal melting point (Tm) for the specific sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium Ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see, Sambrook et al., 2001, supra; Ausubel et al., 1992, supra, and Tijssen, 1993, supra.

The variants according to the invention are ordinarily prepared by site specific mutagenesis of nucleotides in the DNA encoding the antigen binding protein, using cassette or PCR mutagenesis or other techniques well known in the art, to produce DNA encoding the variant, and thereafter expressing the recombinant DNA in cell culture as outlined herein. However, antigen binding protein fragments comprising variant CDRs having up to about 100-150 residues may be prepared by in vitro synthesis using established techniques. The variants typically exhibit the same qualitative biological activity as the naturally occurring analogue, e.g., binding to IL-18 receptor and inhibiting signaling, although variants can also be selected which have modified characteristics as will be more fully outlined below.

Thus, a "variant CDR" is one with the specified homology, similarity, or identity to the parent CDR of the invention, and shares biological function, including, but not limited to, at least 90, 91, 92, 93, 94, 95, 96, 97, 98% or 99% of the specificity and/or activity of the parent CDR. For example, the variants typically will bind to the same IL-18 receptor epitope outlined below, with a similar inhibition of IL-18 receptor signaling.

While the site or region for introducing an amino acid sequence variation is predetermined, the mutation per se need not be predetermined. For example, in order to optimize the performance of a mutation at a given site, random mutagenesis may be conducted at the target codon or region and the expressed antigen binding protein CDR variants screened for the optimal combination of desired activity. Techniques for making substitution mutations at predetermined sites in DNA having a known sequence are well known, for example, M13 primer mutagenesis and PCR mutagenesis. Screening of the mutants is done using assays of antigen binding protein activities, such as IL-18 receptor binding.

Amino acid substitutions are typically of single residues; insertions usually will be on the order of from about one (1) to about twenty (20) amino acid residues, although considerably larger insertions may be tolerated. Deletions range from about one (1) to about twenty (20) amino acid residues, although in some cases deletions may be much larger.

Substitutions, deletions, insertions or any combination thereof may be used to arrive at a final derivative or variant. Generally these changes are done on a few amino acids to minimize the alteration of the molecule, particularly the immunogenicity and specificity of the antigen binding protein. However, larger changes may be tolerated in certain circumstances. When small alterations in the characteristics of the CDR of the antigen binding protein are desired, substitutions are generally made in accordance with the following chart depicted as TABLE 2.

TABLE 2

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |

TABLE 2-continued

| Original Residue | Exemplary Substitutions |
| --- | --- |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in TABLE 2. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The variants typically exhibit the same qualitative biological activity and will elicit the same immune response as the naturally-occurring analogue, although variants also are selected to modify the characteristics of the antigen binding protein proteins as needed. Alternatively, the variant may be designed such that the biological activity of the antigen binding protein is altered. For example, glycosylation sites may be altered or removed as discussed herein.

4. VH And VL Variants

As outlined above, in some embodiments the invention provides antigen binding proteins comprising, or consisting of, a heavy chain variable region of SEQ ID NO:1, 2, 3, 4, 5, 6, 7, 8, 9, 10, 11, 12, 13, 14, 15, 16, or 17 and/or a light chain variable region of SEQ ID NO:18, 19, 20, 21, 22, 23, 24, 25, 26, 27, 28, 29, 30, 31, 32, 33, or 34, respectively, or fragments thereof as defined above. Thus, in those embodiments, the antigen binding protein comprises not only at least one CDR or variant thereof depicted in SEQ ID NOs:1-34, but also at least part of a depicted framework sequence. In addition, the invention encompasses variants of such heavy chain variable sequences or light chain variable sequences.

A "variant VH" or "variant heavy chain variable region," and a "variant VL" or "variant light chain variable region" generally shares an amino acid homology, similarity, or identity of at least 80% with those depicted herein, and more typically with preferably increasing homologies or identities of at least 85%, 90%, 91%, 92%, 93%, 94%, 95%, 96%, 97%, 98%, 99% and almost 100%. The nucleic acid sequence homology, similarity, or identity between the nucleotide sequences encoding individual variant VHs and VLs and the nucleic acid sequences depicted herein are at least 60% with those depicted herein, and more typically with preferably increasing homologies or identities of at least 65%, 70%, 75%, 80%, 85%, 90%, 91%, 92%, 93%, 94%, 95%, 96%, 97%, 98%, 99% and almost 100%. In addition, a "variant VH" or "variant heavy chain variable region," and a "variant VL" or "variant light chain variable region" typically shares the biological function, including, but not limited to, at least 90, 91, 92, 93, 94, 95, 96, 97, 98% or 99% of the specificity and/or activity of the parent CDR. For example, the variants typically will bind to the same IL-18 receptor epitopes outlined below, with a similar inhibition of IL-18 receptor signaling.

Methods of generating variants, as well as methods of determining sequence homology, similarity, and identity, are outlined supra, see Section V.B.1.

In some embodiments, constant region variants may also be included. Preferred constant region variants include those that alter a biological function of the antibody containing the variation. For example, the antibody may contain a variation that alters the antibody's ability to activate complement or induce antibody-dependent cellular cytotoxicity (ADCC). Such variants may include those that result in an alteration of the glycosylation of the antibody.

C. IL-18 Receptor and IL-18 Receptor Epitopes

By "IL-18 receptor" or "IL-18R" herein is meant the cell surface receptor that binds to a ligand, including, but not limited to, IL-18 and as a result initiates a signal transduction pathway within the cell. The IL-18 receptor complex is made up of an IL-18 binding chain termed "α-IL-18 receptor" (α-IL-18R) or "IL-18Rα chain," and a signaling chain, termed β-IL-18 receptor "β-IL-18 receptor" (β-IL-18R") or "IL-18Rβ chain." As used herein, the term "IL-18 receptor" collectively refers to both the α- and the β-IL-18 receptor.

The antigen binding proteins disclosed herein bind to the IL-18Rα chain, the human amino acid sequence of which is depicted in SEQ ID NO:69 (its nucleic acid sequence is depicted in SEQ ID NO:70), or the IL-18Rβ chain, the human amino acid sequence of which is depicted in SEQ ID NO:71 (its nucleic acid sequence is depicted in SEQ ID NO:72). In a specific embodiment, the IL-18 receptor is human, although in some cases, other species may be used. In addition, as described below, IL-18 receptor proteins may also include fragments.

As is described below, binding of antigen binding proteins to specific epitopes is specific.

By "epitope", "antigenic determinant", and grammatical equivalents herein are meant a region of an antigen, e.g., IL-18 receptor, which can be specifically bound by an antigen binding protein. As the skilled artisan will appreciate, an epitope can be linear or conformational. "Linear epitope" refers to an epitope comprising a sequence of at least about five (5) and not more than about twenty (20) amino acids connected in a linear fashion, which amino acids, by themselves or as part of a larger sequence, bind to an antigen binding protein of the invention. "Conformational epitope" refers to an epitope whose three dimensional, secondary and/or tertiary structure can be a substantial aspect of antibody binding. Generally but not uniformly, amino acids that comprise a conformational epitope do not comprise a linear sequence of a protein's primary structure. Thus, a conformational epitope may be shared by proteins having non-homologous linear amino acid sequences. Without being bound by theory, a conformational epitope can be shared because the tertiary structure recognized by an antibody can be shared between two or more amino acid sequences. In one embodiment, suitable IL-18 receptor epitopes include any which are recognized by the antigen binding proteins of the present invention.

The invention provides antigen binding proteins recognizing and binding to a conformational epitope in the third Ig domain of human IL-18Rα, in particular, the region defined by amino acid residues 243-271, made up by amino acid residues 250-253 (i.e., residues MFGE) and amino acid residues 267-271 (i.e., residues MRIMT) of SEQ ID NO:69. The amino acid structure of this epitope is depicted in FIG. 5. Antigen binding proteins that bind to this epitope are particularly effective at blocking the interaction of IL-18 with the IL-18R. Methods of determining the binding epitope of an antigen binding protein are well known in the art and one such method is described in Example 4 herein.

Example 4 demonstrates that certain human IL-18R antigen binding proteins had significantly reduced ability to bind the human IL-18Rα when residues within the epitope defined by amino acids 243-271, e.g., 250-253 or 267-271, were changed to the corresponding mouse residues. Thus, provided herein are antigen binding proteins that bind human IL-18R but such binding is reduced when residues 250-253 of the human IL-18Rα chain are substituted with the corresponding mouse amino acids. Also provided herein are antigen binding proteins that bind human IL-18R but such binding is reduced when residues 267-271 of the human IL-18Rα chain are substituted with the corresponding mouse amino acids.

D. Covalent Modifications of Antigen Binding Protein

Covalent modifications of antigen binding proteins are included within the scope of this invention, and are generally, but not always, done post-translationally. For example, several types of covalent modifications of the antigen binding protein are introduced into the molecule by reacting specific amino acid residues of the antigen binding protein with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking antigen binding proteins to a water-insoluble support matrix or surface for use in a variety of methods. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, pp. 79-86 [1983]), acetylation of the N-terminal amine, and amidation of any C-terminal carboxyl group.

1. Glycosylation

Another type of covalent modification of the antigen binding protein included within the scope of this invention comprises altering the glycosylation pattern of the protein. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antigen binding protein is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antigen binding protein amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on the antigen binding protein is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, 1981, *CRC Crit. Rev. Biochem.*, pp. 259-306.

Removal of carbohydrate moieties present on the starting antigen binding protein may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, *Arch. Biochem. Biophys.* 259:52 and by Edge et al., 1981, *Anal. Biochem.* 118:131. Enzymatic cleavage of carbohydrate moieties on polypeptides can be achieved by the use of a variety of endo- and exo-glycosidases as described by Thotakura et al., 1987, *Meth. Enzymol.* 138:350. Glycosylation at potential glycosylation sites may be prevented by the use of the compound tunicamycin as described by Duskin et al., 1982, *J. Biol. Chem.* 257:3105. Tunicamycin blocks the formation of protein-N-glycoside linkages.

2. PEGylation

Another type of covalent modification of the antigen binding protein comprises linking the antigen binding protein to various nonproteinaceous polymers, including, but not limited to, various polyols such as polyethylene glycol, polypropylene glycol or polyoxyalkylenes, in the manner set forth in U.S. Pat. No. 4,640,835; 4,496,689; 4,301,144; 4,670,417; 4,791,192 or 4,179,337. In addition, as is known in the art, amino acid substitutions may be made in various positions within the antigen binding protein to facilitate the addition of polymers such as PEG.

3. Labels And Effector Groups

In some embodiments, the covalent modification of the antigen binding proteins of the invention comprises the addition of one or more labels.

The term "labeling group" means any detectable label. Examples of suitable labelling groups include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labelling group is coupled to the antigen binding protein via spacer arms of various lengths to reduce potential steric hindrance. Various methods for labelling proteins are known in the art and may be used in performing the present invention.

The term "effector group" means any group coupled to an antigen binding protein that acts as a cytotoxic agent. Examples for suitable effector groups are radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$). Other suitable groups include toxins, therapeutic groups, or chemotherapeutic groups. Examples of suitable groups include calicheamicin, auristatins, geldanamycin and maytansine. In some embodiments, the effector group is coupled to the antigen binding protein via spacer arms of various lengths to reduce potential steric hindrance.

In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labelling group is coupled to the antigen binding protein via spacer arms of various lengths to reduce potential steric hindrance. Various methods for labelling proteins are known in the art and may be used in performing the present invention.

Specific labels include optical dyes, including, but not limited to, chromophores, phosphors and fluorophores, with the latter being specific in many instances. Fluorophores can be either "small molecule" fluores, or proteinaceous fluores.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in Molecular Probes Handbook by Richard P. Haugland, hereby expressly incorporated by reference.

Suitable proteinaceous fluorescent labels also include, but are not limited to, green fluorescent protein, including a *Renilla, Ptilosarcus,* or *Aequorea* species of GFP (Chalfie et al., 1994, *Science* 263:802-805), EGFP (Clontech Laboratories, Inc., Genbank Accession Number U55762), blue fluorescent protein (BFP, Quantum Biotechnologies, Inc. 1801 de Maisonneuve Blvd. West, 8th Floor, Montreal, Quebec, Canada H3H 1J9; Stauber, 1998, *Biotechniques* 24:462-471; Heim et al., 1996, *Curr. Biol.* 6:178-182), enhanced yellow fluorescent protein (EYFP, Clontech Laboratories, Inc.), luciferase (Ichiki et al., 1993, *J. Immunol.* 150:5408-5417), β galactosidase (Nolan et al., 1988, *Proc. Natl. Acad. Sci. U.S.A.* 85:2603-2607) and *Renilla* (WO92/15673, WO95/07463, WO98/14605, WO98/26277, WO99/49019, U.S. Pat. Nos. 5,292,658, 5,418,155, 5,683,888, 5,741,668, 5,777,079, 5,804,387, 5,874,304, 5,876,995, 5,925,558). All of the above-cited references are expressly incorporated herein by reference.

E. Polynucleotides Encoding IL-18 Receptor Antigen Binding Proteins

In certain aspects, the invention provides nucleic acid molecules encoding the IgGs, variable regions and CDRs of SEQ ID NOs:1-34, 73, 75, 77, 79, 81, 83, 85, 87, 89-190. In one embodiment, the nucleic acids have the nucleotide sequence of any of SEQ ID NOs:35-68, 74, 76, 78, 80, 82, 84, 86, 88, and 191-292.

As described herein, a variable region or CDR nucleic acid encodes a variable region or CDR protein, respectively. By "nucleic acid" herein is meant any nucleic acid, including both DNA and RNA. Nucleic acids of the present invention are typically polynucleic acids; that is, polymers of individual nucleotides that are covalently joined by 3', 5' phosphodiester bonds.

Depending on its use, the nucleic acid may be double stranded, single stranded, or contain portions of both double stranded or single stranded sequence. As will be appreciated by those in the art, the depiction of a single strand ("Watson") also defines the sequence of the other strand ("Crick"); thus the nucleic acid sequences depicted in SEQ ID NOs:35-68 also include the complement of these sequences. By the term "recombinant nucleic acid" herein is meant nucleic acid, originally formed in vitro, in general, by the manipulation of nucleic acid by endonucleases, in a form not normally found in nature. Thus an isolated antigen binding protein nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention.

As will be appreciated by those in the art, due to the degeneracy of the genetic code, an extremely large number of nucleic acids may be made, all of which encode the CDRs (and heavy and light chains or other components of the antigen binding protein) of the present invention. Thus, having identified a particular amino acid sequence, such as SEQ ID NOs:1-34, those skilled in the art could make any number of different nucleic acids, by simply modifying the sequence of one or more codons in a way which does not change the amino acid sequence of the encoded protein.

F. Methods of Producing Antigen Binding Proteins

The present invention also provides expression systems and constructs in the form of plasmids, expression vectors, transcription or expression cassettes which comprise at least one polynucleotide as above. In addition, the invention provides host cells comprising such expression systems or constructs.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the IL-18 receptor antigen binding protein coding sequence; the oligonucleotide sequence encodes polyHis (such as hexaHis), or another "tag" such as FLAG, HA (hemaglutinin influenza virus), or myc, for which commercially available antibodies exist. This tag is typically fused to the polypeptide upon expression of the polypeptide, and can serve as a means for affinity purification or detection of the IL-18 receptor antigen binding protein from the host cell. Affinity purification can be accomplished, for example, by column chromatography using antibodies against the tag as an affinity matrix. Optionally, the tag can subsequently be removed from the purified IL-18 receptor antigen binding protein by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitis virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antigen binding protein antibody that binds to IL-18 receptor polypeptide. As a result, increased quantities of a polypeptide such as an IL-18 receptor antigen binding protein are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, such as where glycosylation is desired in a eukaryotic host cell expression system, one may manipulate the various pre- or prosequences to improve glycosylation or yield. For example, one may alter the peptidase cleavage site of a particular signal peptide, or add prosequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning vectors of the invention will typically contain a promoter that is recognized by the host organism and operably linked to the molecule encoding the IL-18 receptor antigen binding protein. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe gene to which they are operably linked, that is, with little or no control over gene expression. A large number of promoters, recognized by a variety of potential host cells, are well known. A suitable promoter is operably linked to the DNA encoding heavy chain or light chain comprising an IL-18 receptor antigen binding protein of the invention by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, *Nature* 290:304-310); CMV promoter (Thornsen et al., 1984, *Proc. Natl. Acad. U.S.A.* 81:659-663); the promoter contained in the 3' long terminal repeat of Rous sarcoma virus (Yamamoto et al., 1980, *Cell* 22:787-797); herpes thymidine kinase promoter (Wagner et al., 1981, *Proc. Natl. Acad. Sci. U.S.A.* 78:1444-1445); promoter and regulatory sequences from the metallothionine gene Prinster et al., 1982, *Nature* 296:39-42); and prokaryotic promoters such as the beta-lactamase promoter (Villa-Kamaroff et al., 1978, *Proc. Natl. Acad. Sci. U.S.A.* 75:3727-3731); or the tac promoter (DeBoer et al., 1983, *Proc. Natl. Acad. Sci. U.S.A.* 80:21-25). Also of interest are the following animal transcriptional control regions, which exhibit tissue specificity and have been utilized in transgenic animals: the elastase I gene control region that is active in pancreatic acinar cells (Swift et al., 1984, *Cell* 38:639-646; Ornitz et al., 1986, *Cold Spring Harbor Symp. Quant. Biol.* 50:399-409; MacDonald, 1987, *Hepatology* 7:425-515); the insulin gene control region that is active in pancreatic beta cells (Hanahan, 1985, *Nature* 315: 115-122); the immunoglobulin gene control region that is active in lymphoid cells (Grosschedl et al., 1984, *Cell* 38:647-658; Adames et al., 1985, *Nature* 318:533-538; Alexander et al., 1987, *Mol. Cell. Biol.* 7:1436-1444); the mouse mammary tumor virus control region that is active in testicular, breast, lymphoid and mast cells (Leder et al., 1986, *Cell* 45:485-495); the albumin gene control region that is active in liver (Pinkert et al., 1987, *Genes and Devel.* 1:268-276); the alpha-feto-protein gene control region that is active in liver (Krumlauf et al., 1985, *Mol. Cell. Biol.* 5:1639-1648; Hammer et al., 1987, Science 253:53-58); the alpha 1-antitrypsin gene control region that is active in liver (Kelsey et al., 1987, *Genes and Devel.* 1:161-171); the beta-globin gene control region that is active in myeloid cells (Mogram et al., 1985, *Nature* 315:338-340; Kollias et al., 1986, *Cell* 46:89-94); the myelin basic protein gene control region that is active in oligodendrocyte cells in the brain (Readhead et al., 1987, *Cell* 48:703-712); the myosin light chain-2 gene control region that is active in skeletal muscle (Sani, 1985, *Nature* 314:283-286); and the gonadotropic releasing hormone gene control region that is active in the hypothalamus (Mason et al., 1986, *Science* 234:1372-1378).

An enhancer sequence may be inserted into the vector to increase transcription of DNA encoding light chain or heavy chain comprising an IL-18 receptor antigen binding protein of the invention by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al., 1984, *Nature* 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain, a heavy chain, or a light chain and a heavy chain comprising an IL-18 receptor antigen binding sequence has been inserted into the proper site of the vector, the completed vector may be inserted into a suitable host cell for amplification and/or polypeptide expression. The transformation of an expression vector for an IL-18 receptor antigen binding protein into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., 2001, supra.

A host cell, when cultured under appropriate conditions, synthesizes an IL-18 receptor antigen binding protein that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected through determining which cell lines have high expression levels and constitutively produce antigen binding proteins with IL-18 receptor binding properties. In another embodiment, a cell line from the B cell lineage that does not make its own antibody but has a capacity to make and secrete a heterologous antibody can be selected.

G. Use of IL-18 Receptor Antigen Binding Proteins for Diagnostic and Therapeutic Purposes Antigen binding proteins of the invention are useful for detecting IL-18 receptor in biological samples and identification of cells or tissues that produce IL-18 receptor protein. Antigen binding proteins of the invention that specifically bind to IL-18 receptor may be used in treatment of IL-18 receptor mediated diseases in a patient in need thereof. For one, the IL-18 receptor antigen binding proteins of the invention can be used in diagnostic assays, e.g., binding assays to detect and/or quantify IL-18 receptor expressed in a tissue or cell. In addition, the IL-18 receptor antigen binding protein of the invention can be used to inhibit IL-18 receptor from forming a complex with its ligand, e.g., IL-18, thereby modulating the biological activity of IL-18 receptor in a cell or tissue. Antigen binding proteins that bind to IL-18 receptor thus may modulate and/or block interaction with other binding compounds and as such may have therapeutic use in ameliorating IL-18 receptor mediated diseases. In specific embodiments, IL-18 receptor antigen binding proteins may block IL-18 binding to its receptor, which may result in disruption of the IL-18 receptor induced signal transduction cascade.

1. Indications

Increased levels of IL-18 and/or involvement of IL-18 mediated signals in disease pathogenesis have been demonstrated in a variety of conditions and diseases. The antigen binding proteins of the present invention thus serve to regulate or suppress an immune response and have efficacy in the treatment and prevention of various diseases caused by an excessive immune response (see, WO2004/002519; WO2005/063290; WO2004/034988; Mallat et al., 2002, *Circ. Res.* 91:441-448). Accordingly, the IL-18 receptor antigen binding proteins of the present invention can be used for the diagnosis, prevention or treatment of diseases or conditions associated with the IL-18.

A disease or condition associated with IL-18 means any disease or condition whose onset in a patient is caused by or prevented by the interaction of IL-18 with the IL-18 receptor. The severity of the disease or condition can also be increased or decreased by the interaction of IL-18 with the IL-18 receptor. For example, IL-18 is associated with autoimmune diseases (WO2004/002519; WO2005/063290; WO2004/034988; Mallat et al., 2002, *Circ. Res.* 91:441-448), hepatic disease (Finitto et al., 2004, *Liver* 53:392-400; Tsutsui et al., 2000, *Immunological Reviews* 174:192-209; Ludwiczek et al., 2002, *J. Clinical Immunology* 22:331-337), pancreatic disease and cardiovascular diseases (Gerdes et al, 2002, *J. Exp. Med.* 195:245-257; WO03/080104; WO02/060479; WO01/85201; Raeburn et al., 2002, *Am. J. Physiol. Heart Circ. Physiol.* 283:H650-H657).

Examples of autoimmune diseases that are associated with IL-18 include psoriasis, inflammatory arthritis such as rheumatoid arthritis (WO2005/063290; Cannetti et al., 2003, *J. Immunol.* 171:1009-1015; Charles et al., 1999, *J. Immunol.* 163: 1521-1528; Cunnane et al., 2000, *Online J. Rheumatol.* 27: 58-63; Yoshimoto, 1998, *J. Immunol.* 161: 3400-3407), lupus (WO2005/063290), Type I diabetes, Type II diabetes, Crohn's disease (Niederau, 1997, *Online NLM*), inflammatory bowel disease (WO2004/002519), multiple sclerosis, autoimmune hepatitis (Tsutsui et al., 2000, supra), primary biliary cirrhosis (PBC), acquired immune deficiency syndrome (AIDS), atopic dermatitis (Konishi et al., 2002, *Proc. Natl. Acad. Sci. U.S.A.* 99:11340-11345), myasthenia gravis, and sarcoidosis.

In rheumatoid arthritis, elevated levels of mature IL-18 have been demonstrated in patient sera and synovial fluid. In some studies, IL-18 levels were shown to correlate with disease activity and response to disease modifying treatment. Extremely elevated serum levels of IL-18 have consistently been measured in systemic Juvenile Idiopathic Arthritis and the closely related Adult-Onset Still's Disease. WO2005/063290; Cannetti et al., 2003, *J. Immunol.* 171:1009-1015; Charles et al., 1999, *J. Immunol.* 163: 1521-1528; Cunnane et al., 2000, *Online J. Rheumatol.* 27: 58-63; Yoshimoto, 1998, *J. Immunol.* 161: 3400-3407.

Other forms of arthritis that are associated with IL-18 include for example ankylosing spondylitis, back pain, carpal deposition syndrome, Ehlers-Danlos-Syndrome, gout, juvenile arthritis, lupus erythematosus, myositis, osteogenesis imperfecta, osteoporosis, polyartheritis; polymyositis, psoriatic arthritis, Reiter's syndrome, scleroderma, arthritis with bowel disease, Behcets's disease, children's arthritis, degenerative joint disease, fibromyalgia, infectious arthritis, Lyme disease, Marian syndrome, osteoarthritis, osteonecrosis, Pagets Disease, Polymyalgia rheumatica, pseudogout, reflex sympathetic dystrophy, rheumatoid arthritis, rheumatism, Sjogren's syndrome, familial adenomatous polyposis and the like. Dai et al., 2004, *Arthritis Rheum.* 50:432-443; Kawashima et al., 2004, *Online Arthritis Res. Ther.* 6:R39-R45; Myers et al., 2004, *Rheumatology* 43:272-276; Wei et al., 2001, *American Association Of Immunologists*, pp. 517-521.

Elevated levels of IL-18 have also been found in patients with Crohn's disease when compared with patients with ulcerative colitis or non-inflammatory intestinal conditions. Both intestinal epithelial cells and lamina propria mononuclear cells have been identified as the source of increased IL-18 production in situ. Crohn's disease lesions have been shown to be infiltrated with IL-18R expressing cells. Niederau, 1997, *Online NLM*.

IL-18 has also been implicated as being associated with ulcerative colitis and Coeliac Disease.

Central Nervous System (CNS) lesions, cerebrospinal fluid, and sera from patients with Multiple Sclerosis have been shown to contain increased levels of IL-18 message or protein. Within lesions, microglia and macrophages are thought to be the source of IL-18. IL-18 cannot be detected in control tissue biopsies from individuals with non-inflammatory CNS diseases. Particularly high levels of IL-18 has been found in the patient subset with relapsing-remitting disease; and IL-18 levels have been found to increase during relapses compared to periods of remission. Huang et al., 2004, *Mult. Soler.* 10:482-7; Karni et al., 2002, *J. Neuroimmunol.* 125:

134-40; Losy et al., 2001, *Acta Neurol. Scand.* 104:171-3; Nicoletti et al., 2001, *Neurology* 57:342-4; Fassbender et al., 1999, *Neurology* 53:1104-6.

In patients with psoriasis, serum levels of IL-18 were reported to be increased, correlating with the extent of skin lesions and PASI score. Overexpression of both IL-18 and IL-18R mRNA has been demonstrated in lesional skin compared with non-lesional or normal skin controls. Documented overexpression of IFN-γ and TNF-α in psoriatic skin is consistent with biological activities exerted by IL-18. Arican et al., 2005, *Mediators Inflamm.* 2005:273-9; Piskin et al., 2004, *Exp. Dermatol.* 13:764-72; Companjen et al., 2004 *Eur. Cytokine Netw.* 15:210-6; Pietrzak et al., 2003, *Acta Derm. Venereol.* 83:262-5.

Various other autoimmune diseases have been associated with increased levels of IL-18 either in diseased tissue or in the serum. These include Systemic Lupus Erythematosus, atopic dermatitis, myasthenia gravis, type I diabetes, and sarcoidosis. IL-18 may also be involved in asthma, Alzheimer's Disease, allergic rhinitis, Idiopathic Thrombocytopenic Purpura (ITP), transplantation and GvHD.

IL-18 has also been implicated in a liver or hepatic diseases and in conditions associated with liver damage or injury. Liver damage or injury may have diverse causes. It may be due to viral or bacterial infections, alcohol abuse, immunological disorders, or cancer, for example. Liver injury also includes damages of the bile ducts, and damage to the liver in conditions such as alcoholic hepatitis, liver cirrhosis, viral hepatitis, primary biliary cirrhosis, and alcohol-related hepatic necro-inflammation. Finitto et al., 2004, *Liver* 53:392-400; Tsutsui et al., 2000, *Immunological Reviews* 174:192-209; Ludwiczek et al., 2002, *J. Clinical Immunology* 22:331-337.

Hepatic diseases that are associated with IL-18 include hepatitis C and hepatitis B. IL-18 has been implicated in the pathogenesis of both autoimmune and infectious hepatitis. It is thought to contribute to hepatocyte death via upregulation of proapoptotic molecules, including FasL. It has been suggested that the beneficial effect of interferon-alpha in hepatitis C may be mediated through reduced levels of IL-18. In contrast, IL-18 administration had a beneficial effect in a transgenic model of hepatitis B, improving viral clearance through increased NK and CTL activity. Finitto et al., 2004, *Liver* 53:392-400; Tsutsui et al., 2000, *Immunological Reviews* 174:192-209; Ludwiczek et al., 2002, *J. Clinical Immunology* 22:331-337.

Apart from Hepatitis B and C virus, at least four other viruses causing virus-associated hepatitis have been discovered so far, called Hepatitis A, D, E and G-Virus.

IL-18 is also associated with cardiovascular disease, including atheromatous plaque rupture, post-ischemic heart failure, reperfusion injury, atherosclerosis, chronic heart failure, cardiovascular complications of rheumatoid arthritis and other cardiovascular disorders. IL-18 is thought to markedly depress cardiac output in the setting of sepsis or endotoxin shock. IL-18 is an important link between inflammatory processes and atherogenesis, which is particularly relevant given the accumulating evidence for large excess mortality from cardiovascular causes in patients with chronic inflammatory conditions, including RA and lupus. IL-18 levels have been shown to be a strong independent predictor of death from cardiac events (with better predictive power than CRP levels). Gerdes et al, 2002, *J. Exp. Med.* 195:245-257; WO03/080104; WO02/060479; WO01/85201; Raeburn et al., 2002, *Am. J. Physiol. Heart Circ. Physiol.* 283:H650-H657.

IL-18 may also be associated with pulmonary diseases such as, for example, Chronic Obstructed Pulmonary Disease (COPD), chronic severe asthma and Acute Respiratory Distress Syndrome (ARDS).

2. Diagnostic Methods

The antigen binding proteins of the invention can be used for diagnostic purposes to detect, diagnose, or monitor diseases and/or conditions associated with IL-18 or the IL-18 receptor. The invention provides for the detection of the presence of the IL-18 receptor in a sample using classical immunohistological methods known to those of skill in the art (e.g., Tijssen, 1993, *Practice and Theory of Enzyme Immunoassays*, vol 15 (Eds R. H. Burdon and P. H. van Knippenberg, Elsevier, Amsterdam); Zola, 1987, *Monoclonal Antibodies: A Manual of Techniques*, pp. 147-158 (CRC Press, Inc.); Jalkanen et al., 1985, *J. Cell. Biol.* 101:976-985; Jalkanen et al., 1987, *J. Cell Biol.* 105:3087-3096). The detection of the IL-18 receptor can be performed in vivo or in vitro.

Diagnostic applications provided herein include use of the antigen binding proteins to detect expression of the IL-18 receptor and binding of the ligands to the IL-18 receptor. Examples of methods useful in the detection of the presence of the IL-18 receptor include immunoassays, such as the enzyme linked immunosorbent assay (ELISA) and the radioimmunoassay (RIA).

For diagnostic applications, the antigen binding protein typically will be labeled with a detectable labeling group. Suitable labeling groups include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labelling group is coupled to the antigen binding protein via spacer arms of various lengths to reduce potential steric hindrance. Various methods for labelling proteins are known in the art and may be used in performing the present invention.

One aspect of the invention provides for identifying a cell or cells that express the IL-18 receptor. In a specific embodiment, the antigen binding protein is labeled with a labeling group and the binding of the labeled antigen binding protein to the IL-18 receptor is detected. In a further specific embodiment, the binding of the antigen binding protein to the IL-18 receptor detected in vivo. In a further specific embodiment, the antigen binding protein-IL-18 receptor is isolated and measured using techniques known in the art. See, for example, Harlow and Lane, 1988, *Antibodies: A Laboratory Manual*, New York: Cold Spring Harbor (ed. 1991 and periodic supplements); John E. Coligan, ed., 1993, *Current Protocols In Immunology* New York: John Wiley & Sons.

Another aspect of the invention provides for detecting the presence of a test molecule that competes for binding to the IL-18 receptor with the antigen binding proteins of the invention. An example of one such assay would involve detecting the amount of free antigen binding protein in a solution containing an amount of IL-18 receptor in the presence or absence of the test molecule. An increase in the amount of free antigen binding protein (i.e., the antigen binding protein not bound to the IL-18 receptor) would indicate that the test molecule is capable of competing for IL-18 receptor binding with the antigen binding protein. In one embodiment, the antigen binding protein is labeled with a labeling group.

Alternatively, the test molecule is labeled and the amount of free test molecule is monitored in the presence and absence of an antigen binding protein.

3. Methods of Treatment: Pharmaceutical Formulations, Routes of Administration In some embodiments, the invention provides pharmaceutical compositions comprising a therapeutically effective amount of one or a plurality of the antigen binding proteins of the invention together with a pharmaceutically acceptable diluent, carrier, solubilizer, emulsifier, preservative, and/or adjuvant. In addition, the invention provides methods of treating a patient by administering such pharmaceutical composition. The term "patient" includes human and animal subjects.

Preferably, acceptable formulation materials are nontoxic to recipients at the dosages and concentrations employed. In specific embodiments, pharmaceutical compositions comprising a therapeutically effective amount of IL-18 receptor antigen binding proteins are provided.

In certain embodiments, acceptable formulation materials preferably are nontoxic to recipients at the dosages and concentrations employed. In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18" Edition, (A. R. Genrmo, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antigen binding proteins of the invention. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In specific embodiments, pharmaceutical compositions comprise Tris buffer of about pH 7.0-8.5, or acetate buffer of about pH 4.0-5.5, and may further include sorbitol or a suitable substitute therefor. In certain embodiments of the invention, IL-18 receptor antigen binding protein compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the IL-18 receptor antigen binding protein product may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such as orally. Preparation of such pharmaceutically acceptable compositions is within the skill of the art.

The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired IL-18 receptor antigen binding protein in a pharmaceutically acceptable vehicle. A particularly suitable vehicle for parenteral injection is sterile distilled water in which the IL-18 receptor antigen binding protein is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antigen binding protein.

Pharmaceutical compositions of the invention can be formulated for inhalation. In these embodiments, IL-18 receptor antigen binding proteins are advantageously formulated as a dry, inhalable powder. In specific embodiments, IL-18 receptor antigen binding protein inhalation solutions may also be formulated with a propellant for aerosol delivery. In certain embodiments, solutions may be nebulized. Pulmonary administration and formulation methods therefore are further described in International Patent Application No. PCT/US94/001875, which is incorporated by reference and describes pulmonary delivery of chemically modified proteins. It is also contemplated that formulations can be administered orally. IL-18 receptor antigen binding proteins that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. Additional agents can be included to facilitate absorption of the IL-18 receptor antigen binding protein. Diluents, flavorings, low melting point waxes, vegetable oils, lubricants, suspending agents, tablet disintegrating agents, and binders may also be employed.

A pharmaceutical composition of the invention is preferably provided to comprise an effective quantity of one or a plurality of IL-18 receptor antigen binding proteins in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving IL-18 receptor antigen binding proteins in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, *Biopolymers* 2:547-556), poly (2-hydroxyethyl-inethacrylate) (Langer et al., 1981, *J. Biomed. Mater. Res.* 15:167-277 and Langer, 1982, *Chem. Tech.* 12:98-105), ethylene vinyl acetate (Langer et al., 1981, supra) or poly-D(−)-3-hydroxybutyric acid (European Patent Application Publication No. EP 133,988). Sustained release compositions may also include liposomes that can be prepared by any of several methods known in the art. See, e.g., Eppstein et al., 1985, *Proc. Natl. Acad. Sci. U.S.A.* 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration. The invention also provides kits for producing a single-dose administration unit. The kits of the invention may each contain both a first container having a dried protein and a second container having an aqueous formulation. In certain embodiments of this invention, kits containing single and multi-chambered pre-filled syringes (e.g., liquid syringes and lyosyringes) are provided.

The therapeutically effective amount of an IL-18 receptor antigen binding protein-containing pharmaceutical composition to be employed will depend, for example, upon the therapeutic context and objectives. One skilled in the art will appreciate that the appropriate dosage levels for treatment will vary depending, in part, upon the molecule delivered, the indication for which the IL-18 receptor antigen binding protein is being used, the route of administration, and the size (body weight, body surface or organ size) and/or condition (the age and general health) of the patient. In certain embodiments, the clinician may titer the dosage and modify the route of administration to obtain the optimal therapeutic effect. A typical dosage may range from about 0.1 μg/kg to up to about 30 mg/kg or more, depending on the factors mentioned above. In specific embodiments, the dosage may range from 0.1 μg/kg up to about 30 mg/kg, optionally from 1 μg/kg up to about 30 mg/kg or from 10 μg/kg up to about 5 mg/kg.

Dosing frequency will depend upon the pharmacokinetic parameters of the particular IL-18 receptor antigen binding protein in the formulation used. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data. In certain embodiments, the antigen binding proteins of the invention can be administered to patients throughout an extended time period. Chronic administration of an antigen binding protein of the invention minimizes the adverse immune or allergic response commonly associated with antigen binding proteins that are not fully human, for example an antibody raised against a human antigen in a non-human animal, for example, a non-fully human antibody or non-human antibody produced in a non-human species.

The route of administration of the pharmaceutical composition is in accord with known methods, e.g., orally, through injection by intravenous, intraperitoneal, intracerebral (intra-parenchymal), intracerebroventricular, intramuscular, intraocular, intraarterial, intraportal, or intralesional routes; by sustained release systems or by implantation devices. In certain embodiments, the compositions may be administered by bolus injection or continuously by infusion, or by implantation device.

The composition also may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

It also may be desirable to use IL-18 receptor antigen binding protein pharmaceutical compositions according to the invention ex vivo. In such instances, cells, tissues or organs that have been removed from the patient are exposed to IL-18 receptor antigen binding protein pharmaceutical compositions after which the cells, tissues and/or organs are subsequently implanted back into the patient.

In particular, IL-18 receptor antigen binding proteins can be delivered by implanting certain cells that have been genetically engineered, using methods such as those described herein, to express and secrete the polypeptide. In certain embodiments, such cells may be animal or human cells, and may be autologous, heterologous, or xenogeneic. In certain embodiments, the cells may be immortalized. In other embodiments, in order to decrease the chance of an immunological response, the cells may be encapsulated to avoid infiltration of surrounding tissues. In further embodiments, the encapsulation materials are typically biocompatible, semipermeable polymeric enclosures or membranes that allow the release of the protein product(s) but prevent the destruction of the cells by the patient's immune system or by other detrimental factors from the surrounding tissues.

All references cited within the body of the instant specification are hereby expressly incorporated by reference in their entirety.

The following examples, including the experiments conducted and the results achieved, are provided for illustrative purposes only and are not to be construed as limiting the invention.

EXAMPLES

A. Example 1

Production of IgG2 and IgG4 Versions of Anti-IL-18 Receptor Antibodies Using pVE414N Transient Expression Constructs The following example describes the generation of transient expression constructs used to produce IgG2 and IgG4 versions of various anti-IL18 receptor binding proteins, and experimental approaches to test their binding characteristics and potency.

1. Generation of Constructs

Expression constructs for transient expression of IgG4 versions of $AM_H9/AM_L9$, $AM_H11/AM_L7$, $AM_H3/AM_L14$, and $AM_H6/AM_L12$ were generated by subcloning the polynucleotide sequences of SEQ ID NOs:74, 76, 78, 80, 82, 84, 86 and 88 into a transient expression vector. IgG2 versions of the same variable regions were generated by subcloning the polynucleotide portions encoding the variable regions of those IgGs into a separate transient expression vector.

2. Transient Roller Bottle Tranfections

Eight roller bottle transfections into CosPKB cell line for each of the antibodies were performed. The titers for the IgG2's were as follows:

| IgG2 | Titer |
|---|---|
| AMH9/AML9 | 33.5 |
| AMH11/AML7 | 35.1 |
| AMH3/AML14 | 42.9 |
| AMH6/AML12 | 41.5 |

3. Assays for Potency and Cross Reactivity of Various Antibodies

KG-1 IFNγ Release Assay. The various IgG constructs were tested to determine their inhibitory activity in an in vitro Interferon-γ (IFNγ) release assay. The IFNγ release assay works on the principle that human myelomonocytic KG-1 cells that express the endogenous IL-18R release IFNγ in response to IL-18.

Briefly, reagents such as affinity-purified scFv are pre-incubated with KG-1 cells in a 96-well tissue culture plate. IL-18 (+TNFα) is added to the cells to induce IFNγ release. TNFα is added with the IL-18 to increase the IFNγ response and therefore makes the assay more sensitive by allowing a lower concentration of IL-18 to be used. This is at least in part, likely due to TNFα induced upregulation of IL-18R surface expression.

After a defined incubation period, the cell supernatants are harvested and analyzed for IFNγ content using ELISA. Test compounds that inhibit IL-18R mediated signaling can be assessed in this assay by showing a reduction in IFNγ release.

KG-1 cells were obtained from the European Collection of Cell Cultures (ECACC, 86111306). The cells were propagated in supplemented Iscove's Dulbecco modified medium (IMDM), and were maintained at $1-2 \times 10^6$ cells/ml. Recombinant human IL-18 was obtained from Peprotech (200-18) and the recombinant human TNFα was purchased from R&D Systems (210-TA). The amount of IFNγ released in response to 1 nM IL-18 (+1.1 nM TNFα) was monitored in each experiment, and ranged from approximately 250 to 4000 pg/ml.

The KG-1 assay was carried out in 96 flat bottom well cell culture plates (Costar). Test solutions of antibody (in duplicate) were used neat (or diluted to the required concentration in Dulbecco's PBS) in a volume of 50 µl. The antibodies were then titrated in a 6-9 point ⅓ dilution series (using KG-1 medium), followed by the addition of 50 µl KG-1 cells with gentle mixing. A "no antibody" control with only IL-18 and a "cells only" control were always included. After incubation of the antibody/cell mixture for 30-60 minutes at 37° C. with 5% $CO_2$, 100 µl of IL-18+TNFα diluted in KG-1 medium was added with gentle mixing. The final concentration of IMAC-purified scFv typically ranged between 25-200 µg/ml. Three reference inhibitors were used in all assays. The first two were monoclonal antibodies against the two different chains of the IL-18, RP1 (R&D systems, MAB840) and AcPL (R&D Systems, MAB1181). These antibodies were used as described above for scFv, except that the final starting concentration for the dilution series was 10-20 µg/ml. In addition, a recombinant IL-18BP/Fc chimera (R&D Systems, 119-BP) was used to neutralize IL-18. In this case, 50 µl of KG-1 medium was added to the cell culture plate, followed by 50 µl of cells and the cells were incubated as above for the antibodies. In a separate 96 well "U" bottom cell culture plate, the IL-18BP/Fc was titrated in a 6-9 point ½ dilution series (using KG-1 medium) in a volume of 60 µl/well. An equal volume of IL-18+TNFα was added to the IL-18BP/Fc dilution series. After incubation of the IL-18BP/Fc/IL-18 mixture for 30-60 minutes at 37° C. with 5% $CO_2$, 100 µl/well was added to the KG-1 cell plate with gentle mixing. The final starting concentration of the IL-18BP/Fc for the dilution series was 1 mg/ml. The final concentration of the KG-1 cells was $1.5 \times 10^6$ cells/ml (i.e. $3 \times 10^6$/well) and IL-18 was used at a final concentration of 1 nM (+1.1 nM TNFα).

IL-18 was also titrated to determine the EC50 of the IFNγ response. The IL-18 was titrated in a 6-10 point ½ dilution series (using KG-1 medium), with the TNFα held constant at 1.1 nM. In this case 50 ml of KG-1 medium was added to the cell culture plate, followed by 50 ml of cells. The cell plate was incubated for 30-60 minutes at 37° C. with 5% $CO_2$, then 100 ml of the titrated IL-18 was added with gentle mixing. The final concentration of IL-18 started at 5 nM for the dilution series. Typically, the $EC_{50}$ for IL-18 (+TNFα) was in the range of 0.5-1 nM, although minimum and maximum $EC_{50}$ values of down to 0.3 nM or up to 5 nM were occasionally seen.

The KG-1 cell plates were incubated at 37° C. with 5% $CO_2$ overnight. The cell supernatants were harvested by removal of 180 ml medium into a clean "U" bottom 96-well plate, which was then sealed and centrifuged at 1200 rpm for 5 minutes. 160 ml of the cell free supernatant was then transferred to another clean "U" bottom 96-well plate, and the clarified supernatants tested immediately or frozen at −20° C.

The amount of IFNγ in the KG-1 cell supernatants was determined by a standard sandwich ELISA based assay, using a time-resolved fluorometric readout. FLUORONUNC flat bottom 96-well plates (NUNC, 437958) were coated using 100 ml/well of the IFNγ specific monoclonal capture antibody (R&D Systems, MAB2851) at 4 mg/ml and left at +4° C. overnight. The plates were rinsed with Dulbecco's PBS, then non-specific protein binding was blocked by the addition of 200 ml/well of 3% milk powder in PBS and incubation at RT (RT) for 1-2 hours. The recombinant human IFNγ standard (R&D Systems, 285-IF-100) was diluted to 16,000 pg/ml in reagent diluent (0.1% BSA, 0.05% Tween-20, 20 mM Tris, 150 mM NaCl; pH 7.2-7.4), then titrated in a 12 point ½ dilution series. The blocking buffer was removed from the capture antibody coated plates, and 100 ml/well of the IFNγ standard or clarified cell supernatants was added. Reagent diluent was added for the "blank" control. After incubation for 1-2 hours at RT, the plates were washed 3× with PBS containing 0.1% Tween-20. The biotinylated anti-human IFNγ polyclonal detection antibody (R&D Systems, BAF285) was diluted to 100 ng/ml in reagent diluent supplemented with 2% normal goat serum, and 100 ml/well was added. After incubation for 1 hour at RT, the plates were washed 3× with PBS containing 0.1% Tween-20. Streptavidin-Europium (Perkin-Elmer, 4001-0010) was diluted 1/1000 in DELFIA assay buffer (Perkin-Elmer, 4002-0010), and 100 ml/well was added. After 30-60 minutes incubation at RT, the plates were washed 7× with DELFIA wash buffer (Perkin-Elmer, 1244-114). DELFIA Enhancement solution (Perkin-Elmer, 4001-0010) was added at 100 ml/well and the plates were left for at least 10 min at RT. The resulting fluorescent signal was measured using dissociation-enhanced time-resolved fluorometry using the Victor2 V plate reader (PerkinElmer).

The average value for the ELISA "blank" control was subtracted from the results for the IFNγ standard, while the average value for the "cells alone" control was subtracted for the cell supernatant results. GraphPad PRISM (GraphPad Software, Inc.) was used to calculate the IFNγ standard curve using non-linear regression (with a variable slope). The concentration of IFNγ in the cell supernatants was then determined by using an "unknown X from Y" output for the IFNγ standard curve. The EC50 for IFNγ release from KG-1 cells in response to IL-18 was calculated using non-linear regression (with a variable slope) and constraining the top and bottom as necessary. Inhibition of IFNγ release from KG-1 cells by test compound was normalised as a percentage of the average value of the "no antibody" IL-18 alone control, using the fluorescent counts data. The $IC_{50}$ values for test compounds could then be calculated using non-linear regression (with a variable slope), and constraining the bottom and top to 0 and 100% respectively.

The IgG2 versions of antibodies $AM_H9/AM_L9$, $AM_H11/AM_L7$, $AM_H3/AM_L14$, and $AM_H6/AM_L12$ have at least equivalent potency as the original IgG4 versions in an assay measuring their effect on the IFN-γ production by KG1 cells. Furthermore, the IgG2 versions have at least equivalent potency as the original IgG4s in an assay measuring INF-γ production by human NK cells.

The IgG2 versions of the antibodies have equivalent potency as the original IgG4s in an assay measuring their effect on IL-18 induced INF-γ production by cynomolgus PBMC#010182 cells. This confirms that the conversion to IgG2 did not affect the cyno cross reactivity of the tested antibodies.

4. Assays for Specificity

IgGs of various antibodies were analyzed for cross-reactivity by ELISA against a panel of proteins.

Test antigens were coated onto Protein Immobiliser 96-well plates (Exiqon, Prd#10203-111-60) at 1 µg/ml in PBS (Dulbecco's w/o Ca and Mg, Invitrogen, Cat#14190-086) in duplicate, 50 µl per well, overnight at 4° C.

Plates were washed three times with 300 µl PBS-Tween (0.1%) (PBS-T) and three times with 300 µl PBS per well using a 96-well plate washer (BIO-TEK, ELX405UV). To the washed plates, 300 µl of 3% Marvel PBS (MPBS) was added per well as a blocking agent. Plates were blocked at room temperature (RT) for 1 hour.

Plates were washed three times with PBS-T and three times with PBS as previously stated.

Antibodies ($huIgG_4$) were diluted to 0.5 µg/ml in 3% MPBS. 50 µl of diluted $huIgG_4$ were added per well. Plates were incubated at RT for 1 hour. Plates were washed as previously stated.

Primary detection antibody (Monoclonal anti-human IgG4 clone HP-6025 biotin conjugate, Sigma, Cat#B-3648) was diluted 1:15,000 in 3% MPBS and added to plates at 50 µl per well. Incubation with primary detection antibody was at RT for 1 hour. Plates were washed previously stated.

Secondary detection antibody (ExtrAvidin peroxidase conjugate, Sigma, Cat#E-2886), was diluted 1:1,000 in 3% MPBS and added to plates at 50 µl per well. Incubation with secondary detection antibody was at RT for 30 minutes. Plates were washed previously stated.

50 µl per well Tetramethyl-benzidine (TMB) (Liquid substrate for ELISA, Sigma, Cat#T-0440) was added and incubated at RT for 10 minutes. To stop the enzyme color reaction, 50 µl 0.5 M $H_2SO_4$ per well was added.

Plates were read at 450 nm on a 96-well plate reader (Victor² V plate reader (PerkinElmer).

The specific anti-IL-18 receptor IgG4 antibodies were positive against human and cynomolgus IL-18 receptor protein only. There was no cross-reactivity with other species. An IgG2 version of an above antibody had the same cross-reactivity properties, i.e., it cross-reacted with cynomolgus IL-18 receptor only.

B. Example 2

Characterization of the Binding Affinity of an IL-18 Receptor Antibody

This Example provides an exemplary method of determining the binding affinity of an IL-18 receptor antigen binding protein to cell surface-expressed human IL-18Rα. An IL-18 receptor antibody was iodinated using [$^{125}$I]-Bolton-Hunter Reagent (diiodinated; PerkinElmer Life Sciences, Inc., Boston, Mass.). One millicurie of [$^{125}$I]-Bolton-Hunter Reagent supplied in anhydrous benzene was evaporated to dryness under a nitrogen stream. Five microliters of IL-18 receptor antibody (16 micrograms) was diluted with an equal volume of borate buffered saline and then added to the dried [$^{125}$I]-Bolton-Hunter Reagent in its original vial. After an overnight incubation at 4° C., 10 microliters of PBS, 0.1% gelatin was added and the entire sample transferred to an equilibrated 2 mL P6 column (BioRad; Hercules, Calif.) where iodinated IL-18 receptor antibody was separated from free $^{125}$I by gel filtration with 0.1% gelatin as a carrier protein. Fractions containing iodinated antibody were pooled, diluted to a concentration of 100 nM in binding media (RPMI 1640 containing 2.5% bovine albumin, Fraction V, 20 mM Hepes, and 0.2% sodium azide, pH 7.2), and stored at 4° C. A specific activity of $3.5 \times 10^{15}$ cpm/mmol was calculated based on an initial protein concentration of antibody by amino acid analysis, and a recovery of 70% from a control experiment in which an aliquot of iodiniated antibody was put through the iodination protocol with omission of $[^{125}I]$-Bolton-Hunter Reagent.

1. Direct Equilibrium Binding

KG-1 cells were stimulated for 20 hours at 37° C. in 5% $CO_2$ in IMDM medium containing 20% fetal calf serum in the presence of 20 ng/mL of human TNFα. The stimulated KG-1 cells ($5 \times 10^5$ cells/150 microliters final) were washed twice with PBS, and then incubated with a range of concentrations of iodinated antibody. Nonspecific binding was measured at a single concentration of iodinated antibody (~350 pM, in triplicate) in the presence of a 1000-fold molar excess of unlabeled antibody, and assumed to be a linear function of the concentration of iodinated antibody present. All reagents were diluted in binding media containing sodium azide (0.2%) to inhibit potential internalization of iodinated antibody by the cells.

Cells were incubated in 96-well round-bottom microtiter plates at 37° C., 5% $CO_2$ on a miniorbital shaker. After 4 hours, two 60 microliter aliquots of each mixture were transferred to chilled 400 microliter polyethylene centrifuge tubes containing 200 microliters phthalate oil (1.5 parts dibutylphthalate: 1 part dioctylphthalate) and spun for 1.5 minutes in a 4° C. tabletop microfuge (Sorvall, Asheville, N.C.) at 10,000 rpm to separate cell associated iodinated antibody from free iodinated antibody. The oil tubes were cut, and each cell pellet and supernatant was collected in individual 12×75 mm glass tubes and loaded on a COBRA gamma counter (Packard Instrument Company; Boston, Mass.) for cpm measurements. Cpm from duplicate aliquots for each well were averaged for analysis. Data were fir to a simple 1-site binding equation via nonlinear regression in Prism version 3.03 (GraphPad Software, Inc; San Diego, Calif.).

The iodinated antibody bound to stimulated KG-1 cells at 37° C. with a $K_D$ of 81 pM and ~4700 sites/cell.

2. Competition Assay

Stimulated and washed KG-1 cells ($5 \times 10^5$ cells/150 microliters final) were incubated with a single concentration of iodinated antibody (15.6 pM) and varying concentrations of unlabeled antibody in binding media. Nonspecific binding was determined in the presence of a 1000-fold molar excess of unlabeled antibody. Iodinated and unlabeled antibody were mixed just prior to the addition of cells, i.e., there was no pre-incubation step.

Cells were incubated in 96-well round-bottom microtiter plates at 37° C., 5% $CO_2$ on a miniorbital shaker. After 4 hours, two 60 microliter aliquots of each mixture were transferred to chilled 400 microliter polyethylene centrifuge tubes containing 200 microliters phthalate oil (1.5 parts dibutylphthalate: 1 part dioctylphthalate) and spun for 1.5 minutes in a 4° C. tabletop microfuge (Sorvall, Asheville, N.C.) at 10,000 rpm to separate cell associated iodinated antibody from free iodinated antibody. The oil tubes were cut, and each cell pellet and supernatant was collected in individual 12×75 mm glass tubes and loaded on a COBRA gamma counter (Packard Instrument Company; Boston, Mass.) for cpm measurements. Cpm from duplicate aliquots for each well were averaged for analysis. Data were fit to a single competitive inhibition equation via nonlinear regression using the Kd value of 81 pM in Prism.

The $K_I$ of unlabeled antibody binding was 53 pM.

C. Example 3

Characterization of the Activity of Anti-IL-18 Receptor Antibodies

A IFNγ release assay was performed as described in Example 1, Section 3 for various IgG constructs, as described below.

1. Comparison of the Inhibition of INFγ Release by KG1 Cells with $AM_H2/AM_L16$, $AM_H2/AM_L17$, $AM_H1/AM_L16$, and $AM_H1/AM_L17$ Constructs Inhibition of INF-γ release by KG1 cells when treated with $AM_H/AM_L$ antigen binding protein constructs $AM_H2/AM_L16$, $AM_H2/AM_L17$, $AM_H1/AM_L16$, and $AM_H1/AM_L17$ was compared with control treatment with IL-18 binding protein (BP). The $AM_H/AM_L$ antigen binding proteins were significantly more efficacious at inhibiting IFNγ release, all demonstrating an $ED_{50}$ between 6 and 10 pM compared to an $ED_{50}$ for IL-18 BP of 520 pM.

2. Comparison of the Inhibition of INFγ Release by KG1 Cells with $AM_H4/AM_L14$, $AM_H4/AM_L15$, $AM_H3/AM_L14$, and $AM_H3/AM_L15$ Constructs Inhibition of INF-γ release by KG1 cells when treated with $AM_H/AM_L$ antigen binding protein constructs $AM_H4/AM_L14$, $AM_H4/AM_L15$, $AM_H3/AM_L14$, and $AM_H3/AM_L15$ was compared with control treatment with IL-18 binding protein (BP). The $AM_H/AM_L$ antigen binding proteins were significantly more efficacious at inhibiting IFNγ release, all demonstrating an $ED_{50}$ between 3 and 7 pM compared to an $ED_{50}$ for IL-18 BP of 520 pM.

3. Comparison of the Inhibition Of INFγ Release by KG1 Cells with $AM_H6/AM_L12$, $AM_H6/AM_L13$, $AM_H5/AM_L12$, and $AM_H5/AM_L13$ Constructs Inhibition of INF-γ release by KG1 cells when treated with $AM_H/AM_L$ antigen binding protein constructs $AM_H6/AM_L12$, $AM_H6/AM_L13$, $AM_H5/AM_L12$, and $AM_H5/AM_L13$ was compared with control treatment with IL-18 binding protein (BP). The $AM_H/AM_L$ antigen binding proteins were significantly more efficacious at inhibiting IFNγ release, all demonstrating an $ED_{50}$ between 2.9 and 11.3 pM compared to an $ED_{50}$ for IL-18 BP of 520 pM.

4. Inhibition of INFγ Release by KG1 Cells by $AM_H8/AM_L11$, $AM_H9/AM_L9$, $AM_H10/AM_L8$, and $AM_H11/AM_L7$ IgGs Inhibition of INF-γ release by KG1 cells with $AM_H/AM_L$ IgG antigen binding protein constructs comprising combinations of $AM_H8/AM_L11$, $AM_H9/AM_L19$, $AM_H10/AM_L8$, and $AM_H11/AM_L7$ IgGs was compared with control treatment with IL-18 binding protein (BP). The $AM_H/AM_L$ antigen binding proteins were significantly more efficacious at inhibiting IFNγ release, all demonstrating an $ED_{50}$ between 3 and 45 pM compared to an $ED_{50}$ for IL-18 BP of 520 pM.

5. Inhibition of INFγ Release by KG1 Cells by $AM_H15/AM_L3$, $AM_H13/AM_L4$, $AM_H13/AM_L5$, and $AM_H16/AM_L2$ IgGs Inhibition of INF-γ release by KG1 cells with $AM_H/AM_L$ IgG antigen binding protein constructs comprising combinations of $AM_H15/AM_L3$, $AM_H13/AM_L4$, $AM_H13/AM_L5$, and $AM_H16/AM_L2$ IgGs was compared with control treatment with IL-18 binding protein (BP). The $AM_H/AM_L$ antigen binding proteins were significantly more efficacious at inhibiting IFNγ release, all demonstrating an $ED_{50}$ between 17 and 320 pM compared to an $ED_{50}$ for IL-18 BP of 520 pM.

D. Example 4

Identification of the Binding Epitope of the Described IL-18 Receptor Antibodies Experiments were carried out to determine the amino acids residues present in human IL-18 receptor (IL-18R) that are important for binding to one or more of the IL-18 receptor binding proteins. An exemplary antibody bound with high affinity to human IL-18R but did not bind the mouse ortholog of IL-18R. Experiments were directed towards examining the amino acids that differ between human and mouse IL-18R. This was coupled with analysis of a three dimensional computational model of the IL-18R to determine which of those amino acids lie on the surface of the receptor and are therefore more likely to interact with the antibody. Candidate amino acids were examined for their contribution to antibody recognition by using site-specific mutagenesis to change the particular amino acids from the human sequence to mouse sequence and then testing the mutant IL-18R molecules for binding to antibody. The relative ability of antibody to bind the different mutations was assessed using antibody dose-response curves and subsequent determination of $EC_{50}$ concentrations (the concentration of antibody required for 50% of the maximal binding signal).

A region on the surface of human IL-18R was identified that is particularly important for antibody binding and thus contributes to the epitope. This region contains amino acids 243-271 (shown in bold in FIG. 5). When specific amino acids in this region were mutated to mouse sequence, antibody binding was diminished (effects on antibody binding reported in TABLE 3). Amino acids 250-253 (MFGE mutant) and 267-271 (MRIMT mutation) had the most profound influence on antibody binding however neither completely influenced antibody binding alone (see, underlined amino acid residues). When the receptor was mutated at all four of the specific sites tested, antibody binding was virtually abolished. Binding of a control anti-IL-18R receptor antibody was not significantly affected by the mutations indicating that the overall structure of the receptor had not been disrupted by the mutations. Amino acids 243-271 encode one of the predicted IL-18 contact points and thus this epitope is consistent with the antibody's ability to block IL-18 binding to the receptor.

TABLE 3

Results of Antibody Binding Assay with IL-18R and Mutated IL-18R
(the mouse amino acids corresponding to each mutation is provided in parenthesis)

| | Exemplary Ab binding: avg. EC50 (pM) | Fold decrease in binding ability relative to huIL18R | Control Ab binding: avg. EC50 (pM) |
|---|---|---|---|
| huIL18R | 15.7 +/− 9.0 | 0 | 7.9 +/− 4.7 |
| EEDV mutation (KDDL) | 25.3 +/− 11.9 | 1.6 | 6.7 +/− 4.4 |
| MFGE mutation (SIRK) | 57.9 +/− 26.7 | 3.7 | 5.9 +/− 3.7 |
| MRIMT mutation (TTTWI) | 177.5 +/− 58.9 | 11.3 | 8.5 +/− 5.1 |
| STGGT (NEEAI) | 15.7 +/− 8.5 | 0 | 10.0 +/− 6.2 |
| EEDV + MRIMT + STGGT | 2615.1 | 2287.3 | 7.9 +/− 5.1 |
| EEDV + MRIMT + MFGE + STGGT | too low to measure | N/A | 10.3 +/− 5.5 |
| Mouse IL18R | does not bind | N/A | N/A |

Human IL18R was mutated to mouse IL18R sequence at the indicated residues and recombinant mutated receptors with and avidin tag were immobilized on biotin-coated beads. Immobilized receptor was then used to determine relative antibody binding ability in a soluble binding assay. Binding was also performed using an anti-huIL-18R antibody that recognizes a distinct epitope from the exemplary antibody. Binding experiments were all performed at least two times. The average EC50 represents the concentration of antibody required to achieve 50% of maximal binding.

What is claimed is:

1. An isolated antigen binding protein that binds a human IL-18 receptor, wherein said antigen binding protein comprises:
an antibody heavy chain comprising (a) a CDRH1 of SEQ ID NO:104; (b) a CDRH2 of SEQ ID NO:105; and (c) a CDRH3 of SEQ ID NO:106; and
an antibody light chain comprising (a) a CDRL1 of SEQ ID NO:173; (b) a CDRL2 of SEQ ID NO:174; and (c) a CDRL3 of SEQ ID NO:175.

2. The antigen binding protein of claim 1, wherein said antigen binding protein comprises an antibody heavy chain of SEQ ID NO:6 or an antibody light chain of SEQ ID NO:29.

3. The antigen binding protein of claim 1, wherein said antigen binding protein comprises an antibody heavy chain of SEQ ID NO:6 and an antibody light chain of SEQ ID NO:29.

4. The antigen binding protein of claim 1, wherein said antigen binding protein is a monoclonal antibody, a recombinant antibody, a bispecific antibody, or a fragment thereof.

5. The antigen binding protein of claim 4, wherein said antibody fragment is a minibody, a domain antibody, a F(ab) fragment, a F(ab') fragment, a F(ab')$_2$ fragment, a Fv fragment, a scFv fragment, a Fd fragment, a diabody, or a single chain antibody molecule.

6. The antigen binding protein of claim 1, wherein said antigen binding protein is of an IgG1-, IgG2-IgG3- or IgG4- type.

7. The antigen binding protein of claim 6, wherein said antigen binding protein is of an IgG2-type.

8. A pharmaceutical composition comprising the antigen binding protein of claim 1, and pharmaceutically acceptable carrier.

9. An isolated antigen binding protein comprising an IgG heavy chain of SEQ ID NO:73, or an IgG light chain of SEQ ID NO:75.

10. An isolated antigen binding protein comprising an IgG heavy chain of SEQ ID NO:73 and an IgG light chain of SEQ ID NO:75.

11. A pharmaceutical composition comprising the antigen binding protein of claim 10, and pharmaceutically acceptable carrier.

12. An isolated nucleic acid molecule encoding:
a) an antibody heavy chain comprising (a) a CDRH1 of SEQ ID NO:104; b) a CDRH2 of SEQ ID NO:105; and (c) a CDRH3 of SEQ ID NO:106;
b) an antibody light chain comprising (a) a CDRL1 of SEQ ID NO:173; (b) a CDRL2 of SEQ ID NO:174; and (c) a CDRL3 of SEQ ID NO:175; or
c) the antibody heavy chain of a) and antibody light chain of b).

13. The isolated nucleic acid molecule of claim 12, wherein said nucleic acid molecule is operably linked to a control sequence.

14. A vector comprising a nucleic acid molecule of claim 13.

15. An isolated host cell transformed with the vector of claim 14.

16. A vector comprising a nucleic acid molecule of claim 12.

17. An isolated host cell transformed with the vector of claim 16.

18. An isolated host cell comprising:
a) a nucleic acid encoding an antibody heavy chain comprising (a) a CDRH1 of SEQ ID NO:104; (b) a CDRH2 of SEQ ID NO:105; and (c) a CDRH3 of SEQ ID NO:106; and
b) a nucleic acid encoding an antibody light chain comprising (a) a CDRL1 of SEQ ID NO:173; (b) a CDRL2 of SEQ ID NO:174; and (c) a CDRL3 of SEQ ID NO:175.

19. The isolated host cell of claim 18, wherein said host cell comprises a nucleic acid encoding an IgG heavy chain of SEQ ID NO:73 and a nucleic acid encoding an IgG light chain of SEQ ID NO:75.

20. A process for preparing an isolated antigen binding protein comprising an antibody heavy chain comprising (a) a CDRH1 of SEQ ID NO:104; (b) a CDRH2 of SEQ ID NO:105; and (c) a CDRH3 of SEQ ID NO:106; and
an antibody light chain (a) a CDRL1 of SEQ ID NO:173; (b) a CDRL2 of SEQ ID NO:174; and (c) a CDRL3 of SEQ ID NO:175, said process comprising the step of culturing a host cell that secretes said binding protein, and isolating said binding protein.

21. The process of claim 20, wherein the host cell comprises a nucleic acid encoding an IgG heavy chain of SEQ ID NO:73 and a nucleic acid encoding an IgG light chain of SEQ ID NO:75.

* * * * *

UNITED STATES PATENT AND TRADEMARK OFFICE
CERTIFICATE OF CORRECTION

| | | |
|---|---|---|
| PATENT NO. | : 8,257,707 B2 | Page 1 of 1 |
| APPLICATION NO. | : 12/670112 | |
| DATED | : September 4, 2012 | |
| INVENTOR(S) | : Dirk E. Smith et al. | |

It is certified that error appears in the above-identified patent and that said Letters Patent is hereby corrected as shown below:

On the Title Page

Item (75) Inventors: "Duncan Cochrane, Granta Park (GA); Louise Conroy, Granta Park (GA)" should read -- Duncan Cochrane, Cambridge (UK); Louise Conroy, Cambridge (UK) --.

In the Claims

Col. 181,
Claim 4, lines 33-34: "a monoclonal antibody, a recombinant antibody" should read -- a monoclonal antibody, a human antibody, a recombinant antibody, a chimeric antibody, a humanized antibody, --.

Col. 181,
Claim 11, line 54: "the antigen" should read -- an antigen --.

Signed and Sealed this
Fifteenth Day of July, 2014

Michelle K. Lee
*Deputy Director of the United States Patent and Trademark Office*

SEQUENCE LISTING

<160> NUMBER OF SEQ ID NOS: 292

<210> SEQ ID NO 1
<211> LENGTH: 122
<212> TYPE: PRT
<213> ORGANISM: Homo sapiens

<400> SEQUENCE: 1

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

```
Gly Met His Trp Val Arg Gln Ala Pro Gly Lys Gly Leu Glu Trp Val
            35                  40                  45

Ala Val Ile Ser Asn Asp Gly Ser Lys Lys Tyr Tyr Ser Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Ser Ser Ile Trp Leu Thr Gln Ser Leu Asp His Trp
                100                 105                 110

Gly Gln Gly Thr Thr Val Thr Val Ser Ser
            115                 120

<210> SEQ ID NO 2
<211> LENGTH: 122
<212> TYPE: PRT
<213> ORGANISM: Homo sapiens

<400> SEQUENCE: 2

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
            35                  40                  45

Ala Val Ile Ser Asn Asp Gly Ser Lys Lys Tyr Tyr Ser Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Ser Ser Ile Trp Leu Thr Gln Ser Leu Asp His Trp
                100                 105                 110

Gly Gln Gly Thr Thr Val Thr Val Ser Ser
            115                 120

<210> SEQ ID NO 3
<211> LENGTH: 122
<212> TYPE: PRT
<213> ORGANISM: Homo sapiens

<400> SEQUENCE: 3

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
            35                  40                  45

Ala Val Ile Ser Asn Asp Gly Ser Lys Lys Tyr Tyr Ser Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Ser Ser Ile Trp Leu Ser Gln Ser Leu Asp Gly Trp
                100                 105                 110
```

```
Gly Gln Gly Thr Thr Val Thr Val Ser Ser
        115                 120

<210> SEQ ID NO 4
<211> LENGTH: 122
<212> TYPE: PRT
<213> ORGANISM: Homo sapiens

<400> SEQUENCE: 4

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
        35                  40                  45

Ala Val Ile Ser Asn Asp Gly Ser Lys Lys Tyr Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Ser Ser Ile Trp Leu Ser Gln Ser Leu Asp Gly Trp
            100                 105                 110

Gly Gln Gly Thr Thr Val Thr Val Ser Ser
        115                 120

<210> SEQ ID NO 5
<211> LENGTH: 122
<212> TYPE: PRT
<213> ORGANISM: Homo sapiens

<400> SEQUENCE: 5

Gln Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
        35                  40                  45

Ala Val Ile Ser Asn Asp Gly Ser Lys Lys Tyr Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Ser Ser Ile Trp Leu Thr Ser Ala Leu Asn Leu Trp
            100                 105                 110

Gly Gln Gly Thr Thr Val Thr Val Ser Ser
        115                 120

<210> SEQ ID NO 6
<211> LENGTH: 122
<212> TYPE: PRT
<213> ORGANISM: Homo sapiens

<400> SEQUENCE: 6

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30
```

Gly Met His Trp Val Arg Gln Ala Pro Gly Lys Gly Leu Glu Trp Val
            35                  40                  45

Ala Val Ile Ser Asn Asp Gly Ser Lys Lys Tyr Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Ser Ser Ile Trp Leu Thr Ser Ala Leu Asn Leu Trp
            100                 105                 110

Gly Gln Gly Thr Thr Val Thr Val Ser Ser
            115                 120

<210> SEQ ID NO 7
<211> LENGTH: 117
<212> TYPE: PRT
<213> ORGANISM: Homo sapiens

<400> SEQUENCE: 7

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
            35                  40                  45

Ala Val Ile Ser Asn Asp Gly Ser Lys Lys Tyr Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Lys Gly Ser Ser Ser Ile Trp Phe Gly Glu Thr Val Asp Tyr Trp
            100                 105                 110

Gly Gln Gly Thr Thr
            115

<210> SEQ ID NO 8
<211> LENGTH: 121
<212> TYPE: PRT
<213> ORGANISM: Homo sapiens

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
            35                  40                  45

Gly Gly Phe Asp Arg Glu Asp Asp Glu Thr Ile His Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Met Val Trp Gly Asp Phe Trp Ile Gln His Trp Gly
            100                 105                 110

-continued

Gln Gly Thr Leu Val Thr Val Ser Ser
        115                 120

<210> SEQ ID NO 9
<211> LENGTH: 121
<212> TYPE: PRT
<213> ORGANISM: Homo sapiens

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Arg Glu Asp Asp Glu Thr Ile His Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Met Val Trp Gly Asp Phe Trp Ile Gln His Trp Gly
            100                 105                 110

Gln Gly Thr Leu Val Thr Val Ser Ser
        115                 120

<210> SEQ ID NO 10
<211> LENGTH: 121
<212> TYPE: PRT
<213> ORGANISM: Homo sapiens

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Arg Glu Asp Asp Glu Thr Ile His Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Met Ala Trp Asp Tyr Pro Pro Ile Gln His Trp Gly
            100                 105                 110

Gln Gly Thr Leu Val Thr Val Ser Ser
        115                 120

<210> SEQ ID NO 11
<211> LENGTH: 121
<212> TYPE: PRT
<213> ORGANISM: Homo sapiens

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
            35                  40                  45

Gly Gly Phe Asp Arg Glu Asp Asp Glu Thr Ile His Ala Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Met Val Trp Asn Phe Pro Pro Ile Gln His Trp Gly
            100                 105                 110

Gln Gly Thr Leu Val Thr Val Ser Ser
            115                 120

<210> SEQ ID NO 12
<211> LENGTH: 116
<212> TYPE: PRT
<213> ORGANISM: Homo sapiens

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
            35                  40                  45

Gly Gly Phe Asp Arg Glu Asp Asp Glu Thr Ile His Ala Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Met Val Trp Gly Asp Phe Trp Ile Gln His Trp Gly
            100                 105                 110

Lys Gly Thr Met
            115

<210> SEQ ID NO 13
<211> LENGTH: 118
<212> TYPE: PRT
<213> ORGANISM: Homo sapiens

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Arg Gly Asp Tyr Arg Thr Asp Ile Trp Gly Gln Gly Thr
            100                 105                 110

-continued

Thr Val Thr Val Ser Ser
        115

<210> SEQ ID NO 14
<211> LENGTH: 118
<212> TYPE: PRT
<213> ORGANISM: Homo sapiens

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Arg Gly Asp Tyr Arg Thr Asp Ile Trp Gly Arg Gly Thr
            100                 105                 110

Leu Val Thr Val Ser Ser
        115

<210> SEQ ID NO 15
<211> LENGTH: 118
<212> TYPE: PRT
<213> ORGANISM: Homo sapiens

<400> SEQUENCE: 15

Glu Val Gln Leu Leu Glu Ser Gly Gly Gly Leu Ala Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Arg Gly Asp Tyr Arg Thr Asp Ile Trp Gly Arg Gly Thr
            100                 105                 110

Leu Val Thr Val Ser Ser
        115

<210> SEQ ID NO 16
<211> LENGTH: 118
<212> TYPE: PRT
<213> ORGANISM: Homo sapiens

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Arg Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Arg Gly Asp Tyr Arg Thr Asp Ile Trp Gly Arg Gly Thr
            100                 105                 110

Leu Val Thr Val Ser Ser
            115

<210> SEQ ID NO 17
<211> LENGTH: 113
<212> TYPE: PRT
<213> ORGANISM: Homo sapiens

<400> SEQUENCE: 17

Glu Val Gln Leu Leu Glu Ser Gly Gly Gly Leu Val Gln Pro Gly Gly
 1               5                  10                  15

Ser Leu Arg Leu Ser Cys Ala Ala Ser Arg Phe Thr Phe Ser Ser Tyr
             20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Arg Gly Ile Tyr Gly Met Asp Val Trp Gly Arg Gly Thr
            100                 105                 110

Leu

<210> SEQ ID NO 18
<211> LENGTH: 103
<212> TYPE: PRT
<213> ORGANISM: Homo sapiens

<400> SEQUENCE: 18

Gln Pro Val Leu Thr Gln Pro Ser Val Ser Val Ser Pro Gly Gln
 1               5                  10                  15

Thr Ala Ser Ile Thr Cys Ser Gly Asp Lys Leu Gly Asp Lys Tyr Ala
             20                  25                  30

Ser Trp Tyr Gln Gln Lys Pro Gly Lys Ser Pro Val Leu Val Ile Tyr
        35                  40                  45

Gln Asp Ser Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Arg
 65                  70                  75                  80

Asp Glu Ala Asp Tyr Tyr Cys Gln Ala Trp Asp Ser Ser Thr Ala Ser
                 85                  90                  95

Val Phe Gly Gly Gly Thr Lys
            100

```
<210> SEQ ID NO 19
<211> LENGTH: 108
<212> TYPE: PRT
<213> ORGANISM: Homo sapiens

<400> SEQUENCE: 19

Gln Pro Val Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Ser Trp Tyr Gln Gln Lys Pro Gly Lys Ser Pro Val Leu Val Ile Tyr
        35                  40                  45

Gln Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Arg
65                  70                  75                  80

Asp Glu Ala Asp Tyr Tyr Cys Gln Ala Trp Asp His Ser Leu Gln His
                85                  90                  95

Arg Phe Gly Gly Gly Thr Lys Val Thr Val Leu Gly
            100                 105

<210> SEQ ID NO 20
<211> LENGTH: 108
<212> TYPE: PRT
<213> ORGANISM: Homo sapiens

<400> SEQUENCE: 20

Gln Pro Val Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Ser Trp Tyr Gln Gln Lys Pro Gly Gln Thr Pro Val Leu Val Ile Tyr
        35                  40                  45

Gln Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Arg
65                  70                  75                  80

Asp Glu Ala Asp Tyr Tyr Cys Gln Ala Trp Thr Ser Ala Leu Asn Ser
                85                  90                  95

Gln Phe Gly Gly Gly Thr Lys Val Thr Val Leu Gly
            100                 105

<210> SEQ ID NO 21
<211> LENGTH: 108
<212> TYPE: PRT
<213> ORGANISM: Homo sapiens

<400> SEQUENCE: 21

Gln Pro Val Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Ser Trp Tyr Gln Gln Lys Pro Gly Gln Ser Pro Val Leu Val Ile Tyr
        35                  40                  45

Gln Asp Ser Asn Arg Pro Ser Gly Ile Pro Glu Arg Phe Ser Gly Ser
    50                  55                  60

Asn Ser Gly Asp Thr Ala Thr Leu Thr Ile Ser Gly Thr Gln Ala Arg
65                  70                  75                  80
```

```
Asp Glu Ala Asp Tyr Tyr Cys Gln Ala Trp Thr His Ser Leu Ser Thr
            85                  90                  95

Leu Phe Gly Gly Gly Thr Lys Val Thr Val Leu Gly
        100                 105

<210> SEQ ID NO 22
<211> LENGTH: 108
<212> TYPE: PRT
<213> ORGANISM: Homo sapiens

<400> SEQUENCE: 22

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Ser Trp Tyr Gln Gln Lys Pro Gly Gln Ser Pro Val Leu Val Ile Tyr
        35                  40                  45

Gln Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Thr His Ser Leu Ser Thr
            85                  90                  95

Leu Phe Gly Gly Gly Thr Lys Leu Thr Val Leu Gly
        100                 105

<210> SEQ ID NO 23
<211> LENGTH: 106
<212> TYPE: PRT
<213> ORGANISM: Homo sapiens

<400> SEQUENCE: 23

Gln Ser Val Leu Thr Gln Pro Pro Ser Ala Ser Gly Thr Pro Gly Gln
1               5                   10                  15

Arg Val Thr Ile Ser Cys Ser Gly Arg Asn Ser Asn Ile Gly Ser Tyr
            20                  25                  30

Thr Val Thr Trp Tyr Gln Gln Leu Pro Gly Thr Ala Pro Lys Leu Leu
        35                  40                  45

Ile Tyr Ser Asn Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
            85                  90                  95

Asn Gly Pro Val Phe Gly Gly Gly Thr Lys
        100                 105

<210> SEQ ID NO 24
<211> LENGTH: 111
<212> TYPE: PRT
<213> ORGANISM: Homo sapiens

<400> SEQUENCE: 24

Gln Ser Val Leu Thr Gln Pro Pro Ser Ala Ser Gly Thr Pro Gly Gln
1               5                   10                  15

Arg Val Thr Ile Ser Cys Ser Gly Arg Asn Ser Asn Ile Gly Ser Tyr
            20                  25                  30

Thr Val Thr Trp Tyr Gln Gln Leu Pro Gly Thr Ala Pro Lys Leu Leu
        35                  40                  45
```

```
Ile Tyr Ser Asn Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Val Val Trp Asp Asp Val Leu
                 85                  90                  95

Asn Gly Pro Val Phe Gly Gly Gly Thr Lys Leu Thr Val Leu Gly
            100                 105                 110

<210> SEQ ID NO 25
<211> LENGTH: 111
<212> TYPE: PRT
<213> ORGANISM: Homo sapiens

<400> SEQUENCE: 25

Gln Ser Val Leu Thr Gln Pro Pro Ser Ala Ser Gly Thr Pro Gly Gln
 1               5                  10                  15

Arg Val Thr Ile Ser Cys Ser Gly Arg Asn Ser Asn Ile Gly Ser Tyr
                20                  25                  30

Thr Val Thr Trp Tyr Gln Gln Leu Pro Gly Thr Ala Pro Lys Leu Leu
            35                  40                  45

Ile Tyr Ser Asn Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Val Val Trp Asp Asp Lys Leu
                 85                  90                  95

Asn Gly Pro Val Phe Gly Gly Gly Thr Lys Leu Thr Val Leu Gly
            100                 105                 110

<210> SEQ ID NO 26
<211> LENGTH: 111
<212> TYPE: PRT
<213> ORGANISM: Homo sapiens

<400> SEQUENCE: 26

Gln Ser Val Leu Thr Gln Pro Pro Ser Ala Ser Gly Thr Pro Gly Gln
 1               5                  10                  15

Arg Val Thr Ile Ser Cys Ser Gly Arg Asn Ser Asn Ile Gly Ser Tyr
                20                  25                  30

Thr Val Thr Trp Tyr Gln Gln Leu Pro Gly Thr Ala Pro Lys Leu Leu
            35                  40                  45

Ile Tyr Ser Asn Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Val Val Trp Asp Glu Ile Leu
                 85                  90                  95

Asn Gly Pro Val Phe Gly Gly Gly Thr Lys Leu Thr Val Leu Gly
            100                 105                 110

<210> SEQ ID NO 27
<211> LENGTH: 103
<212> TYPE: PRT
<213> ORGANISM: Homo sapiens

<400> SEQUENCE: 27

Ser Ser Glu Leu Thr Gln Asp Pro Ala Val Ser Val Ala Leu Gly Gln
```

```
                1               5                   10                  15
Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Ser
            35                  40                  45

Ala Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Asn His Val
                85                  90                  95

Val Phe Gly Gly Gly Thr Lys
                100
```

<210> SEQ ID NO 28
<211> LENGTH: 111
<212> TYPE: PRT
<213> ORGANISM: Homo sapiens

<400> SEQUENCE: 28

```
Gln Ser Val Leu Thr Gln Pro Pro Ser Ala Ser Gly Thr Pro Gly Gln
1               5                   10                  15

Arg Val Thr Ile Ser Cys Ser Gly Arg Asn Ser Asn Ile Gly Ser Tyr
                20                  25                  30

Thr Val Thr Trp Tyr Gln Gln Leu Pro Gly Thr Ala Pro Lys Leu Leu
            35                  40                  45

Ile Tyr Ser Asn Ser Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Leu Val Trp Asp Asp Val Leu
                85                  90                  95

Asn Gly Pro Val Phe Gly Gly Gly Thr Lys Leu Thr Val Leu Gly
                100                 105                 110
```

<210> SEQ ID NO 29
<211> LENGTH: 108
<212> TYPE: PRT
<213> ORGANISM: Homo sapiens

<400> SEQUENCE: 29

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Ser
            35                  40                  45

Ala Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Ala Ser Arg Asn Gly Trp Asn His Val
                85                  90                  95

Val Phe Gly Gly Gly Thr Lys Leu Thr Val Leu Gly
                100                 105
```

<210> SEQ ID NO 30

```
<211> LENGTH: 108
<212> TYPE: PRT
<213> ORGANISM: Homo sapiens

<400> SEQUENCE: 30

Ser Ser Glu Leu Thr Gln Asp Pro Ala Val Ser Val Ala Leu Gly Gln
1               5                   10                  15

Thr Val Arg Val Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Ser
        35                  40                  45

Ala Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Ala Ser Arg Asn Gly Trp Asn His Val
                85                  90                  95

Val Phe Gly Gly Gly Thr Lys Leu Thr Val Leu Gly
            100                 105

<210> SEQ ID NO 31
<211> LENGTH: 108
<212> TYPE: PRT
<213> ORGANISM: Homo sapiens

<400> SEQUENCE: 31

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Ser
        35                  40                  45

Ala Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Ala Ser Arg Asn Gly Trp Asn His Val
                85                  90                  95

Val Phe Gly Gly Gly Thr Lys Leu Thr Val Leu Gly
            100                 105

<210> SEQ ID NO 32
<211> LENGTH: 108
<212> TYPE: PRT
<213> ORGANISM: Homo sapiens

<400> SEQUENCE: 32

Ser Ser Glu Leu Thr Gln Asp Pro Ala Val Ser Val Ala Leu Gly Gln
1               5                   10                  15

Thr Val Arg Val Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Ser
        35                  40                  45

Ala Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Ala Ser Arg Asn Gly Trp Asn His Val
```

```
                       85                  90                  95
Val Phe Gly Gly Gly Thr Lys Leu Thr Val Leu Gly
                100                 105

<210> SEQ ID NO 33
<211> LENGTH: 108
<212> TYPE: PRT
<213> ORGANISM: Homo sapiens

<400> SEQUENCE: 33

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Ser
        35                  40                  45

Ala Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Ala Thr Arg Asn Gly Trp Asn His Val
                85                  90                  95

Val Phe Gly Gly Gly Thr Lys Leu Thr Val Leu Gly
                100                 105

<210> SEQ ID NO 34
<211> LENGTH: 108
<212> TYPE: PRT
<213> ORGANISM: Homo sapiens

<400> SEQUENCE: 34

Ser Ser Glu Leu Thr Gln Asp Pro Ala Val Ser Val Ala Leu Gly Gln
1               5                   10                  15

Thr Val Arg Val Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Ser
        35                  40                  45

Ala Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Ala Thr Arg Asn Gly Trp Asn His Val
                85                  90                  95

Val Phe Gly Gly Gly Thr Lys Leu Thr Val Leu Gly
                100                 105

<210> SEQ ID NO 35
<211> LENGTH: 366
<212> TYPE: DNA
<213> ORGANISM: Homo sapiens

<400> SEQUENCE: 35
caggtgcagc tggtgcagtc tgggggaggc gtggtccagc ctgggaggtc cctgagactc      60
tcctgtgcag cgtctggatt caccttcagc ggttatggca tgcactgggt ccgccaggct     120
ccaggcaagg ggctggagtg ggtggcagta atatcaaatg atggaagtaa gaaatattat     180
tcagactccg tgaagggccg attcaccatc tccagagaca attccaaaaa cacgctgtat     240
ctgcagatga acagcctgag agctgaggac acggctgtat attactgtgc gaaagggtcc     300
```
agttccatat ggctgaccca gtccctggac cactgggggc aggggaccac ggtcaccgtc    360
tcctca    366

<210> SEQ ID NO 36
<211> LENGTH: 366
<212> TYPE: DNA
<213> ORGANISM: Homo sapiens

<400> SEQUENCE: 36
gaggtgcagc tggtggagtc tgggggaggc gtggtccagc ctgggaggtc cctgagactc    60
tcctgtgcag cgtctggatt caccttcagc ggttatggca tgcactgggt ccgccaggct    120
ccaggcaagg ggctggagtg gtggcagta atatcaaatg atggaagtaa gaaatattat    180
tcagactccg tgaagggccg attcaccatc tccagagaca attccaaaaa cacgctgtat    240
ctgcagatga acagcctgag agctgaggac acggctgtat attactgtgc gaaagggtcc    300
agttccatat ggctgaccca gtccctggac cactgggggc aggggaccac ggtcaccgtc    360
tcctca    366

<210> SEQ ID NO 37
<211> LENGTH: 366
<212> TYPE: DNA
<213> ORGANISM: Homo sapiens

<400> SEQUENCE: 37
caggtgcagc tggtgcagtc tgggggaggc gtggtccagc ctgggaggtc cctgagactc    60
tcctgtgcag cgtctggatt caccttcagc ggttatggca tgcactgggt ccgccaggct    120
ccaggcaagg ggctggagtg gtggcagta atatcaaatg atggaagtaa gaaatattat    180
tcagactccg tgaagggccg attcaccatc tccagagaca attccaaaaa cacgctgtat    240
ctgcagatga acagcctgag agctgaggac acggctgtat attactgtgc gaaagggtcc    300
agttccatat ggctgtcgca gtccctggac ggctgggggc aggggaccac ggtcaccgtc    360
tcctca    366

<210> SEQ ID NO 38
<211> LENGTH: 366
<212> TYPE: DNA
<213> ORGANISM: Homo sapiens

<400> SEQUENCE: 38
gaggtgcagc tggtggagtc tgggggaggc gtggtccagc ctgggaggtc cctgagactc    60
tcctgtgcag cgtctggatt caccttcagc ggttatggca tgcactgggt ccgccaggct    120
ccaggcaagg ggctggagtg gtggcagta atatcaaatg atggaagtaa gaaatattat    180
tcagactccg tgaagggccg attcaccatc tccagagaca attccaaaaa cacgctgtat    240
ctgcagatga acagcctgag agctgaggac acggctgtat attactgtgc gaaagggtcc    300
agttccatat ggctgtcgca gtccctggac ggctgggggc aggggaccac ggtcaccgtc    360
tcctca    366

<210> SEQ ID NO 39
<211> LENGTH: 366
<212> TYPE: DNA
<213> ORGANISM: Homo sapiens

<400> SEQUENCE: 39
caggtgcagc tggtgcagtc tgggggaggc gtggtccagc ctgggaggtc cctgagactc    60

```
tcctgtgcag cgtctggatt caccttcagc ggttatggca tgcactgggt ccgccaggct    120
ccaggcaagg ggctggagtg ggtggcagta atatcaaatg atggaagtaa gaaatattat    180
tcagactccg tgaagggccg attcaccatc tccagagaca attccaaaaa cacgctgtat    240
ctgcagatga acagcctgag agctgaggac acggctgtat attactgtgc gaaagggtcc    300
agttccatat ggctgacctc ggccctgaac ctgtgggggc aggggaccac ggtcaccgtc    360
tcctca                                                                366
```

<210> SEQ ID NO 40
<211> LENGTH: 366
<212> TYPE: DNA
<213> ORGANISM: Homo sapiens

<400> SEQUENCE: 40

```
gaggtgcagc tggtggagtc tgggggaggc gtggtccagc ctgggaggtc cctgagactc     60
tcctgtgcag cgtctggatt caccttcagc ggttatggca tgcactgggt ccgccaggct    120
ccaggcaagg ggctggagtg ggtggcagta atatcaaatg atggaagtaa gaaatattat    180
tcagactccg tgaagggccg attcaccatc tccagagaca attccaaaaa cacgctgtat    240
ctgcagatga acagcctgag agctgaggac acggctgtat attactgtgc gaaagggtcc    300
agttccatat ggctgacctc ggccctgaac ctgtgggggc aggggaccac ggtcaccgtc    360
tcctca                                                                366
```

<210> SEQ ID NO 41
<211> LENGTH: 351
<212> TYPE: DNA
<213> ORGANISM: Homo sapiens

<400> SEQUENCE: 41

```
gaggtgcagc tggtggagtc tgggggaggc gtggtccagc ctgggaggtc cctgagactc     60
tcctgtgcag cgtctggatt caccttcagc ggttatggca tgcactgggt ccgccaggct    120
ccaggcaagg ggctggagtg ggtggcagta atatcaaatg atggaagtaa gaaatattat    180
tcagactccg tgaagggccg attcaccatc tccagagaca attccaaaaa cacgctgtat    240
ctgcagatga acagcctgag agctgaggac acggctatat attactgtgc gaaagggtcc    300
agttccatat ggttcgggga gaccgttgac tactgggggc aggggaccac g             351
```

<210> SEQ ID NO 42
<211> LENGTH: 363
<212> TYPE: DNA
<213> ORGANISM: Homo sapiens

<400> SEQUENCE: 42

```
caggtgcagc tggtgcagtc tggggctgag gtgaagaagc ctggggcctc agtgaaggtc     60
tcctgcaagg tttccggata cacctcact  gaattatcca tgcactgggt gcgacaggct    120
cctggaaaag ggcttgagtg gatgggaggt tttgatcgtg aagatgatga acaatccac    180 gcacagaagt tccagggcag agtcaccatg accgaggaca catctacaga cacagcctac    240
atggaactga gcagcctgcg atctgaggac acggccgttt attactgtgc aacagatctt    300
atggtgtggg gcgatttttg gatccagcac tggggccagg gacactggt caccgtctcc    360 tca                                                                   363
```

<210> SEQ ID NO 43
<211> LENGTH: 363

```
<212> TYPE: DNA
<213> ORGANISM: Homo sapiens

<400> SEQUENCE: 43
caggtgcagc tggtgcagtc tggggctgag gtgaagaagc ctggggcctc agtgaaggtc      60
tcctgcaagg tttccggata caccctcact gaattatcca tgcactgggt gcgacaggct     120
cctggaaaag ggcttgagtg gatgggaggt tttgatcgtg aagatgatga aacaatccac     180
gcacagaagt tccagggcag agtcaccatg accgaggaca catctacaga cacagcctac     240
atggaactga gcagcctgcg atctgaggac acggccgttt attactgtgc aacagatctt     300
atggtgtggg gcgattttg gatccagcac tggggccagg ggacactggt caccgtctcc      360
tca                                                                   363

<210> SEQ ID NO 44
<211> LENGTH: 363
<212> TYPE: DNA
<213> ORGANISM: Homo sapiens

<400> SEQUENCE: 44
caggtgcagc tggtgcagtc tggggctgag gtgaagaagc ctggggcctc agtgaaggtc      60
tcctgcaagg tttccggata caccctcact gaattatcca tgcactgggt gcgacaggct     120
cctggaaaag ggcttgagtg gatgggaggt tttgatcgtg aagatgatga aacaatccac     180
gcacagaagt tccagggcag agtcaccatg accgaggaca catctacaga cacagcctac     240
atggaactga gcagcctgcg atctgaggac acggccgttt attactgtgc aacagatctt     300
atggcctggg actacccgcc catccagcac tggggccagg ggacactggt caccgtctcc     360
tca                                                                   363

<210> SEQ ID NO 45
<211> LENGTH: 363
<212> TYPE: DNA
<213> ORGANISM: Homo sapiens

<400> SEQUENCE: 45
caggtgcagc tggtgcagtc tggggctgag gtgaagaagc ctggggcctc agtgaaggtc      60
tcctgcaagg tttccggata caccctcact gaattatcca tgcactgggt gcgacaggct     120
cctggaaaag ggcttgagtg gatgggaggt tttgatcgtg aagatgatga aacaatccac     180
gcacagaagt tccagggcag agtcaccatg accgaggaca catctacaga cacagcctac     240
atggaactga gcagcctgcg atctgaggac acggccgttt attactgtgc aacagatctt     300
atggtgtgga acttcccccc catccagcac tggggccagg ggacactggt caccgtctcc     360
tca                                                                   363

<210> SEQ ID NO 46
<211> LENGTH: 348
<212> TYPE: DNA
<213> ORGANISM: Homo sapiens

<400> SEQUENCE: 46
caggtgcagc tggtgcagtc tggggctgag gtgaagaagc ctggggcctc agtgaaggtc      60
tcctgcaagg tttccggata caccctcact gaattatcca tgcactgggt gcgacaggct     120
cctggaaaag ggcttgagtg gatgggaggt tttgatcgtg aagatgatga aacaatccac     180
gcacagaagt tccagggcag agtcaccatg accgaggaca catctacaga cacagcctac     240
atggaactga gcagcctgcg atctgaggac acggccgttt attactgtgc aacagatctt     300
```

```
atggtgtggg gcgattttg gatccagcac tggggcaagg ggacaatg            348
```

<210> SEQ ID NO 47
<211> LENGTH: 354
<212> TYPE: DNA
<213> ORGANISM: Homo sapiens

<400> SEQUENCE: 47

```
gaggtgcagc tgttggagtc tgggggaggc ttggtacagc ctgggggtc cctgagactc    60
tcctgtgcag cctctggatt cacctttagc agctatgcca tgagctgggt ccgccaggct  120
ccagggaagg ggctggagtg ggtctcagct attagtggta gtggtggtgg cacatactac  180
gcagactccg tgaagggccg gttcaccatc tccagagaca attccaagaa cacgctgtat  240
ctgcaaatga acagcctgag agccgaggac acggccgtgt attactgtgc gagaattcgg  300
ggcgactacc ggacggacat ctggggccag ggaaccacgg tcaccgtctc ctca        354
```

<210> SEQ ID NO 48
<211> LENGTH: 354
<212> TYPE: DNA
<213> ORGANISM: Homo sapiens

<400> SEQUENCE: 48

```
gaggtgcagc tgttggagtc tgggggaggc ttggtacagc ctgggggtc cctgagactc    60
tcctgtgcag cctctggatt cacctttagc agctatgcca tgagctgggt ccgccaggct  120
ccagggaagg ggctggagtg ggtctcagct attagtggta gtggtggtgg cacatactac  180
gcagactccg tgaagggccg gtccaccatc tccagagaca attccaagaa cacgctgtat  240
ctgcaaatga acagcctgag agccgaggac acggccgtgt attactgtgc gagaattcgg  300
ggggactacc ggacggacat ctggggccgg ggaaccctgg tcaccgtctc ctca        354
```

<210> SEQ ID NO 49
<211> LENGTH: 354
<212> TYPE: DNA
<213> ORGANISM: Homo sapiens

<400> SEQUENCE: 49

```
gaggtgcagc tgttggagtc tgggggaggc ttggcacagc ctgggggtc cctgagactc    60
tcctgtgcag cctctgggtt cacctttagc agctatgcca tgagctgggt ccgccaggct  120
ccagggaagg ggctggagtg ggtctcagct attagtggta gtggtggtag cacatactac  180
gcagactccg tgaagggccg gttcaccatc tccagagaca attccaagaa cacgctgtat  240
ctgcaaatga acagcctgag agccgaggac acggccgtgt attactgtgc gagagttcgg  300
ggggactacc ggacggacat ctggggccgg ggaaccctgg tcaccgtctc ctca        354
```

<210> SEQ ID NO 50
<211> LENGTH: 354
<212> TYPE: DNA
<213> ORGANISM: Homo sapiens

<400> SEQUENCE: 50

```
gaggtgcagc tgttggagtc tgggggaggc ttggtacagc ctgggggtc cctgagactc    60
tcctgtgcag cctctagatt cacctttagc agctatgcca tgagctgggt ccgccaggct  120
ccagggaagg ggctggagtg ggtctcagct attagtggta gtggtggtag cacatactac  180
gcagactccg tgaagggccg gttcaccatc tccagagaca attccaagaa cacgctgtat  240
ctgcaaatga acagcctgag agccgaggac acggccgtgt attactgtgc gagagttcgg  300
```

```
ggggactacc ggacggacat ctggggccgg ggaaccctgg tcaccgtctc ctca        354

<210> SEQ ID NO 51
<211> LENGTH: 339
<212> TYPE: DNA
<213> ORGANISM: Homo sapiens

<400> SEQUENCE: 51
gaggtgcagc tgttggagtc tgggggaggc ttggtacagc ctggggggtc cctgagactc    60
tcctgtgcag cctctagatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtgt attactgtgc gagagttcgg   300
ggcatatacg gtatggacgt ctggggccgg ggaaccctg                          339

<210> SEQ ID NO 52
<211> LENGTH: 309
<212> TYPE: DNA
<213> ORGANISM: Homo sapiens

<400> SEQUENCE: 52
cagcctgtgc tgactcagcc cccctcagtg tccgtgtccc caggacagac tgccagcatc    60
acctgctctg gagataaatt gggggataaa tatgcttcct ggtatcagca gaagccaggc   120
aagtcccctg tactggtcat ctatcaagat tccaatcggc cctcagggat ccctgagcga   180
ttctctggct ccaactctgg gaacacagcc actctgacca tcagcgggac ccaggctagg   240
gatgaggctg actattactg tcaggcgtgg gacagcagca ctgcatcggt gttcggcgga   300
gggaccaag                                                           309

<210> SEQ ID NO 53
<211> LENGTH: 324
<212> TYPE: DNA
<213> ORGANISM: Homo sapiens

<400> SEQUENCE: 53
cagcctgtgc tgactcagcc cccctcagtg tccgtgtccc caggacagac tgccagcatc    60
acctgctctg gagataaatt gggggataaa tatgcttcct ggtatcagca gaagccaggc   120
aagtcccctg tactggtcat ctatcaagat tccaatcggc cctcagggat ccctgagcga   180
ttctctggct ccaactctgg gaacacagcc actctgacca tcagcgggac ccaggctagg   240
gatgaggctg actattactg tcaggcgtgg gaccactcct tgcagcacag gttcggcgga   300
gggaccaagg tcaccgtcct aggt                                          324

<210> SEQ ID NO 54
<211> LENGTH: 324
<212> TYPE: DNA
<213> ORGANISM: Homo sapiens

<400> SEQUENCE: 54
cagcctgtgc tgactcagcc cccctcagtg tccgtgtccc caggacagac tgccagcatc    60
acctgctctg gagataaatt gggggataaa tatgcttcct ggtatcagca gaagccaggc   120
cagacccctg tactggtcat ctatcaagat tccaatcggc cctcagggat ccctgagcga   180
ttctctggct ccaactccgg gaacacagcc actctgacca tcagcgggac ccaggctagg   240
gatgaggctg actattactg tcaggcgtgg accagcgccc tgaactcgca gttcggcgga   300
```

```
gggaccaagg tcaccgtcct aggt                                            324

<210> SEQ ID NO 55
<211> LENGTH: 324
<212> TYPE: DNA
<213> ORGANISM: Homo sapiens

<400> SEQUENCE: 55
cagcctgtgc tgactcagcc cccctcagtg tccgtgtccc caggacagac tgccagcatc      60
acctgctctg gagataaaat tgggggataaa tatgcttcct ggtatcagca gaagccaggc     120
cagtcccctg tactggtcat ctatcaagat tccaatcggc cctcagggat ccctgagcga     180
ttctctggct ccaactctgg gacacagcc actctgacca tcagcgggac ccaggctagg      240
gatgaggctg actattactg tcaggcgtgg acgcactccc tcagcacgtt gttcggcgga     300
gggaccaagg tcaccgtcct aggt                                            324

<210> SEQ ID NO 56
<211> LENGTH: 324
<212> TYPE: DNA
<213> ORGANISM: Homo sapiens

<400> SEQUENCE: 56
tcctatgagc tgactcagcc cccctcagtg tccgtgtccc caggacagac tgccagcatc      60
acctgctctg gagataaaat tgggggataaa tatgcttcct ggtatcagca gaagccaggc     120
cagtcccctg tactggtcat ctatcaagat tccaatcggc cctcagggat ccctgagcga     180
ttctctggct ccaactctgg gaacacagcc actctgacca tcagcgggac ccaggctatg     240
gatgaggctg actattactg tcaggcgtgg acccacagcc tgagcacgtt gttcggcgga     300
gggaccaagc tgaccgtcct aggt                                            324

<210> SEQ ID NO 57
<211> LENGTH: 318
<212> TYPE: DNA
<213> ORGANISM: Homo sapiens

<400> SEQUENCE: 57
cagtctgtgc tgactcagcc accctcagcg tctgggaccc ccgggcagag ggtcaccatc      60
tcttgttctg gaaggaactc caacatcgga agttatactg taacctggta ccagcagctc     120
ccaggaacgg cccccaaact cctcatctat agtaatagtc agcggccctc agggtccct     180 gaccgattct caggctccaa gtctggcacc tcagcctcct ggccatcag tgggctccag     240 tctgaagatg aggctgatta ttactgtgca gcatgggatg acagcctgaa tggcccggtg    300
ttcggcggag ggaccaag                                                   318

<210> SEQ ID NO 58
<211> LENGTH: 333
<212> TYPE: DNA
<213> ORGANISM: Homo sapiens

<400> SEQUENCE: 58
cagtctgtgc tgactcagcc accctcagcg tctgggaccc ccgggcagag ggtcaccatc      60
tcttgttctg gaaggaactc caacatcgga agttatactg taacctggta ccagcagctc     120
ccaggaacgg cccccaaact cctcatctat agtaatagtc agcggccctc agggtccct     180 gaccgattct caggctccaa gtctggcacc tcagcctcct ggccatcag tgggctccag     240 tctgaagatg aggctgatta ttactgtgtg gtgtgggatg acgtgctgaa tggcccggtg    300
```

```
ttcggcggag ggaccaagct gaccgtccta ggt                                   333
```

<210> SEQ ID NO 59
<211> LENGTH: 333
<212> TYPE: DNA
<213> ORGANISM: Homo sapiens

<400> SEQUENCE: 59

```
cagtctgtgc tgactcagcc accctcagcg tctgggaccc ccgggcagag ggtcaccatc     60
tcttgttctg gaaggaactc caacatcgga agttatactg taacctggta ccagcagctc   120
ccaggaacgg cccccaaact cctcatctat agtaatagtc agcggccctc aggggtccct   180
gaccgattct caggctccaa gtctggcacc tcagcctcct tggccatcag tgggctccag   240
tctgaagatg aggctgatta ttactgtgtc gtgtgggatg acaagctgaa tggcccggtg   300
ttcggcggag ggaccaagct gaccgtccta ggt                                  333
```

<210> SEQ ID NO 60
<211> LENGTH: 333
<212> TYPE: DNA
<213> ORGANISM: Homo sapiens

<400> SEQUENCE: 60

```
cagtctgtgc tgactcagcc accctcagcg tctgggaccc ccgggcagag ggtcaccatc     60
tcttgttctg gaaggaactc caacatcgga agttatactg taacctggta ccagcagctc   120
ccaggaacgg cccccaaact cctcatctat agtaatagtc agcggccctc aggggtccct   180
gaccgattct caggctccaa gtctggcacc tcagcctcct tggccatcag tgggctccag   240
tctgaagatg aggctgatta ttactgtgtg gtgtgggacg agatcctgaa tggcccggtg   300
ttcggcggag ggaccaagct gaccgtccta ggt                                  333
```

<210> SEQ ID NO 61
<211> LENGTH: 309
<212> TYPE: DNA
<213> ORGANISM: Homo sapiens

<400> SEQUENCE: 61

```
tcgtctgagc tgactcagga ccctgctgtg tctgtggcct tgggacagac agtcaggatc     60
acatgccaag gagacagcct cagaagctat tatgcaagct ggtaccagca gaagccagga   120
caggcccctg tacttgtcat ctctgctaaa aacaaccggc cctcagggat cccagaccga   180
ttctctggct ccagctcagg aaacacagct tccttgacca tcactggggc tcaggcggaa   240
gatgaagctg actattactg taactcccgg gacagcagta accatgtggt attcggcgga   300
gggaccaag                                                             309
```

<210> SEQ ID NO 62
<211> LENGTH: 333
<212> TYPE: DNA
<213> ORGANISM: Homo sapiens

<400> SEQUENCE: 62

```
cagtctgtgc tgactcagcc accctcagcg tctgggaccc ccgggcagag ggtcaccatc     60
tcttgttctg gaaggaactc caacatcgga agttatactg taacctggta ccagcagctc   120
ccaggaacgg cccccaaact cctcatctat agtaatagtc agcggccctc aggggtccct   180
gaccgattct caggctccaa gtctggcacc tcagcctcct tggccatcag tgggctccag   240
tctgaagatg aggctgatta ttactgtctc gtgtgggacg acgtcctgaa tggcccggtg   300
```

```
ttcggcggag ggaccaagct gaccgtccta ggt                                  333
```

<210> SEQ ID NO 63
<211> LENGTH: 324
<212> TYPE: DNA
<213> ORGANISM: Homo sapiens

<400> SEQUENCE: 63

```
tcgtctgagc tgactcagga ccctgctgtg tctgtggcct tgggacagac agtcaggatc      60
acatgccaag gagacagcct cagaagctat tatgcaagct ggtaccagca gaagccagga     120
caggcccctg tacttgtcat ctctgctaaa aacaaccggc cctcagggat cccagaccga     180
ttctctggct ccagctcagg aaacacagct tccttgacca tcactggggc tcaggcggaa     240
gatgaggctg actattactg tgcgtcccgg aacggctgga accatgtggt attcggcgga     300
gggaccaagc tgaccgtcct aggt                                           324
```

<210> SEQ ID NO 64
<211> LENGTH: 324
<212> TYPE: DNA
<213> ORGANISM: Homo sapiens

<400> SEQUENCE: 64

```
tcgtctgagc tgactcagga ccctgctgtg tctgtggcct tgggacagac agtcagggtc      60
acatgccaag gagacagcct cagaagctat tatgcaagct ggtaccagca gaagccagga     120
caggcccctg tacttgtcat ctctgctaaa aacaaccggc cctcagggat cccagaccga     180
ttctctggct ccagctcagg aaacacagct tccttgacca tcactggggc tcaggcggaa     240
gatgaggctg actattactg tgcgtcccgg aacggctgga accatgtggt attcggcgga     300
gggaccaagc tgaccgtcct aggt                                           324
```

<210> SEQ ID NO 65
<211> LENGTH: 324
<212> TYPE: DNA
<213> ORGANISM: Homo sapiens

<400> SEQUENCE: 65

```
tcgtctgagc tgactcagga ccctgctgtg tctgtggcct tgggacagac agtcaggatc      60
acatgccaag gagacagcct cagaagctat tatgcaagct ggtaccagca gaagccagga     120
caggcccctg tacttgtcat ctctgctaaa aacaaccggc cctcagggat cccagaccga     180
ttctctggct ccagctcagg aaacacagct tccttgacca tcactggggc tcaggcggaa     240
gatgaggctg actattactg tgcgtcccgg aacggctgga accatgtggt attcggcgga     300
gggaccaagc tgaccgtcct aggt                                           324
```

<210> SEQ ID NO 66
<211> LENGTH: 324
<212> TYPE: DNA
<213> ORGANISM: Homo sapiens

<400> SEQUENCE: 66

```
tcgtctgagc tgactcagga ccctgctgtg tctgtggcct tgggacagac agtcagggtc      60
acatgccaag gagacagcct cagaagctat tatgcaagct ggtaccagca gaagccagga     120
caggcccctg tacttgtcat ctctgctaaa aacaaccggc cctcagggat cccagaccga     180
ttctctggct ccagctcagg aaacacagct tccttgacca tcactggggc tcaggcggaa     240
gatgaggctg actattactg tgcgtcccgg aacggctgga accatgtggt attcggcgga     300
```

```
gggaccaagc tgaccgtcct aggt                                          324

<210> SEQ ID NO 67
<211> LENGTH: 324
<212> TYPE: DNA
<213> ORGANISM: Homo sapiens

<400> SEQUENCE: 67
tcgtctgagc tgactcagga ccctgctgtg tctgtggcct tgggacagac agtcaggatc    60
acatgccaag agacagcct cagaagctat tatgcaagct ggtaccagca gaagccagga   120
caggcccctg tacttgtcat ctctgctaaa acaaccggc cctcagggat cccagaccga   180
ttctctggct ccagctcagg aaacacagct tccttgacca tcactggggc tcaggcggaa   240
gatgaggctg actattactg tcgacccgg aacggctgga ccatgtggt attcggcgga   300 gggaccaagc tgaccgtcct aggt                                          324

<210> SEQ ID NO 68
<211> LENGTH: 324
<212> TYPE: DNA
<213> ORGANISM: Homo sapiens

<400> SEQUENCE: 68
tcgtctgagc tgactcagga ccctgctgtg tctgtggcct tgggacagac agtcagggtc    60
acatgccaag agacagcct cagaagctat tatgcaagct ggtaccagca gaagccagga   120
caggcccctg tacttgtcat ctctgctaaa acaaccggc cctcagggat cccagaccga   180
ttctctggct ccagctcagg aaacacagct tccttgacca tcactggggc tcaggcggaa   240
gatgaggctg actattactg tcgacccgg aacggctgga ccatgtggt attcggcgga   300 gggaccaagc tgaccgtcct aggt                                          324

<210> SEQ ID NO 69
<211> LENGTH: 541
<212> TYPE: PRT
<213> ORGANISM: Homo sapiens

<400> SEQUENCE: 69

Met Asn Cys Arg Glu Leu Pro Leu Thr Leu Trp Val Leu Ile Ser Val
1               5                   10                  15

Ser Thr Ala Glu Ser Cys Thr Ser Arg Pro His Ile Thr Val Val Glu
            20                  25                  30

Gly Glu Pro Phe Tyr Leu Lys His Cys Ser Cys Ser Leu Ala His Glu
        35                  40                  45

Ile Glu Thr Thr Thr Lys Ser Trp Tyr Lys Ser Gly Ser Gln Glu
    50                  55                  60

His Val Glu Leu Asn Pro Arg Ser Ser Arg Ile Ala Leu His Asp
65                  70                  75                  80

Cys Val Leu Glu Phe Trp Pro Val Glu Leu Asn Asp Thr Gly Ser Tyr
                85                  90                  95

Phe Phe Gln Met Lys Asn Tyr Thr Gln Lys Trp Lys Leu Asn Val Ile
            100                 105                 110

Arg Arg Asn Lys His Ser Cys Phe Thr Glu Arg Gln Val Thr Ser Lys
        115                 120                 125

Ile Val Glu Val Lys Lys Phe Phe Gln Ile Thr Cys Glu Asn Ser Tyr
    130                 135                 140

Tyr Gln Thr Leu Val Asn Ser Thr Ser Leu Tyr Lys Asn Cys Lys Lys
145                 150                 155                 160
```

Leu Leu Leu Glu Asn Asn Lys Asn Pro Thr Ile Lys Lys Asn Ala Glu
            165                 170                 175

Phe Glu Asp Gln Gly Tyr Tyr Ser Cys Val His Phe Leu His His Asn
        180                 185                 190

Gly Lys Leu Phe Asn Ile Thr Lys Thr Phe Asn Ile Thr Ile Val Glu
    195                 200                 205

Asp Arg Ser Asn Ile Val Pro Val Leu Leu Gly Pro Lys Leu Asn His
210                 215                 220

Val Ala Val Glu Leu Gly Lys Asn Val Arg Leu Asn Cys Ser Ala Leu
225                 230                 235                 240

Leu Asn Glu Glu Asp Val Ile Tyr Trp Met Phe Gly Glu Glu Asn Gly
            245                 250                 255

Ser Asp Pro Asn Ile His Glu Glu Lys Glu Met Arg Ile Met Thr Pro
            260                 265                 270

Glu Gly Lys Trp His Ala Ser Lys Val Leu Arg Ile Glu Asn Ile Gly
        275                 280                 285

Glu Ser Asn Leu Asn Val Leu Tyr Asn Cys Thr Val Ala Ser Thr Gly
    290                 295                 300

Gly Thr Asp Thr Lys Ser Phe Ile Leu Val Arg Lys Ala Asp Met Ala
305                 310                 315                 320

Asp Ile Pro Gly His Val Phe Thr Arg Gly Met Ile Ile Ala Val Leu
            325                 330                 335

Ile Leu Val Ala Val Val Cys Leu Val Thr Val Cys Val Ile Tyr Arg
            340                 345                 350

Val Asp Leu Val Leu Phe Tyr Arg His Leu Thr Arg Arg Asp Glu Thr
        355                 360                 365

Leu Thr Asp Gly Lys Thr Tyr Asp Ala Phe Val Ser Tyr Leu Lys Glu
    370                 375                 380

Cys Arg Pro Glu Asn Gly Glu Glu His Thr Phe Ala Val Glu Ile Leu
385                 390                 395                 400

Pro Arg Val Leu Glu Lys His Phe Gly Tyr Lys Leu Cys Ile Phe Glu
            405                 410                 415

Arg Asp Val Val Pro Gly Gly Ala Val Val Asp Glu Ile His Ser Leu
            420                 425                 430

Ile Glu Lys Ser Arg Arg Leu Ile Ile Val Leu Ser Lys Ser Tyr Met
        435                 440                 445

Ser Asn Glu Val Arg Tyr Glu Leu Glu Ser Gly Leu His Glu Ala Leu
    450                 455                 460

Val Glu Arg Lys Ile Lys Ile Ile Leu Ile Glu Phe Thr Pro Val Thr
465                 470                 475                 480

Asp Phe Thr Phe Leu Pro Gln Ser Leu Lys Leu Leu Lys Ser His Arg
            485                 490                 495

Val Leu Lys Trp Lys Ala Asp Lys Ser Leu Ser Tyr Asn Ser Arg Phe
        500                 505                 510

Trp Lys Asn Leu Leu Tyr Leu Met Pro Ala Lys Thr Val Lys Pro Gly
    515                 520                 525

Arg Asp Glu Pro Glu Val Leu Pro Val Leu Ser Glu Ser
530                 535                 540

<210> SEQ ID NO 70
<211> LENGTH: 1626
<212> TYPE: DNA
<213> ORGANISM: Homo sapiens

<400> SEQUENCE: 70

```
atgaattgta gagaattacc cttgacccct tgggtgctta tatctgtaag cactgcagaa      60
tcttgtactt cacgtcccca cattactgtg gttgaagggg aacctttcta tctgaaacat     120
tgctcgtgtt cacttgcaca tgagattgaa acaaccacca aaagctggta caaaagcagt     180
ggatcacagg aacatgtgga gctgaaccca aggagttcct cgagaattgc tttgcatgat     240
tgtgttttgg agttttggcc agttgagttg aatgacacag gatcttactt tttccaaatg     300
aaaaattata ctcagaaatg gaaattaaat gtcatcagaa gaaataaaca cagctgtttc     360
actgaaagac aagtaactag taaaattgtg gaagttaaaa aattttttca gataacctgt     420
gaaaacagtt actatcaaac actggtcaac agcacatcat tgtataagaa ctgtaaaaag     480
ctactactgg agaacaataa aacccaacg ataaagaaga cgccgagtt tgaagatcag       540
gggtattact cctgcgtgca tttccttcat cataatggaa aactatttaa tatcaccaaa     600
accttcaata taacaatagt ggaagatcgc agtaatatag ttccggttct tcttggacca     660
aagcttaacc atgttgcagt ggaattagga aaaaacgtaa ggctcaactg ctctgctttg     720
ctgaatgaag aggatgtaat ttattggatg ttcggggaag aaaatggatc ggatcctaat     780
atacatgaag agaaagaaat gagaattatg actccagaag gcaaatggca tgcttcaaaa     840
gtattgagaa ttgaaaatat tggtgaaagc aatctaaatg ttttatataa ttgcactgtg     900
gccagcacgg gaggcacaga caccaaaagc ttcatcttgg tgagaaaagc agacatggct     960
gatatcccag gccacgtctt cacaagagga atgatcatag ctgttttgat cttggtggca    1020
gtagtgtgcc tagtgactgt gtgtgtcatt tatagagttg acttggttct attttataga    1080
catttaacga gaagagatga acattaaca gatggaaaaa catatgatgc ttttgtgtct     1140
tacctaaaag aatgccgacc tgaaaatgga gaggagcaca cctttgctgt ggagattttg    1200
cccagggtgt tggagaaaca ttttgggtat aagttatgca tatttgaaag ggatgtagtg    1260
cctggaggag ctgttgttga tgaaatccac tcactgatga gaaaagccg aagactaatc    1320
attgtcctaa gtaaaagtta tatgtctaat gaggtcaggt atgaacttga aagtggactc    1380
catgaagcat tggtggaaag aaaaattaaa ataatcttaa ttgaatttac acctgttact    1440
gacttcacat tcttgcccca atcactaaag cttttgaaat ctcacagagt tctgaagtgg    1500
aaggccgata aatctctttc ttataactca aggttctgga gaaaccttct ttacttaatg    1560
cctgcaaaaa cagtcaagcc aggtagagac gaaccggaag tcttgcctgt tctttccgag    1620
tcttaa                                                                1626
```

<210> SEQ ID NO 71
<211> LENGTH: 599
<212> TYPE: PRT
<213> ORGANISM: Homo sapiens

<400> SEQUENCE: 71

Met Leu Cys Leu Gly Trp Ile Phe Leu Trp Leu Val Ala Gly Glu Arg
1               5                   10                  15

Ile Lys Gly Phe Asn Ile Ser Gly Cys Ser Thr Lys Lys Leu Leu Trp
            20                  25                  30

Thr Tyr Ser Thr Arg Ser Glu Glu Phe Val Leu Phe Cys Asp Leu
        35                  40                  45

Pro Glu Pro Gln Lys Ser His Phe Cys His Arg Asn Arg Leu Ser Pro
    50                  55                  60

Lys Gln Val Pro Glu His Leu Pro Phe Met Gly Ser Asn Asp Leu Ser
65                  70                  75                  80

-continued

Asp Val Gln Trp Tyr Gln Gln Pro Ser Asn Gly Asp Pro Leu Glu Asp
                85                  90                  95

Ile Arg Lys Ser Tyr Pro His Ile Ile Gln Asp Lys Cys Thr Leu His
            100                 105                 110

Phe Leu Thr Pro Gly Val Asn Asn Ser Gly Ser Tyr Ile Cys Arg Pro
        115                 120                 125

Lys Met Ile Lys Ser Pro Tyr Asp Val Ala Cys Cys Val Lys Met Ile
    130                 135                 140

Leu Glu Val Lys Pro Gln Thr Asn Ala Ser Cys Glu Tyr Ser Ala Ser
145                 150                 155                 160

His Lys Gln Asp Leu Leu Leu Gly Ser Thr Gly Ser Ile Ser Cys Pro
                165                 170                 175

Ser Leu Ser Cys Gln Ser Asp Ala Gln Ser Pro Ala Val Thr Trp Tyr
            180                 185                 190

Lys Asn Gly Lys Leu Leu Ser Val Glu Arg Ser Asn Arg Ile Val Val
        195                 200                 205

Asp Glu Val Tyr Asp Tyr His Gln Gly Thr Tyr Val Cys Asp Tyr Thr
    210                 215                 220

Gln Ser Asp Thr Val Ser Ser Trp Thr Val Arg Ala Val Val Gln Val
225                 230                 235                 240

Arg Thr Ile Val Gly Asp Thr Lys Leu Lys Pro Asp Ile Leu Asp Pro
                245                 250                 255

Val Glu Asp Thr Leu Glu Val Glu Leu Gly Lys Pro Leu Thr Ile Ser
            260                 265                 270

Cys Lys Ala Arg Phe Gly Phe Glu Arg Val Phe Asn Pro Val Ile Lys
        275                 280                 285

Trp Tyr Ile Lys Asp Ser Asp Leu Glu Trp Glu Val Ser Val Pro Glu
    290                 295                 300

Ala Lys Ser Ile Lys Ser Thr Leu Lys Asp Glu Ile Ile Glu Arg Asn
305                 310                 315                 320

Ile Ile Leu Glu Lys Val Thr Gln Arg Asp Leu Arg Arg Lys Phe Val
                325                 330                 335

Cys Phe Val Gln Asn Ser Ile Gly Asn Thr Thr Gln Ser Val Gln Leu
            340                 345                 350

Lys Glu Lys Arg Gly Val Val Leu Leu Tyr Ile Leu Leu Gly Thr Ile
        355                 360                 365

Gly Thr Leu Val Ala Val Leu Ala Ala Ser Ala Leu Leu Tyr Arg His
    370                 375                 380

Trp Ile Glu Ile Val Leu Leu Tyr Arg Thr Tyr Gln Ser Lys Asp Gln
385                 390                 395                 400

Thr Leu Gly Asp Lys Lys Asp Phe Asp Ala Phe Val Ser Tyr Ala Lys
                405                 410                 415

Trp Ser Ser Phe Pro Ser Glu Ala Thr Ser Ser Leu Ser Glu Glu His
            420                 425                 430

Leu Ala Leu Ser Leu Phe Pro Asp Val Leu Glu Asn Lys Tyr Gly Tyr
        435                 440                 445

Ser Leu Cys Leu Leu Glu Arg Asp Val Ala Pro Gly Gly Val Tyr Ala
    450                 455                 460

Glu Asp Ile Val Ser Ile Ile Lys Arg Ser Arg Arg Gly Ile Phe Ile
465                 470                 475                 480

Leu Ser Pro Asn Tyr Val Asn Gly Pro Ser Ile Phe Glu Leu Gln Ala
                485                 490                 495

Ala Val Asn Leu Ala Leu Asp Asp Gln Thr Leu Lys Leu Ile Leu Ile
            500                 505                 510

```
Lys Phe Cys Tyr Phe Gln Glu Pro Glu Ser Leu Pro His Leu Val Lys
        515                 520                 525

Lys Ala Leu Arg Val Leu Pro Thr Val Thr Trp Arg Gly Leu Lys Ser
    530                 535                 540

Val Pro Pro Asn Ser Arg Phe Trp Ala Lys Met Arg Tyr His Met Pro
545                 550                 555                 560

Val Lys Asn Ser Gln Gly Phe Thr Trp Asn Gln Leu Arg Ile Thr Ser
                565                 570                 575

Arg Ile Phe Gln Trp Lys Gly Leu Ser Arg Thr Glu Thr Thr Gly Arg
                580                 585                 590

Ser Ser Gln Pro Lys Glu Trp
        595

<210> SEQ ID NO 72
<211> LENGTH: 1800
<212> TYPE: DNA
<213> ORGANISM: Homo sapiens

<400> SEQUENCE: 72
atgctctgtt tgggctggat atttctttgg cttgttgcag gagagcgaat taaaggattt      60
aatatttcag gttgttccac aaaaaaactc ctttggacat attctacaag gagtgaagag     120
gaatttgtct tattttgtga tttaccagag ccacagaaat cacatttctg ccacagaaat     180
cgactctcac caaaacaagt ccctgagcac ctgcccttca tgggtagtaa cgacctatct     240
gatgtccaat ggtaccaaca accttcgaat ggagatccat tagaggacat taggaaaagc     300
tatcctcaca tcattcagga caaatgtacc cttcactttt tgaccccagg ggtgaataat     360
tctgggtcat atatttgtag acccaagatg attaagagcc cctatgatgt agcctgttgt     420
gtcaagatga ttttagaagt taagccccag acaaatgcat cctgtgagta ttccgcatca     480
cataagcaag acctacttct tgggagcact ggctctattt cttgccccag tctcagctgc     540
caaagtgatg cacaaagtcc agcggtaacc tggtacaaga atggaaaact cctctctgtg     600
gaaaggagca accgaatcgt agtggatgaa gtttatgact atcaccaggg cacatatgta     660
tgtgattaca ctcagtcgga tactgtgagt tcgtggacag tcagagctgt tgttcaagtg     720
agaaccattg tgggagacac taaactcaaa ccagatattc tggatcctgt cgaggacaca     780
ctggaagtag aacttggaaa gccttttaact attagctgca agcacgatt tggctttgaa     840 agggtctttta accctgtcat aaaatggtac atcaaagatt ctgacctaga gtgggaagtc     900
tcagtacctg aggcgaaaag tattaaatcc actttaaagg atgaaatcat tgagcgtaat     960
atcatcttgg aaaagtcac tcagcgtgat cttcgcagga gtttgtttg ctttgtccag    1020 aactccattg gaaacacaac ccagtccgtc caactgaaag aaaagagagg agtggtgctc    1080
ctgtacatcc tgcttggcac catcgggacc ctggtggccg tgctggcggc gagtgccctc    1140
ctctacaggc actggattga aatagtgctg ctgtaccgga cctaccagag caaggatcag    1200
acgcttgggg ataaaaagga ttttgatgct ttcgtatcct atgcaaaatg gagctctttt    1260
ccaagtgagg ccacttcatc tctgagtgaa gaacacttgg ccctgagcct atttcctgat    1320
gttttagaaa acaaatatgg atatagcctg tgtttgcttg aaagagatgt ggctccagga    1380
ggagtgtatg cagaagacat tgtgagcatt attaagagaa gcagagagg aatatttatc    1440 ttgagcccca actatgtcaa tggacccagt atctttgaac tacaagcagc agtgaatctt    1500
gccttggatg atcaaacact gaaactcatt ttaattaagt tctgttactt ccaagagcca    1560
gagtctctac ctcatctcgt gaaaaaagct ctcagggttt tgcccacagt tacttggaga    1620
```

-continued

```
ggcttaaaat cagttcctcc caattctagg ttctgggcca aaatgcgcta ccacatgcct    1680
gtgaaaaact ctcagggatt cacgtggaac cagctcagaa ttacctctag gattttcag     1740 tggaaaggac tcagtagaac agaaaccact gggaggagct cccagcctaa ggaatggtga    1800
```

<210> SEQ ID NO 73
<211> LENGTH: 467
<212> TYPE: PRT
<213> ORGANISM: Homo sapiens

<400> SEQUENCE: 73

```
Met Gly Ser Thr Ala Ile Leu Gly Leu Leu Ala Val Leu Gln Gly
1               5                   10                  15

Gly Arg Ala Glu Val Gln Leu Val Glu Ser Gly Gly Val Val Gln
            20                  25                  30

Pro Gly Arg Ser Leu Arg Leu Ser Cys Ala Ala Ser Gly Phe Thr Phe
            35                  40                  45

Ser Gly Tyr Gly Met His Trp Val Arg Gln Ala Pro Gly Lys Gly Leu
    50                  55                  60

Glu Trp Val Ala Val Ile Ser Asn Asp Gly Ser Lys Lys Tyr Tyr Ser
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Gly Ser Ser Ile Trp Leu Thr Ser Ala Leu
            115                 120                 125

Asn Leu Trp Gly Gln Gly Thr Thr Val Thr Val Ser Ser Ala Ser Thr
130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Asn Phe Gly Thr Gln Thr Tyr Thr Cys
        210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Gln Phe Asn Trp Tyr Val Asp Gly Val Glu Val
        290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350
```

```
Glu Lys Thr Ile Ser Lys Thr Lys Gly Gln Pro Arg Glu Pro Gln Val
            355                 360                 365
Tyr Thr Leu Pro Pro Ser Arg Glu Glu Met Thr Lys Asn Gln Val Ser
        370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Met Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly Lys
465

<210> SEQ ID NO 74
<211> LENGTH: 1427
<212> TYPE: DNA
<213> ORGANISM: Homo sapiens

<400> SEQUENCE: 74
gtcgacgccg ccaccatggg gtcaaccgcc atccttggcc tcctcctggc tgtcctgcag     60
ggagggcgcg ccgaggtgca gctggtggag tctgggggag gcgtggtcca gcctggggag    120
tccctgagac tctcctgtgc agcgtctgga ttcaccttca gcggttatgg catgcactgg    180
gtccgccagg ctccaggcaa ggggctggag tgggtggcag taatatcaaa tgatggaagt    240
aagaaatatt attcagactc cgtgaagggc cgattcacca tctccagaga caattccaaa    300
aacacgctgt atctgcagat gaacagcctg agagctgagg acacggctgt atattactgt    360
gcgaaagggt ccagttccat atggctgacc tcggccctga acctgtgggg cagggggacc    420
acggtcaccg tctcctcagc tagcaccaag ggcccatcgg tcttccccct ggcgccctgc    480
tccaggagca cctccgagag cacagcggcc ctgggctgcc tggtcaagga ctacttcccc    540
gaaccggtga cggtgtcgtg gaactcaggc gctctgacca gcggcgtgca caccttccca    600
gctgtcctac agtcctcagg actctactcc ctcagcagcg tggtgaccgt gccctccagc    660
aacttcggca cccagaccta cacctgcaac gtagatcaca agcccagcaa caccaaggtg    720
gacaagacag ttgagcgcaa atgttgtgtc gagtgcccac cgtgcccagc accacctgtg    780
gcaggaccgt cagtcttcct cttccccca aaacccaagg acaccctcat gatctcccgg    840
acccctgagg tcacgtgcgt ggtggtggac gtgagccacg aagaccccga ggtccagttc    900
aactggtacg tggacggcgt ggaggtgcat aatgccaaga caaagccacg ggaggagcag    960
ttcaacagca cgttccgtgt ggtcagcgtc ctcaccgttg tgcaccagga ctggctgaac   1020
ggcaaggagt acaagtgcaa ggtctccaac aaaggcctcc cagcccccat cgagaaaacc   1080
atctccaaaa ccaaagggca gccccgagaa ccacaggtgt acaccctgcc cccatcccgg   1140
gaggagatga ccaagaacca ggtcagcctg acctgcctgg tcaaaggctt ctaccccagc   1200
gacatcgccg tggagtggga gagcaatggg cagccggaga caactacaa gaccacacct   1260 cccatgctgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaga agagcctctc cctgtctccg ggtaaatgag cggccgc                 1427
```

<210> SEQ ID NO 75
<211> LENGTH: 233
<212> TYPE: PRT
<213> ORGANISM: Homo sapiens

<400> SEQUENCE: 75

Met Glu Thr Asp Thr Leu Leu Leu Trp Val Leu Leu Leu Trp Val Pro
1               5                   10                  15

Gly Ser Thr Gly Ser Ser Glu Leu Thr Gln Asp Pro Ala Val Ser Val
            20                  25                  30

Ala Leu Gly Gln Thr Val Arg Ile Thr Cys Gln Gly Asp Ser Leu Arg
        35                  40                  45

Ser Tyr Tyr Ala Ser Trp Tyr Gln Gln Lys Pro Gly Gln Ala Pro Val
    50                  55                  60

Leu Val Ile Ser Ala Lys Asn Arg Pro Ser Gly Ile Pro Asp Arg
65                  70                  75                  80

Phe Ser Gly Ser Ser Gly Asn Thr Ala Ser Leu Thr Ile Thr Gly
                85                  90                  95

Ala Gln Ala Glu Asp Glu Ala Asp Tyr Tyr Cys Ala Ser Arg Asn Gly
            100                 105                 110

Trp Asn His Val Val Phe Gly Gly Gly Thr Lys Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230

<210> SEQ ID NO 76
<211> LENGTH: 733
<212> TYPE: DNA
<213> ORGANISM: Homo sapiens

<400> SEQUENCE: 76
gtcgacgttt aaacgccgcc accatggaga cagacacact cctgctatgg gtactgctgc     60
tctgggttcc aggttccact ggttcgtctg agctgactca ggaccctgct gtgtctgtgg    120
ccttgggaca gacagtcagg atcacatgcc aaggagacag cctcagaagc tattatgcaa    180
gctggtacca gcagaagcca ggacaggccc ctgtacttgt catctctgct aaaaacaacc    240
ggccctcagg gatcccagac cgattctctg gctccagctc aggaaacaca gcttccttga    300
ccatcactgg ggctcaggcg gaagatgagg ctgactatta ctgtgcgtcc cggaacggct    360
ggaaccatgt ggtattcggc ggagggacca agctgaccgt cctaggccaa ccgaaagcgg    420
cgcccctcgg tcactctgtt cccgccctcct ctgaggagct tcaagccaac aaggccacac    480
tggtgtgtct cataagtgac ttctacccgg gagccgtgac agtggcctgg aaggcagata    540

-continued

```
gcagccccgt caaggcggga gtggagacca ccacaccctc caaacaaagc aacaacaagt      600
acgcggccag cagctatctg agcctgacgc ctgagcagtg gaagtcccac agaagctaca      660
gctgccaggt cacgcatgaa gggagcaccg tggagaagac agtggcccct acagaatgtt      720
cataggcggc cgc                                                         733

<210> SEQ ID NO 77
<211> LENGTH: 467
<212> TYPE: PRT
<213> ORGANISM: Homo sapiens

<400> SEQUENCE: 77

Met Gly Ser Thr Ala Ile Leu Gly Leu Leu Ala Val Leu Gln Gly
1               5                   10                  15

Gly Arg Ala Glu Val Gln Leu Val Glu Ser Gly Gly Val Val Gln
                20                  25                  30

Pro Gly Arg Ser Leu Arg Leu Ser Cys Ala Ala Ser Gly Phe Thr Phe
                35                  40                  45

Ser Gly Tyr Gly Met His Trp Val Arg Gln Ala Pro Gly Lys Gly Leu
            50                  55                  60

Glu Trp Val Ala Val Ile Ser Asn Asp Gly Ser Lys Lys Tyr Tyr Ser
65              70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
                100                 105                 110

Tyr Tyr Cys Ala Lys Gly Ser Ser Ile Trp Leu Ser Gln Ser Leu
                115                 120                 125

Asp Gly Trp Gly Gln Gly Thr Thr Val Thr Val Ser Ser Ala Ser Thr
            130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
                180                 185                 190

Thr Phe Pro Ala Val Leu Gln Ser Ser Gly Leu Tyr Ser Leu Ser Ser
            195                 200                 205

Val Val Thr Val Pro Ser Ser Asn Phe Gly Thr Gln Thr Tyr Thr Cys
        210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
```

```
                  340             345             350
Glu Lys Thr Ile Ser Lys Thr Lys Gly Gln Pro Arg Glu Pro Gln Val
            355                 360                 365

Tyr Thr Leu Pro Pro Ser Arg Glu Glu Met Thr Lys Asn Gln Val Ser
        370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
            450                 455                 460

Pro Gly Lys
465

<210> SEQ ID NO 78
<211> LENGTH: 1404
<212> TYPE: DNA
<213> ORGANISM: Homo sapiens

<400> SEQUENCE: 78
atggggtcaa ccgccatcct tggcctcctc ctggctgtcc tgcagggagg gcgcgccgag     60
gtgcagctgg tggagtctgg gggaggcgtg gtccagcctg gaggtccct  gagactctcc    120 tgtgcagcgt ctggattcac cttcagcggt tatggcatgc actgggtccg ccaggctcca    180 ggcaagggc  tggagtgggt ggcagtaata tcaaatgatg gaagtaagaa atattattca    240
gactccgtga agggccgatt caccatctcc agagacaatt ccaaaaacac gctgtatctg    300
cagatgaaca gcctgagagc tgaggacacg gctgtatatt actgtgcgaa aggtccagt    360 tccatatggc tgtcgcagtc cctggacggc tggggcagg  gaccacggt  caccgtctcc    420 tcagctagca ccaagggccc atcggtcttc cccctggcgc cctgctccag gagcacctcc    480
gagagcacag cggccctggg ctgcctggtc aaggactact tccccgaacc ggtgacggtg    540
tcgtggaact caggcgctct gaccagcggc gtgcacacct tcccagctgt cctacagtcc    600
tcaggactct actccctcag cagcgtggtg accgtgccct ccagcaactt cggcacccag    660
acctacacct gcaacgtaga tcacaagccc agcaacacca aggtggacaa gacagttgag    720
cgcaaatgtt gtgtcgagtg cccaccgtgc ccagcaccac ctgtggcagg accgtcagtc    780
ttcctcttcc ccccaaaacc caaggacacc ctcatgatct cccggacccc tgaggtcacg    840
tgcgtggtgg tggacgtgag ccacgaagac cccgaggtcc agttcaactg gtacgtggac    900
ggcgtggagg tgcataatgc caagacaaag ccacgggagg agcagttcaa cagcacgttc    960
cgtgtggtca gcgtcctcac cgttgtgcac caggactggc tgaacggcaa ggagtacaag   1020
tgcaaggtct ccaacaaagg cctcccagcc cccatcgaga aaaccatctc caaaaccaaa   1080
gggcagcccc gagaaccaca ggtgtacacc ctgcccccat cccgggagga gatgaccaag   1140
aaccaggtca gcctgacctg cctggtcaaa ggcttctacc ccagcgacat cgccgtggag   1200
tgggagagca atgggcagcc ggagaacaac tacaagacca cacctcccat gctggactcc   1260
gacggctcct tcttcctcta cagcaagctc accgtggaca gagcaggtg  gcagcagggg   1320 aacgtcttct catgctccgt gatgcatgag gctctgcaca accactacac gcagaagagc   1380
```
ctctccctgt ctccgggtaa atga                                            1404

<210> SEQ ID NO 79
<211> LENGTH: 233
<212> TYPE: PRT
<213> ORGANISM: Homo sapiens

<400> SEQUENCE: 79

```
Met Glu Thr Asp Thr Leu Leu Leu Trp Val Leu Leu Leu Trp Val Pro
1               5                   10                  15

Gly Ser Thr Gly Ser Ser Glu Leu Thr Gln Asp Pro Ala Val Ser Val
            20                  25                  30

Ala Leu Gly Gln Thr Val Arg Ile Thr Cys Gln Gly Asp Ser Leu Arg
        35                  40                  45

Ser Tyr Tyr Ala Ser Trp Tyr Gln Gln Lys Pro Gly Gln Ala Pro Val
    50                  55                  60

Leu Val Ile Ser Ala Lys Asn Asn Arg Pro Ser Gly Ile Pro Asp Arg
65                  70                  75                  80

Phe Ser Gly Ser Ser Ser Gly Asn Thr Ala Ser Leu Thr Ile Thr Gly
                85                  90                  95

Ala Gln Ala Glu Asp Glu Ala Asp Tyr Tyr Cys Ala Ser Arg Asn Gly
            100                 105                 110

Trp Asn His Val Val Phe Gly Gly Gly Thr Lys Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230
```

<210> SEQ ID NO 80
<211> LENGTH: 710
<212> TYPE: DNA
<213> ORGANISM: Homo sapiens

<400> SEQUENCE: 80
atggagacag acacactcct gctatgggta ctgctgctct ggttccagg ttccactggt        60 tcgtctgagc tgactcagga ccctgctgtg tctgtggcct tgggacagac agtcaggatc      120
acatgccaag agacagcct cagaagctat tatgcaagct ggtaccagca gaagccagga      180
caggcccctg tacttgtcat ctctgctaaa acaaccggc cctcagggat cccagaccga      240
ttctctggct ccagctcagg aaacacagct tccttgacca tcactggggc tcaggcggaa      300
gatgaggctg actattactg tgcgtccgg aacggctgga accatgtggt attcggcgga      360
gggaccaagc tgaccgtcct aggccaaccg aaagcggcgc cctcggtcac tctgttcccg      420
ccctcctctg aggagcttca agccaacaag gccacactgg tgtgtctcat aagtgacttc      480
tacccgggag ccgtgacagt ggcctggaag gcagatagca gccccgtcaa ggcgggagtg      540
gagaccacca caccctccaa acaaagcaac aacaagtacg cggccagcag ctatctgagc 600
ctgacgcctg agcagtggaa gtcccacaga agctacagct gccaggtcac gcatgaaggg 660
agcaccgtgg agaagacagt ggcccctaca gaatgttcat aggcggccgc 710

<210> SEQ ID NO 81
<211> LENGTH: 466
<212> TYPE: PRT
<213> ORGANISM: Homo sapiens

<400> SEQUENCE: 81

```
Met Gly Ser Thr Ala Ile Leu Gly Leu Leu Ala Val Leu Gln Gly
1               5                   10                  15

Gly Arg Ala Gln Val Gln Leu Val Gln Ser Gly Ala Glu Val Lys Lys
            20                  25                  30

Pro Gly Ala Ser Val Lys Val Ser Cys Lys Val Ser Gly Tyr Thr Leu
        35                  40                  45

Thr Glu Leu Ser Met His Trp Val Arg Gln Ala Pro Gly Lys Gly Leu
    50                  55                  60

Glu Trp Met Gly Gly Phe Asp Arg Glu Asp Glu Thr Ile His Ala
65                  70                  75                  80

Gln Lys Phe Gln Gly Arg Val Thr Met Thr Glu Asp Thr Ser Thr Asp
                85                  90                  95

Thr Ala Tyr Met Glu Leu Ser Ser Leu Arg Ser Glu Asp Thr Ala Val
            100                 105                 110

Tyr Tyr Cys Ala Thr Asp Leu Met Val Trp Gly Asp Phe Trp Ile Gln
        115                 120                 125

His Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350
```

| | | | | | | | | | | | |
|---|---|---|---|---|---|---|---|---|---|---|---|
|Lys|Thr|Ile|Ser|Lys|Thr|Lys|Gly|Gln|Pro|Arg|Glu Pro Gln Val Tyr|
| | |355| | | |360| | | |365| |

Thr Leu Pro Pro Ser Arg Glu Glu Met Thr Lys Asn Gln Val Ser Leu
        370             375             380

Thr Cys Leu Val Lys Gly Phe Tyr Pro Ser Asp Ile Ala Val Glu Trp
385             390             395                 400

Glu Ser Asn Gly Gln Pro Glu Asn Asn Tyr Lys Thr Thr Pro Pro Met
            405             410             415

Leu Asp Ser Asp Gly Ser Phe Phe Leu Tyr Ser Lys Leu Thr Val Asp
            420             425             430

Lys Ser Arg Trp Gln Gln Gly Asn Val Phe Ser Cys Ser Val Met His
            435             440             445

Glu Ala Leu His Asn His Tyr Thr Gln Lys Ser Leu Ser Leu Ser Pro
    450             455             460

Gly Lys
465

<210> SEQ ID NO 82
<211> LENGTH: 1401
<212> TYPE: DNA
<213> ORGANISM: Homo sapiens

<400> SEQUENCE: 82

```
atgggtcaa ccgccatcct tggcctcctc ctggctgtcc tgcagggagg gcgcgcccag      60
gtgcagctgg tgcagtctgg ggctgaggtg aagaagcctg ggcctcagt gaaggtctcc     120
tgcaaggttt ccggatacac cctcactgaa ttatccatgc actgggtgcg acaggctcct    180
ggaaaagggc ttgagtggat gggaggtttt gatcgtgaag atgatgaaac aatccacgca    240
cagaagttcc agggcagagt caccatgacc gaggacacat ctacagacac agcctacatg    300
gaactgagca gcctgcgatc tgaggacacg gccgtttatt actgtgcaac agatcttatg    360
gtgtggggcg attttggat ccagcactgg ggccagggga cactggtcac cgtctcctca    420
gctagcacca agggcccatc ggtcttcccc ctggcgccct gctccaggag cacctccgag    480
agcacagcgg ccctgggctg cctggtcaag gactacttcc ccgaaccggt gacggtgtcg    540
tggaactcag gcgctctgac cagcggcgtg cacaccttcc cagctgtcct acagtcctca    600
ggactctact ccctcagcag cgtggtgacc gtgccctcca gcaacttcgg cacccagacc    660
tacacctgca acgtagatca caagcccagc aacaccaagg tggacaagac agttgagcgc    720
aaatgttgtg tcgagtgccc accgtgccca gcaccacctg tggcaggacc gtcagtcttc    780
ctcttcccc caaaacccaa ggacaccctc atgatctccc ggacccctga ggtcacgtgc    840
gtggtggtgg acgtgagcca cgaagacccc gaggtccagt tcaactggta cgtggacggc    900
gtggaggtgc ataatgccaa gacaaagcca cgggaggagc agttcaacag cacgttccgt    960
gtggtcagcg tcctcaccgt tgtgcaccag gactggctga acggcaagga gtacaagtgc   1020
aaggtctcca acaaaggcct cccagccccc atcgagaaaa ccatctccaa aaccaaaggg   1080
cagccccgag aaccacaggt gtacaccctg cccccatccc gggaggagat gaccaagaac   1140
caggtcagcc tgacctgcct ggtcaaaggc ttctacccca gcgacatcgc cgtggagtgg   1200
gagagcaatg ggcagccgga gaacaactac aagaccacac tcccatgct ggactccgac   1260
ggctcctct tcctctacag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaatg a                                             1401
```

<210> SEQ ID NO 83
<211> LENGTH: 238
<212> TYPE: PRT
<213> ORGANISM: Homo sapiens

<400> SEQUENCE: 83

```
Met Glu Thr Asp Thr Leu Leu Leu Trp Val Leu Leu Trp Val Pro
1               5                   10                  15

Gly Ser Thr Gly Ala Ser Gln Ser Val Leu Thr Gln Pro Pro Ser Ala
                20                  25                  30

Ser Gly Thr Pro Gly Gln Arg Val Thr Ile Ser Cys Ser Gly Arg Asn
            35                  40                  45

Ser Asn Ile Gly Ser Tyr Thr Val Thr Trp Tyr Gln Gln Leu Pro Gly
        50                  55                  60

Thr Ala Pro Lys Leu Leu Ile Tyr Ser Asn Ser Gln Arg Pro Ser Gly
65                  70                  75                  80

Val Pro Asp Arg Phe Ser Gly Ser Lys Ser Gly Thr Ser Ala Ser Leu
                85                  90                  95

Ala Ile Ser Gly Leu Gln Ser Glu Asp Glu Ala Asp Tyr Tyr Cys Val
                100                 105                 110

Val Trp Asp Glu Ile Leu Asn Gly Pro Val Phe Gly Gly Gly Thr Lys
                115                 120                 125

Leu Thr Val Leu Gly Gln Pro Lys Ala Ala Pro Ser Val Thr Leu Phe
130                 135                 140

Pro Pro Ser Ser Glu Glu Leu Gln Ala Asn Lys Ala Thr Leu Val Cys
145                 150                 155                 160

Leu Ile Ser Asp Phe Tyr Pro Gly Ala Val Thr Val Ala Trp Lys Ala
                165                 170                 175

Asp Ser Ser Pro Val Lys Ala Gly Val Glu Thr Thr Thr Pro Ser Lys
                180                 185                 190

Gln Ser Asn Asn Lys Tyr Ala Ala Ser Ser Tyr Leu Ser Leu Thr Pro
            195                 200                 205

Glu Gln Trp Lys Ser His Arg Ser Tyr Ser Cys Gln Val Thr His Glu
        210                 215                 220

Gly Ser Thr Val Glu Lys Thr Val Ala Pro Thr Glu Cys Ser
225                 230                 235
```

<210> SEQ ID NO 84
<211> LENGTH: 717
<212> TYPE: DNA
<213> ORGANISM: Homo sapiens

<400> SEQUENCE: 84

```
atggagacag acacactcct gctatgggta ctgctgctct gggttccagg ttccactggt    60
gctagccagt ctgtgctgac tcagccaccc tcagcgtctg gaccccccgg cagagggtc   120
accatctctt gttctggaag gaactccaac atcggaagtt atactgtaac ctggtaccag   180
cagctcccag gaacggcccc caaactcctc atctatagta atagtcagcg gccctcaggg   240
gtccctgacc gattctcagg ctccaagtct ggcacctcag cctccttggc catcagtggg   300
ctccagtctg aagatgaggc tgattattac tgtgtggtgt gggacgagat cctgaatggc   360
ccggtgttcg gcggagggac caagctgacc gtcctaggcc aaccgaaagc ggcgccctcg   420
gtcactctgt tcccgccctc ctctgaggag cttcaagcca acaaggccac actggtgtgt   480
ctcataagtg acttctaccc gggagccgtg acagtggcct ggaaggcaga tagcagcccc   540
```

```
gtcaaggcgg gagtggagac caccacaccc tccaaacaaa gcaacaacaa gtacgcggcc    600
agcagctatc tgagcctgac gcctgagcag tggaagtccc acagaagcta cagctgccag    660
gtcacgcatg aagggagcac cgtggagaag acagtggccc ctacagaatg ttcatag       717
```

<210> SEQ ID NO 85
<211> LENGTH: 466
<212> TYPE: PRT
<213> ORGANISM: Homo sapiens

<400> SEQUENCE: 85

```
Met Gly Ser Thr Ala Ile Leu Gly Leu Leu Ala Val Leu Gln Gly
1               5                   10                  15

Gly Arg Ala Gln Val Gln Leu Val Gln Ser Gly Ala Glu Val Lys Lys
            20                  25                  30

Pro Gly Ala Ser Val Lys Val Ser Cys Lys Val Ser Gly Tyr Thr Leu
        35                  40                  45

Thr Glu Leu Ser Met His Trp Val Arg Gln Ala Pro Gly Lys Gly Leu
    50                  55                  60

Glu Trp Met Gly Gly Phe Asp Arg Glu Asp Asp Glu Thr Ile His Ala
65                  70                  75                  80

Gln Lys Phe Gln Gly Arg Val Thr Met Thr Glu Asp Thr Ser Thr Asp
                85                  90                  95

Thr Ala Tyr Met Glu Leu Ser Ser Leu Arg Ser Glu Asp Thr Ala Val
            100                 105                 110

Tyr Tyr Cys Ala Thr Asp Leu Met Val Trp Asn Phe Pro Pro Ile Gln
        115                 120                 125

His Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350
```

-continued

```
Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465
```

```
<210> SEQ ID NO 86
<211> LENGTH: 1401
<212> TYPE: DNA
<213> ORGANISM: Homo sapiens

<400> SEQUENCE: 86
```

| | | | | | |
|---|---|---|---|---|---|
| atgggtcaa | ccgccatcct | tggcctcctc | ctggctgtcc | tgcagggagg | gcgcgcccag | 60 |
| gtgcagctgg | tgcagtctgg | ggctgaggtg | aagaagcctg | ggcctcagt | gaaggtctcc | 120 |
| tgcaaggttt | ccggatacac | cctcactgaa | ttatccatgc | actgggtgcg | acaggctcct | 180 |
| ggaaaagggc | ttgagtggat | gggaggtttt | gatcgtgaag | atgatgaaac | aatccacgca | 240 |
| cagaagttcc | agggcagagt | caccatgacc | gaggacacat | ctacagacac | agcctacatg | 300 |
| gaactgagca | gcctgcgatc | tgaggacacg | gccgtttatt | actgtgcaac | agatcttatg | 360 |
| gtgtggaact | tccccccat | ccagcactgg | ggccagggga | cactggtcac | cgtctcctca | 420 |
| gctagcacca | agggcccatc | ggtcttcccc | ctggcgccct | gctccaggag | cacctccgag | 480 |
| agcacagcgg | ccctgggctg | cctggtcaag | gactacttcc | ccgaaccggt | gacggtgtcg | 540 |
| tggaactcag | gcgctctgac | cagcggcgtg | cacaccttcc | cagctgtcct | acagtcctca | 600 |
| ggactctact | ccctcagcag | cgtggtgacc | gtgccctcca | gcaacttcgg | cacccagacc | 660 |
| tacacctgca | acgtagatca | caagcccagc | aacaccaagg | tggacaagac | agttgagcgc | 720 |
| aaatgttgtg | tcgagtgccc | accgtgccca | gcaccacctg | tggcaggacc | gtcagtcttc | 780 |
| ctcttccccc | caaaacccaa | ggacaccctc | atgatctccc | ggaccctga | ggtcacgtgc | 840 |
| gtggtggtgg | acgtgagcca | cgaagacccc | gaggtccagt | tcaactggta | cgtggacggc | 900 |
| gtggaggtgc | ataatgccaa | gacaaagcca | cgggaggagc | agttcaacag | cacgttccgt | 960 |
| gtggtcagcg | tcctcaccgt | tgtgcaccag | gactggctga | acggcaagga | gtacaagtgc | 1020 |
| aaggtctcca | acaaaggcct | cccagccccc | atcgagaaaa | ccatctccaa | aaccaaaggg | 1080 |
| cagccccgag | aaccacaggt | gtacaccctg | cccccatccc | gggaggagat | gaccaagaac | 1140 |
| caggtcagcc | tgacctgcct | ggtcaaaggc | ttctacccca | gcgacatcgc | cgtggagtgg | 1200 |
| gagagcaatg | ggcagccgga | gaacaactac | aagaccacac | ctcccatgct | ggactccgac | 1260 |
| ggctccttct | tcctctacag | caagctcacc | gtggacaaga | gcaggtggca | gcaggggaac | 1320 |
| gtcttctcat | gctccgtgat | gcatgaggct | ctgcacaacc | actacacgca | gaagagcctc | 1380 |
| tccctgtctc | cgggtaaatg | a | | | | 1401 |

<210> SEQ ID NO 87
<211> LENGTH: 238
<212> TYPE: PRT
<213> ORGANISM: Homo sapiens

<400> SEQUENCE: 87

Met Glu Thr Asp Thr Leu Leu Leu Trp Val Leu Leu Leu Trp Val Pro
1               5                   10                  15

Gly Ser Thr Gly Ala Ser Gln Ser Val Leu Thr Gln Pro Pro Ser Ala
            20                  25                  30

Ser Gly Thr Pro Gly Gln Arg Val Thr Ile Ser Cys Ser Gly Arg Asn
        35                  40                  45

Ser Asn Ile Gly Ser Tyr Thr Val Thr Trp Tyr Gln Gln Leu Pro Gly
    50                  55                  60

Thr Ala Pro Lys Leu Leu Ile Tyr Ser Asn Ser Gln Arg Pro Ser Gly
65                  70                  75                  80

Val Pro Asp Arg Phe Ser Gly Ser Lys Ser Gly Thr Ser Ala Ser Leu
                85                  90                  95

Ala Ile Ser Gly Leu Gln Ser Glu Asp Glu Ala Asp Tyr Tyr Cys Val
            100                 105                 110

Val Trp Asp Asp Val Leu Asn Gly Pro Val Phe Gly Gly Gly Thr Lys
        115                 120                 125

Leu Thr Val Leu Gly Gln Pro Lys Ala Ala Pro Ser Val Thr Leu Phe
    130                 135                 140

Pro Pro Ser Ser Glu Glu Leu Gln Ala Asn Lys Ala Thr Leu Val Cys
145                 150                 155                 160

Leu Ile Ser Asp Phe Tyr Pro Gly Ala Val Thr Val Ala Trp Lys Ala
                165                 170                 175

Asp Ser Ser Pro Val Lys Ala Gly Val Glu Thr Thr Thr Pro Ser Lys
            180                 185                 190

Gln Ser Asn Asn Lys Tyr Ala Ala Ser Ser Tyr Leu Ser Leu Thr Pro
        195                 200                 205

Glu Gln Trp Lys Ser His Arg Ser Tyr Ser Cys Gln Val Thr His Glu
    210                 215                 220

Gly Ser Thr Val Glu Lys Thr Val Ala Pro Thr Glu Cys Ser
225                 230                 235

<210> SEQ ID NO 88
<211> LENGTH: 717
<212> TYPE: DNA
<213> ORGANISM: Homo sapiens

<400> SEQUENCE: 88
atggagacag acacactcct gctatgggta ctgctgctct gggttccagg ttccactggt      60
gctagccagt ctgtgctgac tcagccaccc tcagcgtctg gaccccccgg cagagggtc     120 accatctctt gttctggaag gaactccaac atcggaagtt atactgtaac ctggtaccag    180
cagctcccag gaacggcccc caaactcctc atctatagta atagtcagcg gccctcaggg    240
gtccctgacc gattctcagg ctccaagtct ggcacctcag cctccttggc catcagtggg    300
ctccagtctg aagatgaggc tgattattac tgtgtggtgt gggatgacgt gctgaatggc    360
ccggtgttcg gcggagggac caagctgacc gtcctaggcc aaccgaaagc ggcgccctcg    420
gtcactctgt tcccgccctc ctctgaggag cttcaagcca acaaggccac actggtgtgt    480
ctcataagtg acttctaccc gggagccgtg acagtggcct ggaaggcaga tagcagcccc    540
gtcaaggcgg gagtggagac caccacaccc tccaaacaaa gcaacaacaa gtacgcggcc    600

```
agcagctatc tgagcctgac gcctgagcag tggaagtccc acagaagcta cagctgccag    660
gtcacgcatg aagggagcac cgtggagaag acagtggccc ctacagaatg ttcatag       717
```

<210> SEQ ID NO 89
<211> LENGTH: 5
<212> TYPE: PRT
<213> ORGANISM: Homo sapiens

<400> SEQUENCE: 89

Gly Tyr Gly Met His
1               5

<210> SEQ ID NO 90
<211> LENGTH: 18
<212> TYPE: PRT
<213> ORGANISM: Homo sapiens

<400> SEQUENCE: 90

Val Ile Ser Asn Asp Gly Ser Lys Lys Tyr Tyr Ser Asp Ser Val Lys
1               5                   10                  15

Gly Arg

<210> SEQ ID NO 91
<211> LENGTH: 12
<212> TYPE: PRT
<213> ORGANISM: Homo sapiens

<400> SEQUENCE: 91

Ser Ser Ser Ile Trp Leu Thr Gln Ser Leu Asp His
1               5                   10

<210> SEQ ID NO 92
<211> LENGTH: 5
<212> TYPE: PRT
<213> ORGANISM: Homo sapiens

<400> SEQUENCE: 92

Gly Tyr Gly Met His
1               5

<210> SEQ ID NO 93
<211> LENGTH: 18
<212> TYPE: PRT
<213> ORGANISM: Homo sapiens

<400> SEQUENCE: 93

Val Ile Ser Asn Asp Gly Ser Lys Lys Tyr Tyr Ser Asp Ser Val Lys
1               5                   10                  15

Gly Arg

<210> SEQ ID NO 94
<211> LENGTH: 12
<212> TYPE: PRT
<213> ORGANISM: Homo sapiens

<400> SEQUENCE: 94

Ser Ser Ser Ile Trp Leu Thr Gln Ser Leu Asp His
1               5                   10

<210> SEQ ID NO 95
<211> LENGTH: 5
<212> TYPE: PRT
<213> ORGANISM: Homo sapiens

```
<400> SEQUENCE: 95

Gly Tyr Gly Met His
1               5

<210> SEQ ID NO 96
<211> LENGTH: 18
<212> TYPE: PRT
<213> ORGANISM: Homo sapiens

<400> SEQUENCE: 96

Val Ile Ser Asn Asp Gly Ser Lys Lys Tyr Tyr Ser Asp Ser Val Lys
1               5                   10                  15

Gly Arg

<210> SEQ ID NO 97
<211> LENGTH: 12
<212> TYPE: PRT
<213> ORGANISM: Homo sapiens

<400> SEQUENCE: 97

Ser Ser Ser Ile Trp Leu Ser Gln Ser Leu Asp Gly
1               5                   10

<210> SEQ ID NO 98
<211> LENGTH: 5
<212> TYPE: PRT
<213> ORGANISM: Homo sapiens

<400> SEQUENCE: 98

Gly Tyr Gly Met His
1               5

<210> SEQ ID NO 99
<211> LENGTH: 18
<212> TYPE: PRT
<213> ORGANISM: Homo sapiens

<400> SEQUENCE: 99

Val Ile Ser Asn Asp Gly Ser Lys Lys Tyr Tyr Ser Asp Ser Val Lys
1               5                   10                  15

Gly Arg

<210> SEQ ID NO 100
<211> LENGTH: 12
<212> TYPE: PRT
<213> ORGANISM: Homo sapiens

<400> SEQUENCE: 100

Ser Ser Ser Ile Trp Leu Ser Gln Ser Leu Asp Gly
1               5                   10

<210> SEQ ID NO 101
<211> LENGTH: 5
<212> TYPE: PRT
<213> ORGANISM: Homo sapiens

<400> SEQUENCE: 101

Gly Tyr Gly Met His
1               5

<210> SEQ ID NO 102
<211> LENGTH: 18
<212> TYPE: PRT
```

<213> ORGANISM: Homo sapiens

<400> SEQUENCE: 102

Val Ile Ser Asn Asp Gly Ser Lys Lys Tyr Tyr Ser Asp Ser Val Lys
1               5                   10                  15

Gly Arg

<210> SEQ ID NO 103
<211> LENGTH: 12
<212> TYPE: PRT
<213> ORGANISM: Homo sapiens

<400> SEQUENCE: 103

Ser Ser Ser Ile Trp Leu Ser Gln Ser Leu Asp Gly
1               5                   10

<210> SEQ ID NO 104
<211> LENGTH: 5
<212> TYPE: PRT
<213> ORGANISM: Homo sapiens

<400> SEQUENCE: 104

Gly Tyr Gly Met His
1               5

<210> SEQ ID NO 105
<211> LENGTH: 18
<212> TYPE: PRT
<213> ORGANISM: Homo sapiens

<400> SEQUENCE: 105

Val Ile Ser Asn Asp Gly Ser Lys Lys Tyr Tyr Ser Asp Ser Val Lys
1               5                   10                  15

Gly Arg

<210> SEQ ID NO 106
<211> LENGTH: 12
<212> TYPE: PRT
<213> ORGANISM: Homo sapiens

<400> SEQUENCE: 106

Ser Ser Ser Ile Trp Leu Thr Ser Ala Leu Asn Leu
1               5                   10

<210> SEQ ID NO 107
<211> LENGTH: 5
<212> TYPE: PRT
<213> ORGANISM: Homo sapiens

<400> SEQUENCE: 107

Gly Tyr Gly Met His
1               5

<210> SEQ ID NO 108
<211> LENGTH: 18
<212> TYPE: PRT
<213> ORGANISM: Homo sapiens

<400> SEQUENCE: 108

Val Ile Ser Asn Asp Gly Ser Lys Lys Tyr Tyr Ser Asp Ser Val Lys
1               5                   10                  15

Gly Arg

```
<210> SEQ ID NO 109
<211> LENGTH: 12
<212> TYPE: PRT
<213> ORGANISM: Homo sapiens

<400> SEQUENCE: 109

Ser Ser Ser Ile Trp Phe Gly Glu Thr Val Asp Tyr
1               5                   10

<210> SEQ ID NO 110
<211> LENGTH: 5
<212> TYPE: PRT
<213> ORGANISM: Homo sapiens

<400> SEQUENCE: 110

Glu Leu Ser Met His
1               5

<210> SEQ ID NO 111
<211> LENGTH: 18
<212> TYPE: PRT
<213> ORGANISM: Homo sapiens

<400> SEQUENCE: 111

Gly Phe Asp Arg Glu Asp Asp Glu Thr Ile His Ala Gln Lys Phe Gln
1               5                   10                  15

Gly Arg

<210> SEQ ID NO 112
<211> LENGTH: 11
<212> TYPE: PRT
<213> ORGANISM: Homo sapiens

<400> SEQUENCE: 112

Leu Met Val Trp Gly Asp Phe Trp Ile Gln His
1               5                   10

<210> SEQ ID NO 113
<211> LENGTH: 5
<212> TYPE: PRT
<213> ORGANISM: Homo sapiens

<400> SEQUENCE: 113

Glu Leu Ser Met His
1               5

<210> SEQ ID NO 114
<211> LENGTH: 18
<212> TYPE: PRT
<213> ORGANISM: Homo sapiens

<400> SEQUENCE: 114

Gly Phe Asp Arg Glu Asp Asp Glu Thr Ile His Ala Gln Lys Phe Gln
1               5                   10                  15

Gly Arg

<210> SEQ ID NO 115
<211> LENGTH: 11
<212> TYPE: PRT
<213> ORGANISM: Homo sapiens

<400> SEQUENCE: 115

Leu Met Val Trp Gly Asp Phe Trp Ile Gln His
1               5                   10
```

<210> SEQ ID NO 116
<211> LENGTH: 5
<212> TYPE: PRT
<213> ORGANISM: Homo sapiens

<400> SEQUENCE: 116

Glu Leu Ser Met His
1               5

<210> SEQ ID NO 117
<211> LENGTH: 18
<212> TYPE: PRT
<213> ORGANISM: Homo sapiens

<400> SEQUENCE: 117

Gly Phe Asp Arg Glu Asp Asp Glu Thr Ile His Ala Gln Lys Phe Gln
1               5                   10                  15

Gly Arg

<210> SEQ ID NO 118
<211> LENGTH: 11
<212> TYPE: PRT
<213> ORGANISM: Homo sapiens

<400> SEQUENCE: 118

Leu Met Ala Trp Asp Tyr Pro Pro Ile Gln His
1               5                   10

<210> SEQ ID NO 119
<211> LENGTH: 5
<212> TYPE: PRT
<213> ORGANISM: Homo sapiens

<400> SEQUENCE: 119

Glu Leu Ser Met His
1               5

<210> SEQ ID NO 120
<211> LENGTH: 18
<212> TYPE: PRT
<213> ORGANISM: Homo sapiens

<400> SEQUENCE: 120

Gly Phe Asp Arg Glu Asp Asp Glu Thr Ile His Ala Gln Lys Phe Gln
1               5                   10                  15

Gly Arg

<210> SEQ ID NO 121
<211> LENGTH: 11
<212> TYPE: PRT
<213> ORGANISM: Homo sapiens

<400> SEQUENCE: 121

Leu Met Val Trp Asn Phe Pro Pro Ile Gln His
1               5                   10

<210> SEQ ID NO 122
<211> LENGTH: 5
<212> TYPE: PRT
<213> ORGANISM: Homo sapiens

<400> SEQUENCE: 122

Glu Leu Ser Met His
1               5

```
<210> SEQ ID NO 123
<211> LENGTH: 18
<212> TYPE: PRT
<213> ORGANISM: Homo sapiens

<400> SEQUENCE: 123

Gly Phe Asp Arg Glu Asp Asp Glu Thr Ile His Ala Gln Lys Phe Gln
1               5                   10                  15

Gly Arg

<210> SEQ ID NO 124
<211> LENGTH: 11
<212> TYPE: PRT
<213> ORGANISM: Homo sapiens

<400> SEQUENCE: 124

Leu Met Val Trp Gly Asp Phe Trp Ile Gln His
1               5                   10

<210> SEQ ID NO 125
<211> LENGTH: 5
<212> TYPE: PRT
<213> ORGANISM: Homo sapiens

<400> SEQUENCE: 125

Ser Tyr Ala Met Ser
1               5

<210> SEQ ID NO 126
<211> LENGTH: 18
<212> TYPE: PRT
<213> ORGANISM: Homo sapiens

<400> SEQUENCE: 126

Ala Ile Ser Gly Ser Gly Gly Gly Thr Tyr Tyr Ala Asp Ser Val Lys
1               5                   10                  15

Gly Arg

<210> SEQ ID NO 127
<211> LENGTH: 8
<212> TYPE: PRT
<213> ORGANISM: Homo sapiens

<400> SEQUENCE: 127

Arg Gly Asp Tyr Arg Thr Asp Ile
1               5

<210> SEQ ID NO 128
<211> LENGTH: 5
<212> TYPE: PRT
<213> ORGANISM: Homo sapiens

<400> SEQUENCE: 128

Ser Tyr Ala Met Ser
1               5

<210> SEQ ID NO 129
<211> LENGTH: 18
<212> TYPE: PRT
<213> ORGANISM: Homo sapiens

<400> SEQUENCE: 129

Ala Ile Ser Gly Ser Gly Gly Gly Thr Tyr Tyr Ala Asp Ser Val Lys
```

```
                1               5                  10                 15

Gly Arg

<210> SEQ ID NO 130
<211> LENGTH: 8
<212> TYPE: PRT
<213> ORGANISM: Homo sapiens

<400> SEQUENCE: 130

Arg Gly Asp Tyr Arg Thr Asp Ile
1               5

<210> SEQ ID NO 131
<211> LENGTH: 5
<212> TYPE: PRT
<213> ORGANISM: Homo sapiens

<400> SEQUENCE: 131

Ser Tyr Ala Met Ser
1               5

<210> SEQ ID NO 132
<211> LENGTH: 11
<212> TYPE: PRT
<213> ORGANISM: Homo sapiens

<400> SEQUENCE: 132

Ala Ile Ser Gly Ser Gly Gly Ser Thr Tyr Tyr
1               5                  10

<210> SEQ ID NO 133
<211> LENGTH: 8
<212> TYPE: PRT
<213> ORGANISM: Homo sapiens

<400> SEQUENCE: 133

Arg Gly Asp Tyr Arg Thr Asp Ile
1               5

<210> SEQ ID NO 134
<211> LENGTH: 5
<212> TYPE: PRT
<213> ORGANISM: Homo sapiens

<400> SEQUENCE: 134

Ser Tyr Ala Met Ser
1               5

<210> SEQ ID NO 135
<211> LENGTH: 11
<212> TYPE: PRT
<213> ORGANISM: Homo sapiens

<400> SEQUENCE: 135

Ala Ile Ser Gly Ser Gly Gly Ser Thr Tyr Tyr
1               5                  10

<210> SEQ ID NO 136
<211> LENGTH: 8
<212> TYPE: PRT
<213> ORGANISM: Homo sapiens

<400> SEQUENCE: 136

Arg Gly Asp Tyr Arg Thr Asp Ile
1               5
```

```
<210> SEQ ID NO 137
<211> LENGTH: 5
<212> TYPE: PRT
<213> ORGANISM: Homo sapiens

<400> SEQUENCE: 137

Ser Tyr Ala Met Ser
1               5

<210> SEQ ID NO 138
<211> LENGTH: 11
<212> TYPE: PRT
<213> ORGANISM: Homo sapiens

<400> SEQUENCE: 138

Ala Ile Ser Gly Ser Gly Gly Ser Thr Tyr Tyr
1               5                   10

<210> SEQ ID NO 139
<211> LENGTH: 9
<212> TYPE: PRT
<213> ORGANISM: Homo sapiens

<400> SEQUENCE: 139

Val Arg Gly Ile Tyr Gly Met Asp Val
1               5

<210> SEQ ID NO 140
<211> LENGTH: 11
<212> TYPE: PRT
<213> ORGANISM: Homo sapiens

<400> SEQUENCE: 140

Ser Gly Asp Lys Leu Gly Asp Lys Tyr Ala Ser
1               5                   10

<210> SEQ ID NO 141
<211> LENGTH: 7
<212> TYPE: PRT
<213> ORGANISM: Homo sapiens

<400> SEQUENCE: 141

Gln Asp Ser Asn Arg Pro Ser
1               5

<210> SEQ ID NO 142
<211> LENGTH: 10
<212> TYPE: PRT
<213> ORGANISM: Homo sapiens

<400> SEQUENCE: 142

Gln Ala Trp Asp Ser Ser Thr Ala Ser Val
1               5                   10

<210> SEQ ID NO 143
<211> LENGTH: 11
<212> TYPE: PRT
<213> ORGANISM: Homo sapiens

<400> SEQUENCE: 143

Ser Gly Asp Lys Leu Gly Asp Lys Tyr Ala Ser
1               5                   10

<210> SEQ ID NO 144
```

```
<211> LENGTH: 7
<212> TYPE: PRT
<213> ORGANISM: Homo sapiens

<400> SEQUENCE: 144

Gln Asp Ser Asn Arg Pro Ser
1               5

<210> SEQ ID NO 145
<211> LENGTH: 10
<212> TYPE: PRT
<213> ORGANISM: Homo sapiens

<400> SEQUENCE: 145

Gln Ala Trp Asp His Ser Leu Gln His Arg
1               5                   10

<210> SEQ ID NO 146
<211> LENGTH: 11
<212> TYPE: PRT
<213> ORGANISM: Homo sapiens

<400> SEQUENCE: 146

Ser Gly Asp Lys Leu Gly Asp Lys Tyr Ala Ser
1               5                   10

<210> SEQ ID NO 147
<211> LENGTH: 7
<212> TYPE: PRT
<213> ORGANISM: Homo sapiens

<400> SEQUENCE: 147

Gln Asp Ser Asn Arg Pro Ser
1               5

<210> SEQ ID NO 148
<211> LENGTH: 10
<212> TYPE: PRT
<213> ORGANISM: Homo sapiens

<400> SEQUENCE: 148

Gln Ala Trp Thr Ser Ala Leu Asn Ser Gln
1               5                   10

<210> SEQ ID NO 149
<211> LENGTH: 11
<212> TYPE: PRT
<213> ORGANISM: Homo sapiens

<400> SEQUENCE: 149

Ser Gly Asp Lys Leu Gly Asp Lys Tyr Ala Ser
1               5                   10

<210> SEQ ID NO 150
<211> LENGTH: 7
<212> TYPE: PRT
<213> ORGANISM: Homo sapiens

<400> SEQUENCE: 150

Gln Asp Ser Asn Arg Pro Ser
1               5

<210> SEQ ID NO 151
<211> LENGTH: 10
<212> TYPE: PRT
<213> ORGANISM: Homo sapiens
```

```
<400> SEQUENCE: 151

Gln Ala Trp Thr His Ser Leu Ser Thr Leu
1               5                   10

<210> SEQ ID NO 152
<211> LENGTH: 11
<212> TYPE: PRT
<213> ORGANISM: Homo sapiens

<400> SEQUENCE: 152

Ser Gly Asp Lys Leu Gly Asp Lys Tyr Ala Ser
1               5                   10

<210> SEQ ID NO 153
<211> LENGTH: 7
<212> TYPE: PRT
<213> ORGANISM: Homo sapiens

<400> SEQUENCE: 153

Gln Asp Ser Asn Arg Pro Ser
1               5

<210> SEQ ID NO 154
<211> LENGTH: 10
<212> TYPE: PRT
<213> ORGANISM: Homo sapiens

<400> SEQUENCE: 154

Gln Ala Trp Thr His Ser Leu Ser Thr Leu
1               5                   10

<210> SEQ ID NO 155
<211> LENGTH: 13
<212> TYPE: PRT
<213> ORGANISM: Homo sapiens

<400> SEQUENCE: 155

Ser Gly Arg Asn Ser Asn Ile Gly Ser Tyr Thr Val Thr
1               5                   10

<210> SEQ ID NO 156
<211> LENGTH: 7
<212> TYPE: PRT
<213> ORGANISM: Homo sapiens

<400> SEQUENCE: 156

Ser Asn Ser Gln Arg Pro Ser
1               5

<210> SEQ ID NO 157
<211> LENGTH: 11
<212> TYPE: PRT
<213> ORGANISM: Homo sapiens

<400> SEQUENCE: 157

Ala Ala Trp Asp Asp Ser Leu Asn Gly Pro Val
1               5                   10

<210> SEQ ID NO 158
<211> LENGTH: 13
<212> TYPE: PRT
<213> ORGANISM: Homo sapiens

<400> SEQUENCE: 158
```

Ser Gly Arg Asn Ser Asn Ile Gly Ser Tyr Thr Val Thr
1               5                   10

<210> SEQ ID NO 159
<211> LENGTH: 7
<212> TYPE: PRT
<213> ORGANISM: Homo sapiens

<400> SEQUENCE: 159

Ser Asn Ser Gln Arg Pro Ser
1               5

<210> SEQ ID NO 160
<211> LENGTH: 11
<212> TYPE: PRT
<213> ORGANISM: Homo sapiens

<400> SEQUENCE: 160

Val Val Trp Asp Asp Val Leu Asn Gly Pro Val
1               5                   10

<210> SEQ ID NO 161
<211> LENGTH: 13
<212> TYPE: PRT
<213> ORGANISM: Homo sapiens

<400> SEQUENCE: 161

Ser Gly Arg Asn Ser Asn Ile Gly Ser Tyr Thr Val Thr
1               5                   10

<210> SEQ ID NO 162
<211> LENGTH: 7
<212> TYPE: PRT
<213> ORGANISM: Homo sapiens

<400> SEQUENCE: 162

Ser Asn Ser Gln Arg Pro Ser
1               5

<210> SEQ ID NO 163
<211> LENGTH: 11
<212> TYPE: PRT
<213> ORGANISM: Homo sapiens

<400> SEQUENCE: 163

Val Val Trp Asp Asp Lys Leu Asn Gly Pro Val
1               5                   10

<210> SEQ ID NO 164
<211> LENGTH: 13
<212> TYPE: PRT
<213> ORGANISM: Homo sapiens

<400> SEQUENCE: 164

Ser Gly Arg Asn Ser Asn Ile Gly Ser Tyr Thr Val Thr
1               5                   10

<210> SEQ ID NO 165
<211> LENGTH: 7
<212> TYPE: PRT
<213> ORGANISM: Homo sapiens

<400> SEQUENCE: 165

Ser Asn Ser Gln Arg Pro Ser
1               5

<210> SEQ ID NO 166
<211> LENGTH: 11
<212> TYPE: PRT
<213> ORGANISM: Homo sapiens

<400> SEQUENCE: 166

Val Val Trp Asp Glu Ile Leu Asn Gly Pro Val
1               5                   10

<210> SEQ ID NO 167
<211> LENGTH: 11
<212> TYPE: PRT
<213> ORGANISM: Homo sapiens

<400> SEQUENCE: 167

Gln Gly Asp Ser Leu Arg Ser Tyr Tyr Ala Ser
1               5                   10

<210> SEQ ID NO 168
<211> LENGTH: 7
<212> TYPE: PRT
<213> ORGANISM: Homo sapiens

<400> SEQUENCE: 168

Ala Lys Asn Asn Arg Pro Ser
1               5

<210> SEQ ID NO 169
<211> LENGTH: 10
<212> TYPE: PRT
<213> ORGANISM: Homo sapiens

<400> SEQUENCE: 169

Asn Ser Arg Asp Ser Ser Asn His Val Val
1               5                   10

<210> SEQ ID NO 170
<211> LENGTH: 13
<212> TYPE: PRT
<213> ORGANISM: Homo sapiens

<400> SEQUENCE: 170

Ser Gly Arg Asn Ser Asn Ile Gly Ser Tyr Thr Val Thr
1               5                   10

<210> SEQ ID NO 171
<211> LENGTH: 7
<212> TYPE: PRT
<213> ORGANISM: Homo sapiens

<400> SEQUENCE: 171

Ser Asn Ser Gln Arg Pro Ser
1               5

<210> SEQ ID NO 172
<211> LENGTH: 11
<212> TYPE: PRT
<213> ORGANISM: Homo sapiens

<400> SEQUENCE: 172

Leu Val Trp Asp Asp Val Leu Asn Gly Pro Val
1               5                   10

<210> SEQ ID NO 173
<211> LENGTH: 11

```
<212> TYPE: PRT
<213> ORGANISM: Homo sapiens

<400> SEQUENCE: 173

Gln Gly Asp Ser Leu Arg Ser Tyr Tyr Ala Ser
1               5                   10

<210> SEQ ID NO 174
<211> LENGTH: 7
<212> TYPE: PRT
<213> ORGANISM: Homo sapiens

<400> SEQUENCE: 174

Ala Lys Asn Asn Arg Pro Ser
1               5

<210> SEQ ID NO 175
<211> LENGTH: 10
<212> TYPE: PRT
<213> ORGANISM: Homo sapiens

<400> SEQUENCE: 175

Ala Ser Arg Asn Gly Trp Asn His Val Val
1               5                   10

<210> SEQ ID NO 176
<211> LENGTH: 11
<212> TYPE: PRT
<213> ORGANISM: Homo sapiens

<400> SEQUENCE: 176

Gln Gly Asp Ser Leu Arg Ser Tyr Tyr Ala Ser
1               5                   10

<210> SEQ ID NO 177
<211> LENGTH: 7
<212> TYPE: PRT
<213> ORGANISM: Homo sapiens

<400> SEQUENCE: 177

Ala Lys Asn Asn Arg Pro Ser
1               5

<210> SEQ ID NO 178
<211> LENGTH: 10
<212> TYPE: PRT
<213> ORGANISM: Homo sapiens

<400> SEQUENCE: 178

Ala Ser Arg Asn Gly Trp Asn His Val Val
1               5                   10

<210> SEQ ID NO 179
<211> LENGTH: 11
<212> TYPE: PRT
<213> ORGANISM: Homo sapiens

<400> SEQUENCE: 179

Gln Gly Asp Ser Leu Arg Ser Tyr Tyr Ala Ser
1               5                   10

<210> SEQ ID NO 180
<211> LENGTH: 7
<212> TYPE: PRT
<213> ORGANISM: Homo sapiens
```

```
<400> SEQUENCE: 180

Ala Lys Asn Asn Arg Pro Ser
1               5

<210> SEQ ID NO 181
<211> LENGTH: 10
<212> TYPE: PRT
<213> ORGANISM: Homo sapiens

<400> SEQUENCE: 181

Ala Ser Arg Asn Gly Trp Asn His Val Val
1               5                   10

<210> SEQ ID NO 182
<211> LENGTH: 11
<212> TYPE: PRT
<213> ORGANISM: Homo sapiens

<400> SEQUENCE: 182

Gln Gly Asp Ser Leu Arg Ser Tyr Tyr Ala Ser
1               5                   10

<210> SEQ ID NO 183
<211> LENGTH: 7
<212> TYPE: PRT
<213> ORGANISM: Homo sapiens

<400> SEQUENCE: 183

Ala Lys Asn Asn Arg Pro Ser
1               5

<210> SEQ ID NO 184
<211> LENGTH: 10
<212> TYPE: PRT
<213> ORGANISM: Homo sapiens

<400> SEQUENCE: 184

Ala Ser Arg Asn Gly Trp Asn His Val Val
1               5                   10

<210> SEQ ID NO 185
<211> LENGTH: 11
<212> TYPE: PRT
<213> ORGANISM: Homo sapiens

<400> SEQUENCE: 185

Gln Gly Asp Ser Leu Arg Ser Tyr Tyr Ala Ser
1               5                   10

<210> SEQ ID NO 186
<211> LENGTH: 7
<212> TYPE: PRT
<213> ORGANISM: Homo sapiens

<400> SEQUENCE: 186

Ala Lys Asn Asn Arg Pro Ser
1               5

<210> SEQ ID NO 187
<211> LENGTH: 10
<212> TYPE: PRT
<213> ORGANISM: Homo sapiens

<400> SEQUENCE: 187

Ala Thr Arg Asn Gly Trp Asn His Val Val
```

<210> SEQ ID NO 188
<211> LENGTH: 11
<212> TYPE: PRT
<213> ORGANISM: Homo sapiens

<400> SEQUENCE: 188

Gln Gly Asp Ser Leu Arg Ser Tyr Tyr Ala Ser
1               5                   10

<210> SEQ ID NO 189
<211> LENGTH: 7
<212> TYPE: PRT
<213> ORGANISM: Homo sapiens

<400> SEQUENCE: 189

Ala Lys Asn Asn Arg Pro Ser
1               5

<210> SEQ ID NO 190
<211> LENGTH: 10
<212> TYPE: PRT
<213> ORGANISM: Homo sapiens

<400> SEQUENCE: 190

Ala Thr Arg Asn Gly Trp Asn His Val Val
1               5                   10

<210> SEQ ID NO 191
<211> LENGTH: 15
<212> TYPE: DNA
<213> ORGANISM: Homo sapiens

<400> SEQUENCE: 191
ggttatggca tgcac                                              15

<210> SEQ ID NO 192
<211> LENGTH: 54
<212> TYPE: DNA
<213> ORGANISM: Homo sapiens

<400> SEQUENCE: 192
gtaatatcaa atgatggaag taagaaatat tattcagact ccgtgaaggg ccga    54

<210> SEQ ID NO 193
<211> LENGTH: 36
<212> TYPE: DNA
<213> ORGANISM: Homo sapiens

<400> SEQUENCE: 193
tccagttcca tatggctgac ccagtccctg gaccac                       36

<210> SEQ ID NO 194
<211> LENGTH: 15
<212> TYPE: DNA
<213> ORGANISM: Homo sapiens

<400> SEQUENCE: 194
ggttatggca tgcac                                              15

<210> SEQ ID NO 195
<211> LENGTH: 54
<212> TYPE: DNA

-continued

```
<400> SEQUENCE: 195
gtaatatcaa atgatggaag taagaaatat tattcagact ccgtgaaggg ccga          54

<210> SEQ ID NO 196
<211> LENGTH: 36
<212> TYPE: DNA
<213> ORGANISM: Homo sapiens

<400> SEQUENCE: 196
tccagttcca tatggctgac ccagtccctg gaccac                              36

<210> SEQ ID NO 197
<211> LENGTH: 15
<212> TYPE: DNA
<213> ORGANISM: Homo sapiens

<400> SEQUENCE: 197
ggttatggca tgcac                                                     15

<210> SEQ ID NO 198
<211> LENGTH: 54
<212> TYPE: DNA
<213> ORGANISM: Homo sapiens

<400> SEQUENCE: 198
gtaatatcaa atgatggaag taagaaatat tattcagact ccgtgaaggg ccga          54

<210> SEQ ID NO 199
<211> LENGTH: 36
<212> TYPE: DNA
<213> ORGANISM: Homo sapiens

<400> SEQUENCE: 199
tccagttcca tatggctgtc gcagtccctg gacggc                              36

<210> SEQ ID NO 200
<211> LENGTH: 15
<212> TYPE: DNA
<213> ORGANISM: Homo sapiens

<400> SEQUENCE: 200
ggttatggca tgcac                                                     15

<210> SEQ ID NO 201
<211> LENGTH: 54
<212> TYPE: DNA
<213> ORGANISM: Homo sapiens

<400> SEQUENCE: 201
gtaatatcaa atgatggaag taagaaatat tattcagact ccgtgaaggg ccga          54

<210> SEQ ID NO 202
<211> LENGTH: 36
<212> TYPE: DNA
<213> ORGANISM: Homo sapiens

<400> SEQUENCE: 202
tccagttcca tatggctgtc gcagtccctg gacggc                              36

<210> SEQ ID NO 203
<211> LENGTH: 15
<212> TYPE: DNA
<213> ORGANISM: Homo sapiens
```

```
<400> SEQUENCE: 203
ggttatggca tgcac                                                         15

<210> SEQ ID NO 204
<211> LENGTH: 54
<212> TYPE: DNA
<213> ORGANISM: Homo sapiens

<400> SEQUENCE: 204
gtaatatcaa atgatggaag taagaaatat tattcagact ccgtgaaggg ccga              54

<210> SEQ ID NO 205
<211> LENGTH: 36
<212> TYPE: DNA
<213> ORGANISM: Homo sapiens

<400> SEQUENCE: 205
tccagttcca tatggctgac ctcggccctg aacctg                                  36

<210> SEQ ID NO 206
<211> LENGTH: 15
<212> TYPE: DNA
<213> ORGANISM: Homo sapiens

<400> SEQUENCE: 206
ggttatggca tgcac                                                         15

<210> SEQ ID NO 207
<211> LENGTH: 54
<212> TYPE: DNA
<213> ORGANISM: Homo sapiens

<400> SEQUENCE: 207
gtaatatcaa atgatggaag taagaaatat tattcagact ccgtgaaggg ccga              54

<210> SEQ ID NO 208
<211> LENGTH: 36
<212> TYPE: DNA
<213> ORGANISM: Homo sapiens

<400> SEQUENCE: 208
tccagttcca tatggctgac ctcggccctg aacctg                                  36

<210> SEQ ID NO 209
<211> LENGTH: 15
<212> TYPE: DNA
<213> ORGANISM: Homo sapiens

<400> SEQUENCE: 209
ggttatggca tgcac                                                         15

<210> SEQ ID NO 210
<211> LENGTH: 54
<212> TYPE: DNA
<213> ORGANISM: Homo sapiens

<400> SEQUENCE: 210
gtaatatcaa atgatggaag taagaaatat tattcagact ccgtgaaggg ccga              54

<210> SEQ ID NO 211
<211> LENGTH: 36
<212> TYPE: DNA
<213> ORGANISM: Homo sapiens
```

```
<400> SEQUENCE: 211
tccagttcca tatggttcgg ggagaccgtt gactac                              36

<210> SEQ ID NO 212
<211> LENGTH: 15
<212> TYPE: DNA
<213> ORGANISM: Homo sapiens

<400> SEQUENCE: 212
gaattatcca tgcac                                                    15

<210> SEQ ID NO 213
<211> LENGTH: 54
<212> TYPE: DNA
<213> ORGANISM: Homo sapiens

<400> SEQUENCE: 213
ggttttgatc gtgaagatga tgaaacaatc cacgcacaga agttccaggg caga         54

<210> SEQ ID NO 214
<211> LENGTH: 33
<212> TYPE: DNA
<213> ORGANISM: Homo sapiens

<400> SEQUENCE: 214
cttatggtgt ggggcgattt ttggatccag cac                                33

<210> SEQ ID NO 215
<211> LENGTH: 15
<212> TYPE: DNA
<213> ORGANISM: Homo sapiens

<400> SEQUENCE: 215
gaattatcca tgcac                                                    15

<210> SEQ ID NO 216
<211> LENGTH: 54
<212> TYPE: DNA
<213> ORGANISM: Homo sapiens

<400> SEQUENCE: 216
ggttttgatc gtgaagatga tgaaacaatc cacgcacaga agttccaggg caga         54

<210> SEQ ID NO 217
<211> LENGTH: 33
<212> TYPE: DNA
<213> ORGANISM: Homo sapiens

<400> SEQUENCE: 217
cttatggtgt ggggcgattt ttggatccag cac                                33

<210> SEQ ID NO 218
<211> LENGTH: 15
<212> TYPE: DNA
<213> ORGANISM: Homo sapiens

<400> SEQUENCE: 218
gaattatcca tgcac                                                    15

<210> SEQ ID NO 219
<211> LENGTH: 54
<212> TYPE: DNA
<213> ORGANISM: Homo sapiens
```

<400> SEQUENCE: 219
ggttttgatc gtgaagatga tgaaacaatc cacgcacaga agttccaggg caga        54

<210> SEQ ID NO 220
<211> LENGTH: 33
<212> TYPE: DNA
<213> ORGANISM: Homo sapiens

<400> SEQUENCE: 220
cttatggcct gggactaccc gcccatccag cac        33

<210> SEQ ID NO 221
<211> LENGTH: 15
<212> TYPE: DNA
<213> ORGANISM: Homo sapiens

<400> SEQUENCE: 221
gaattatcca tgcac        15

<210> SEQ ID NO 222
<211> LENGTH: 54
<212> TYPE: DNA
<213> ORGANISM: Homo sapiens

<400> SEQUENCE: 222
ggttttgatc gtgaagatga tgaaacaatc cacgcacaga agttccaggg caga        54

<210> SEQ ID NO 223
<211> LENGTH: 33
<212> TYPE: DNA
<213> ORGANISM: Homo sapiens

<400> SEQUENCE: 223
cttatggtgt ggaacttccc ccccatccag cac        33

<210> SEQ ID NO 224
<211> LENGTH: 15
<212> TYPE: DNA
<213> ORGANISM: Homo sapiens

<400> SEQUENCE: 224
gaattatcca tgcac        15

<210> SEQ ID NO 225
<211> LENGTH: 54
<212> TYPE: DNA
<213> ORGANISM: Homo sapiens

<400> SEQUENCE: 225
ggttttgatc gtgaagatga tgaaacaatc cacgcacaga agttccaggg caga        54

<210> SEQ ID NO 226
<211> LENGTH: 33
<212> TYPE: DNA
<213> ORGANISM: Homo sapiens

<400> SEQUENCE: 226
cttatggtgt ggggcgattt ttggatccag cac        33

<210> SEQ ID NO 227
<211> LENGTH: 15
<212> TYPE: DNA
<213> ORGANISM: Homo sapiens

```
<400> SEQUENCE: 227
agctatgcca tgagc                                                    15

<210> SEQ ID NO 228
<211> LENGTH: 54
<212> TYPE: DNA
<213> ORGANISM: Homo sapiens

<400> SEQUENCE: 228
gctattagtg gtagtggtgg tggcacatac tacgcagact ccgtgaaggg ccgg         54

<210> SEQ ID NO 229
<211> LENGTH: 24
<212> TYPE: DNA
<213> ORGANISM: Homo sapiens

<400> SEQUENCE: 229
cggggcgact accggacgga catc                                          24

<210> SEQ ID NO 230
<211> LENGTH: 15
<212> TYPE: DNA
<213> ORGANISM: Homo sapiens

<400> SEQUENCE: 230
agctatgcca tgagc                                                    15

<210> SEQ ID NO 231
<211> LENGTH: 54
<212> TYPE: DNA
<213> ORGANISM: Homo sapiens

<400> SEQUENCE: 231
gctattagtg gtagtggtgg tggcacatac tacgcagact ccgtgaaggg ccgg         54

<210> SEQ ID NO 232
<211> LENGTH: 24
<212> TYPE: DNA
<213> ORGANISM: Homo sapiens

<400> SEQUENCE: 232 cgggggact accggacgga catc                                           24

<210> SEQ ID NO 233
<211> LENGTH: 15
<212> TYPE: DNA
<213> ORGANISM: Homo sapiens

<400> SEQUENCE: 233
agctatgcca tgagc                                                    15

<210> SEQ ID NO 234
<211> LENGTH: 33
<212> TYPE: DNA
<213> ORGANISM: Homo sapiens

<400> SEQUENCE: 234
gctattagtg gtagtggtgg tagcacatac tac                                33

<210> SEQ ID NO 235
<211> LENGTH: 24
<212> TYPE: DNA
<213> ORGANISM: Homo sapiens
```

```
<400> SEQUENCE: 235 cgggggact accggacgga catc                                          24

<210> SEQ ID NO 236
<211> LENGTH: 15
<212> TYPE: DNA
<213> ORGANISM: Homo sapiens

<400> SEQUENCE: 236
agctatgcca tgagc                                                   15

<210> SEQ ID NO 237
<211> LENGTH: 33
<212> TYPE: DNA
<213> ORGANISM: Homo sapiens

<400> SEQUENCE: 237
gctattagtg gtagtggtgg tagcacatac tac                               33

<210> SEQ ID NO 238
<211> LENGTH: 24
<212> TYPE: DNA
<213> ORGANISM: Homo sapiens

<400> SEQUENCE: 238 cgggggact accggacgga catc                                          24

<210> SEQ ID NO 239
<211> LENGTH: 15
<212> TYPE: DNA
<213> ORGANISM: Homo sapiens

<400> SEQUENCE: 239
agctatgcca tgagc                                                   15

<210> SEQ ID NO 240
<211> LENGTH: 33
<212> TYPE: DNA
<213> ORGANISM: Homo sapiens

<400> SEQUENCE: 240
gctattagtg gtagtggtgg tagcacatac tac                               33

<210> SEQ ID NO 241
<211> LENGTH: 27
<212> TYPE: DNA
<213> ORGANISM: Homo sapiens

<400> SEQUENCE: 241
gttcggggca tatacggtat ggacgtc                                      27

<210> SEQ ID NO 242
<211> LENGTH: 33
<212> TYPE: DNA
<213> ORGANISM: Homo sapiens

<400> SEQUENCE: 242
tctggagata aattggggga taaatatgct tcc                               33

<210> SEQ ID NO 243
<211> LENGTH: 21
<212> TYPE: DNA
<213> ORGANISM: Homo sapiens
```

```
<400> SEQUENCE: 243
caagattcca atcggccctc a                                           21

<210> SEQ ID NO 244
<211> LENGTH: 30
<212> TYPE: DNA
<213> ORGANISM: Homo sapiens

<400> SEQUENCE: 244
caggcgtggg acagcagcac tgcatcggtg                                  30

<210> SEQ ID NO 245
<211> LENGTH: 33
<212> TYPE: DNA
<213> ORGANISM: Homo sapiens

<400> SEQUENCE: 245
tctggagata aattggggga taaatatgct tcc                              33

<210> SEQ ID NO 246
<211> LENGTH: 21
<212> TYPE: DNA
<213> ORGANISM: Homo sapiens

<400> SEQUENCE: 246
caagattcca atcggccctc a                                           21

<210> SEQ ID NO 247
<211> LENGTH: 30
<212> TYPE: DNA
<213> ORGANISM: Homo sapiens

<400> SEQUENCE: 247
caggcgtggg accactcctt gcagcacagg                                  30

<210> SEQ ID NO 248
<211> LENGTH: 33
<212> TYPE: DNA
<213> ORGANISM: Homo sapiens

<400> SEQUENCE: 248
tctggagata aattggggga taaatatgct tcc                              33

<210> SEQ ID NO 249
<211> LENGTH: 21
<212> TYPE: DNA
<213> ORGANISM: Homo sapiens

<400> SEQUENCE: 249
caagattcca atcggccctc a                                           21

<210> SEQ ID NO 250
<211> LENGTH: 30
<212> TYPE: DNA
<213> ORGANISM: Homo sapiens

<400> SEQUENCE: 250
caggcgtgga ccagcgccct gaactcgcag                                  30

<210> SEQ ID NO 251
<211> LENGTH: 33
<212> TYPE: DNA
<213> ORGANISM: Homo sapiens
```

```
<400> SEQUENCE: 251
tctggagata aattgggga taaatatgct tcc                           33

<210> SEQ ID NO 252
<211> LENGTH: 21
<212> TYPE: DNA
<213> ORGANISM: Homo sapiens

<400> SEQUENCE: 252
caagattcca atcggccctc a                                       21

<210> SEQ ID NO 253
<211> LENGTH: 30
<212> TYPE: DNA
<213> ORGANISM: Homo sapiens

<400> SEQUENCE: 253
caggcgtgga cgcactccct cagcacgttg                              30

<210> SEQ ID NO 254
<211> LENGTH: 33
<212> TYPE: DNA
<213> ORGANISM: Homo sapiens

<400> SEQUENCE: 254
tctggagata aattgggga taaatatgct tcc                           33

<210> SEQ ID NO 255
<211> LENGTH: 21
<212> TYPE: DNA
<213> ORGANISM: Homo sapiens

<400> SEQUENCE: 255
caagattcca atcggccctc a                                       21

<210> SEQ ID NO 256
<211> LENGTH: 30
<212> TYPE: DNA
<213> ORGANISM: Homo sapiens

<400> SEQUENCE: 256
caggcgtgga cccacagcct gagcacgttg                              30

<210> SEQ ID NO 257
<211> LENGTH: 39
<212> TYPE: DNA
<213> ORGANISM: Homo sapiens

<400> SEQUENCE: 257
tctggaagga actccaacat cggaagttat actgtaacc                    39

<210> SEQ ID NO 258
<211> LENGTH: 21
<212> TYPE: DNA
<213> ORGANISM: Homo sapiens

<400> SEQUENCE: 258
agtaatagtc agcggccctc a                                       21

<210> SEQ ID NO 259
<211> LENGTH: 33
<212> TYPE: DNA
<213> ORGANISM: Homo sapiens
```

```
<400> SEQUENCE: 259
gcagcatggg atgacagcct gaatggcccg gtg                                    33

<210> SEQ ID NO 260
<211> LENGTH: 39
<212> TYPE: DNA
<213> ORGANISM: Homo sapiens

<400> SEQUENCE: 260
tctggaagga actccaacat cggaagttat actgtaacc                              39

<210> SEQ ID NO 261
<211> LENGTH: 21
<212> TYPE: DNA
<213> ORGANISM: Homo sapiens

<400> SEQUENCE: 261
agtaatagtc agcggccctc a                                                 21

<210> SEQ ID NO 262
<211> LENGTH: 33
<212> TYPE: DNA
<213> ORGANISM: Homo sapiens

<400> SEQUENCE: 262
gtggtgtggg atgacgtgct gaatggcccg gtg                                    33

<210> SEQ ID NO 263
<211> LENGTH: 39
<212> TYPE: DNA
<213> ORGANISM: Homo sapiens

<400> SEQUENCE: 263
tctggaagga actccaacat cggaagttat actgtaacc                              39

<210> SEQ ID NO 264
<211> LENGTH: 21
<212> TYPE: DNA
<213> ORGANISM: Homo sapiens

<400> SEQUENCE: 264
agtaatagtc agcggccctc a                                                 21

<210> SEQ ID NO 265
<211> LENGTH: 33
<212> TYPE: DNA
<213> ORGANISM: Homo sapiens

<400> SEQUENCE: 265
gtcgtgtggg atgacaagct gaatggcccg gtg                                    33

<210> SEQ ID NO 266
<211> LENGTH: 39
<212> TYPE: DNA
<213> ORGANISM: Homo sapiens

<400> SEQUENCE: 266
tctggaagga actccaacat cggaagttat actgtaacc                              39

<210> SEQ ID NO 267
<211> LENGTH: 21
<212> TYPE: DNA
<213> ORGANISM: Homo sapiens
```

```
<400> SEQUENCE: 267
agtaatagtc agcggccctc a                                        21

<210> SEQ ID NO 268
<211> LENGTH: 33
<212> TYPE: DNA
<213> ORGANISM: Homo sapiens

<400> SEQUENCE: 268
gtggtgtggg acgagatcct gaatggcccg gtg                           33

<210> SEQ ID NO 269
<211> LENGTH: 33
<212> TYPE: DNA
<213> ORGANISM: Homo sapiens

<400> SEQUENCE: 269
caaggagaca gcctcagaag ctattatgca agc                           33

<210> SEQ ID NO 270
<211> LENGTH: 21
<212> TYPE: DNA
<213> ORGANISM: Homo sapiens

<400> SEQUENCE: 270
gctaaaaaca accggccctc a                                        21

<210> SEQ ID NO 271
<211> LENGTH: 33
<212> TYPE: DNA
<213> ORGANISM: Homo sapiens

<400> SEQUENCE: 271
tgtaactccc gggacagcag taaccatgtg gta                           33

<210> SEQ ID NO 272
<211> LENGTH: 39
<212> TYPE: DNA
<213> ORGANISM: Homo sapiens

<400> SEQUENCE: 272
tctggaagga actccaacat cggaagttat actgtaacc                     39

<210> SEQ ID NO 273
<211> LENGTH: 21
<212> TYPE: DNA
<213> ORGANISM: Homo sapiens

<400> SEQUENCE: 273
agtaatagtc agcggccctc a                                        21

<210> SEQ ID NO 274
<211> LENGTH: 33
<212> TYPE: DNA
<213> ORGANISM: Homo sapiens

<400> SEQUENCE: 274
ctcgtgtggg acgacgtcct gaatggcccg gtg                           33

<210> SEQ ID NO 275
<211> LENGTH: 33
<212> TYPE: DNA
<213> ORGANISM: Homo sapiens
```

```
<400> SEQUENCE: 275
caaggagaca gcctcagaag ctattatgca agc                    33

<210> SEQ ID NO 276
<211> LENGTH: 21
<212> TYPE: DNA
<213> ORGANISM: Homo sapiens

<400> SEQUENCE: 276
gctaaaaaca accggccctc a                                 21

<210> SEQ ID NO 277
<211> LENGTH: 30
<212> TYPE: DNA
<213> ORGANISM: Homo sapiens

<400> SEQUENCE: 277
gcgtcccgga acggctggaa ccatgtggta                        30

<210> SEQ ID NO 278
<211> LENGTH: 33
<212> TYPE: DNA
<213> ORGANISM: Homo sapiens

<400> SEQUENCE: 278
caaggagaca gcctcagaag ctattatgca agc                    33

<210> SEQ ID NO 279
<211> LENGTH: 21
<212> TYPE: DNA
<213> ORGANISM: Homo sapiens

<400> SEQUENCE: 279
gctaaaaaca accggccctc a                                 21

<210> SEQ ID NO 280
<211> LENGTH: 30
<212> TYPE: DNA
<213> ORGANISM: Homo sapiens

<400> SEQUENCE: 280
gcgtcccgga acggctggaa ccatgtggta                        30

<210> SEQ ID NO 281
<211> LENGTH: 33
<212> TYPE: DNA
<213> ORGANISM: Homo sapiens

<400> SEQUENCE: 281
caaggagaca gcctcagaag ctattatgca agc                    33

<210> SEQ ID NO 282
<211> LENGTH: 21
<212> TYPE: DNA
<213> ORGANISM: Homo sapiens

<400> SEQUENCE: 282
gctaaaaaca accggccctc a                                 21

<210> SEQ ID NO 283
<211> LENGTH: 30
<212> TYPE: DNA
<213> ORGANISM: Homo sapiens
```

<400> SEQUENCE: 283
gcgtcccgga acggctggaa ccatgtggta                                30

<210> SEQ ID NO 284
<211> LENGTH: 33
<212> TYPE: DNA
<213> ORGANISM: Homo sapiens

<400> SEQUENCE: 284
caaggagaca gcctcagaag ctattatgca agc                            33

<210> SEQ ID NO 285
<211> LENGTH: 21
<212> TYPE: DNA
<213> ORGANISM: Homo sapiens

<400> SEQUENCE: 285
gctaaaaaca accggccctc a                                         21

<210> SEQ ID NO 286
<211> LENGTH: 30
<212> TYPE: DNA
<213> ORGANISM: Homo sapiens

<400> SEQUENCE: 286
gcgtcccgga acggctggaa ccatgtggta                                30

<210> SEQ ID NO 287
<211> LENGTH: 33
<212> TYPE: DNA
<213> ORGANISM: Homo sapiens

<400> SEQUENCE: 287
caaggagaca gcctcagaag ctattatgca agc                            33

<210> SEQ ID NO 288
<211> LENGTH: 21
<212> TYPE: DNA
<213> ORGANISM: Homo sapiens

<400> SEQUENCE: 288
gctaaaaaca accggccctc a                                         21

<210> SEQ ID NO 289
<211> LENGTH: 30
<212> TYPE: DNA
<213> ORGANISM: Homo sapiens

<400> SEQUENCE: 289
gcgacccgga acggctggaa ccatgtggta                                30

<210> SEQ ID NO 290
<211> LENGTH: 33
<212> TYPE: DNA
<213> ORGANISM: Homo sapiens

<400> SEQUENCE: 290
caaggagaca gcctcagaag ctattatgca agc                            33

<210> SEQ ID NO 291
<211> LENGTH: 21
<212> TYPE: DNA
<213> ORGANISM: Homo sapiens

```
<400> SEQUENCE: 291
gctaaaaaca accggccctc a                                                    21

<210> SEQ ID NO 292
<211> LENGTH: 30
<212> TYPE: DNA
<213> ORGANISM: Homo sapiens

<400> SEQUENCE: 292
gcgacccgga acggctggaa ccatgtggta                                           30
```